(12) United States Patent
Gouliaev et al.

(10) Patent No.: US 8,722,583 B2
(45) Date of Patent: May 13, 2014

(54) METHOD FOR SELECTING A CHEMICAL ENTITY FROM A TAGGED LIBRARY

(75) Inventors: Alex Haahr Gouliaev, Veksø Sjælland (DK); Thomas Franch, Copenhagen N (DK)

(73) Assignee: Nuevolution A/S, Copenhagen (DK)

( * ) Notice: Subject to any disclaimer, the term of this patent is extended or adjusted under 35 U.S.C. 154(b) by 1007 days.

(21) Appl. No.: 11/402,957

(22) Filed: Apr. 13, 2006

(65) Prior Publication Data

US 2006/0292603 A1 Dec. 28, 2006

Related U.S. Application Data

(63) Continuation-in-part of application No. 10/525,817, filed as application No. PCT/DK03/00739 on Oct. 30, 2003.

(60) Provisional application No. 60/422,167, filed on Oct. 30, 2002, provisional application No. 60/434,425, filed on Dec. 19, 2002, provisional application No. 60/486,199, filed on Jul. 11, 2003.

(30) Foreign Application Priority Data

| Oct. 30, 2002 | (DK) | 2002 01652 |
| Dec. 19, 2002 | (DK) | 2002 01955 |
| Jul. 11, 2003 | (DK) | 2003 01064 |

(51) Int. Cl.
  *C40B 20/04* (2006.01)
  *C12Q 1/68* (2006.01)
  *C07H 21/04* (2006.01)

(52) U.S. Cl.
  USPC ............ 506/4; 435/6.1; 435/7.1; 435/7.2; 536/23.1; 536/24.3; 530/300; 530/350

(58) Field of Classification Search
  USPC ............ 435/6, 7.1, 7.2; 536/23.1, 24.3; 530/300, 350; 506/4
  See application file for complete search history.

(56) References Cited

U.S. PATENT DOCUMENTS

| 4,822,731 A | 4/1989 | Watson et al. |
| 5,047,519 A | 9/1991 | Hobbs, Jr. et al. |
| 5,324,829 A | 6/1994 | Bahl et al. |
| 5,432,272 A | 7/1995 | Benner |
| 5,437,977 A | 8/1995 | Segev |

(Continued)

FOREIGN PATENT DOCUMENTS

| DE | 196 46 372 C1 | 9/1996 |
| DE | 196 42 751 | 4/1998 |

(Continued)

OTHER PUBLICATIONS

U.S. Appl. No. 09/820,087, filed Mar. 27, 2001, Zhou et al.

(Continued)

*Primary Examiner* — Jezia Riley
(74) *Attorney, Agent, or Firm* — Merchant & Gould P.C.

(57) ABSTRACT

Disclosed is a method for determining the identity of a chemical entity having a preselected property. The chemical entity is identified from a library composed of a plurality of different chemical entities each appended to unique identifier tags. An anti-tag having the capability of specifically interacting with the unique identifier tag is recovered during the method and used for identification purposes.

61 Claims, 8 Drawing Sheets

General Principle of Library Enrichment, Amplification and Identification

(56) References Cited

U.S. PATENT DOCUMENTS

| | | | |
|---|---|---|---|
| 5,449,613 A | 9/1995 | Dordick et al. | |
| 5,451,503 A | 9/1995 | Hogan et al. | |
| 5,473,060 A | 12/1995 | Gryaznov et al. | |
| 5,474,796 A | 12/1995 | Brennan | |
| 5,476,930 A | 12/1995 | Letsinger et al. | |
| 5,503,805 A | 4/1996 | Sugarman et al. | |
| 5,571,677 A | 11/1996 | Gryaznov | |
| 5,571,903 A | 11/1996 | Gryaznov et al. | |
| 5,573,905 A | 11/1996 | Lerner et al. | |
| 5,604,097 A | 2/1997 | Brenner | |
| 5,635,400 A | 6/1997 | Brenner | |
| 5,639,603 A | 6/1997 | Dower et al. | |
| 5,643,722 A | 7/1997 | Rothschild et al. | |
| 5,654,413 A | 8/1997 | Brenner | |
| 5,656,739 A | 8/1997 | Cubicciotti | |
| 5,663,046 A | 9/1997 | Baldwin et al. | |
| 5,665,975 A | 9/1997 | Kedar et al. | |
| 5,681,943 A | 10/1997 | Letsinger et al. | |
| 5,684,169 A | 11/1997 | Hamada et al. | |
| 5,686,243 A | 11/1997 | Royer et al. | |
| 5,708,153 A | 1/1998 | Dower et al. | |
| 5,723,320 A | 3/1998 | Dehlinger | |
| 5,723,598 A | 3/1998 | Lerner et al. | |
| 5,739,386 A | 4/1998 | Holmes | |
| 5,741,643 A | 4/1998 | Gryaznov et al. | |
| 5,763,175 A | 6/1998 | Brenner | |
| 5,763,263 A | 6/1998 | Dehlinger | |
| 5,770,358 A | 6/1998 | Dower et al. | |
| 5,780,613 A | 7/1998 | Letsinger et al. | |
| 5,789,162 A | 8/1998 | Dower et al. | |
| 5,789,172 A | 8/1998 | Still et al. | |
| 5,795,976 A | 8/1998 | Oefner et al. | |
| 5,804,563 A | 9/1998 | Still et al. | |
| 5,817,795 A | 10/1998 | Gryaznov et al. | |
| 5,824,471 A | 10/1998 | Mashal et al. | |
| 5,830,658 A | 11/1998 | Gryaznov et al. | |
| 5,840,485 A | 11/1998 | Lebl et al. | |
| 5,843,650 A | 12/1998 | Segev | |
| 5,846,719 A | 12/1998 | Brenner et al. | |
| 5,880,972 A | 3/1999 | Horlbeck | |
| 5,942,609 A * | 8/1999 | Hunkapiller et al. | 536/25.3 |
| 5,948,648 A | 9/1999 | Khan et al. | |
| 6,001,579 A | 12/1999 | Still et al. | |
| 6,056,926 A | 5/2000 | Sugarman et al. | |
| 6,060,596 A | 5/2000 | Lerner et al. | |
| 6,090,912 A | 7/2000 | Lebl et al. | |
| 6,096,500 A | 8/2000 | Oprandy et al. | |
| 6,096,875 A | 8/2000 | Khan et al. | |
| 6,132,970 A | 10/2000 | Stemmer | |
| 6,140,489 A | 10/2000 | Brenner | |
| 6,140,493 A | 10/2000 | Dower et al. | |
| 6,143,497 A | 11/2000 | Dower et al. | |
| 6,143,503 A | 11/2000 | Baskerville et al. | |
| 6,150,516 A | 11/2000 | Brenner et al. | |
| 6,165,717 A | 12/2000 | Dower et al. | |
| 6,165,778 A | 12/2000 | Kedar et al. | |
| 6,172,214 B1 | 1/2001 | Brenner | |
| 6,194,550 B1 | 2/2001 | Gold et al. | |
| 6,197,555 B1 | 3/2001 | Khan et al. | |
| 6,207,446 B1 | 3/2001 | Szostak et al. | |
| 6,210,900 B1 | 4/2001 | Yamashita et al. | |
| 6,232,066 B1 | 5/2001 | Felder et al. | |
| 6,235,475 B1 | 5/2001 | Brenner et al. | |
| 6,235,889 B1 | 5/2001 | Ulanovsky | |
| 6,248,568 B1 | 6/2001 | Khan et al. | |
| 6,274,385 B1 | 8/2001 | Hocklowski et al. | |
| 6,287,765 B1 | 9/2001 | Cubicciotti et al. | |
| 6,297,053 B1 | 10/2001 | Stemmer | |
| 6,306,587 B1 | 10/2001 | Royer et al. | |
| 6,352,828 B1 | 3/2002 | Brenner | |
| 6,416,949 B1 | 7/2002 | Dower et al. | |
| 6,429,300 B1 | 8/2002 | Kurz et al. | |
| 6,479,264 B1 | 11/2002 | Louwrier | |
| 6,503,759 B1 | 1/2003 | Still et al. | |
| 6,514,736 B1 | 2/2003 | Erlich et al. | |
| 6,537,776 B1 | 3/2003 | Short | |
| 6,593,088 B1 | 7/2003 | Saito et al. | |
| 6,613,508 B1 | 9/2003 | Ness et al. | |
| 6,620,584 B1 | 9/2003 | Chee et al. | |
| 6,620,587 B1 | 9/2003 | Taussig et al. | |
| 6,780,981 B1 | 8/2004 | Southern et al. | |
| 6,936,477 B2 | 8/2005 | Still et al. | |
| 7,070,928 B2 | 7/2006 | Liu et al. | |
| 7,223,545 B2 | 5/2007 | Liu et al. | |
| 7,413,854 B2 | 8/2008 | Pedersen et al. | |
| 7,442,160 B2 | 10/2008 | Liu et al. | |
| 7,479,472 B1 | 1/2009 | Harbury et al. | |
| 7,491,494 B2 | 2/2009 | Liu et al. | |
| 7,557,068 B2 | 7/2009 | Liu et al. | |
| 7,704,925 B2 | 4/2010 | Gouliaev et al. | |
| 7,727,713 B2 | 6/2010 | Pedersen et al. | |
| 7,771,935 B2 | 8/2010 | Liu et al. | |
| 7,915,201 B2 | 3/2011 | Franch et al. | |
| 7,998,904 B2 | 8/2011 | Liu et al. | |
| 8,206,901 B2 | 6/2012 | Freskgard et al. | |
| 2002/0048760 A1 | 4/2002 | Drmanac et al. | |
| 2002/0055125 A1 | 5/2002 | Charych et al. | |
| 2002/0081714 A1 | 6/2002 | Jain et al. | |
| 2002/0115068 A1 | 8/2002 | Tomlinsen et al. | |
| 2002/0127598 A1 | 9/2002 | Zhou et al. | |
| 2002/0142335 A1 | 10/2002 | Strittmatter et al. | |
| 2003/0004122 A1 | 1/2003 | Beigelman et al. | |
| 2003/0050453 A1 | 3/2003 | Sorge | |
| 2003/0113738 A1 | 6/2003 | Liu et al. | |
| 2003/0182068 A1 | 9/2003 | Battersby et al. | |
| 2003/0186233 A1 | 10/2003 | Chesnut et al. | |
| 2004/0049008 A1 | 3/2004 | Pedersen et al. | |
| 2004/0110213 A1 | 6/2004 | Namsaraev | |
| 2004/0161741 A1 | 8/2004 | Rabani et al. | |
| 2004/0185484 A1 | 9/2004 | Costa et al. | |
| 2004/0191812 A1 | 9/2004 | Davydova et al. | |
| 2004/0197845 A1 | 10/2004 | Hassibi et al. | |
| 2004/0209282 A1 | 10/2004 | Ault-Riche et al. | |
| 2005/0025766 A1 | 2/2005 | Liu et al. | |
| 2005/0042669 A1 | 2/2005 | Liu et al. | |
| 2005/0130173 A1 | 6/2005 | Leamon et al. | |
| 2005/0142583 A1 | 6/2005 | Liu et al. | |
| 2005/0170376 A1 | 8/2005 | Liu et al. | |
| 2006/0099592 A1 | 5/2006 | Freskgard et al. | |
| 2006/0121470 A1 | 6/2006 | Pedersen | |
| 2006/0234231 A1 | 10/2006 | Freskgard et al. | |
| 2006/0246450 A1 | 11/2006 | Pedersen | |
| 2006/0269920 A1 | 11/2006 | Freskgard et al. | |
| 2006/0292603 A1 | 12/2006 | Gouliaev et al. | |
| 2007/0026397 A1 | 2/2007 | Freskgard et al. | |
| 2007/0042401 A1 | 2/2007 | Morgan et al. | |
| 2007/0224607 A1 | 9/2007 | Morgan et al. | |
| 2008/0193983 A1 | 8/2008 | Gouliaev et al. | |
| 2008/0305957 A1 | 12/2008 | Thisted et al. | |
| 2009/0035824 A1 | 2/2009 | Liu et al. | |
| 2009/0143232 A1 | 6/2009 | Pedersen et al. | |
| 2009/0149347 A1 | 6/2009 | Liu et al. | |
| 2009/0239211 A1 | 9/2009 | Freskgard et al. | |
| 2009/0264300 A1 | 10/2009 | Franch et al. | |
| 2010/0016177 A1 | 1/2010 | Pedersen et al. | |
| 2011/0230419 A1 | 9/2011 | Lundorf et al. | |
| 2012/0028212 A1 | 2/2012 | Fujii et al. | |
| 2012/0028812 A1 | 2/2012 | Freskgard et al. | |

FOREIGN PATENT DOCUMENTS

| | | |
|---|---|---|
| EP | 0324616 | 7/1989 |
| EP | 0604552 | 4/1993 |
| EP | 0542770 | 5/1993 |
| EP | 0643778 | 10/1993 |
| EP | 0695305 | 10/1994 |
| EP | 0776330 | 10/1996 |
| EP | 0766826 | 4/1997 |
| EP | 0773227 | 5/1997 |
| EP | 0778280 | 6/1997 |
| EP | 0917494 | 10/1998 |
| EP | 0879219 | 11/1998 |
| EP | 0962527 | 12/1999 |
| EP | 1324045 | 7/2003 |

(56) References Cited

FOREIGN PATENT DOCUMENTS

| | | |
|---|---|---|
| EP | 1402024 | 3/2004 |
| EP | 1483585 | 12/2004 |
| EP | 1514938 | 3/2005 |
| EP | 1533385 A1 | 5/2005 |
| EP | 1828381 | 9/2007 |
| EP | 1832567 | 9/2007 |
| JP | 05292967 | 11/1993 |
| JP | 08000268 | 1/1996 |
| WO | 9005785 | 5/1990 |
| WO | 9303172 | 2/1991 |
| WO | 9105058 A1 | 4/1991 |
| WO | WO 91/19818 | 12/1991 |
| WO | WO 92/00091 | 1/1992 |
| WO | WO 92/02536 | 2/1992 |
| WO | WO 93/06121 | 4/1993 |
| WO | WO 93/20242 | 10/1993 |
| WO | 9408051 | 4/1994 |
| WO | WO 94/13623 | 6/1994 |
| WO | WO 94/24143 | 10/1994 |
| WO | WO 95/04160 | 2/1995 |
| WO | 9512608 | 5/1995 |
| WO | 9609316 A1 | 3/1996 |
| WO | 9611878 | 4/1996 |
| WO | 9612014 | 4/1996 |
| WO | 9603418 A1 | 8/1996 |
| WO | 9624847 | 8/1996 |
| WO | WO 96/24061 | 8/1996 |
| WO | 9635699 | 11/1996 |
| WO | 9640201 | 12/1996 |
| WO | WO 96/41011 | 12/1996 |
| WO | WO97/04131 | 2/1997 |
| WO | 9711958 | 4/1997 |
| WO | 9719039 | 5/1997 |
| WO | WO 97/27317 | 7/1997 |
| WO | WO 97/35198 | 9/1997 |
| WO | WO 98/01562 | 1/1998 |
| WO | 9831700 | 7/1998 |
| WO | 9847613 | 10/1998 |
| WO | 9856904 | 12/1998 |
| WO | 9858256 | 12/1998 |
| WO | 9942605 A1 | 8/1999 |
| WO | WO 99/51546 | 10/1999 |
| WO | WO 99/51773 | 10/1999 |
| WO | 9964378 A2 | 12/1999 |
| WO | 0021909 A2 | 4/2000 |
| WO | 0023458 | 4/2000 |
| WO | WO 00/23456 | 4/2000 |
| WO | WO 00/23458 | 4/2000 |
| WO | 0024882 | 5/2000 |
| WO | 0032823 | 6/2000 |
| WO | 0040695 A2 | 7/2000 |
| WO | 0047775 | 8/2000 |
| WO | 0061775 | 10/2000 |
| WO | 0100876 | 1/2001 |
| WO | 01/07690 | 2/2001 |
| WO | WO 01/07657 | 2/2001 |
| WO | WO 01/53539 | 7/2001 |
| WO | 0156955 A1 | 8/2001 |
| WO | WO 01/90414 | 11/2001 |
| WO | 0203067 | 1/2002 |
| WO | WO 02/10186 | 2/2002 |
| WO | WO 02/34948 | 5/2002 |
| WO | WO 02/40664 | 5/2002 |
| WO | 02074929 A2 | 9/2002 |
| WO | WO 02/074978 | 9/2002 |
| WO | WO 02/083951 | 10/2002 |
| WO | 02102820 | 12/2002 |
| WO | 02103008 | 12/2002 |
| WO | WO 02/099078 | 12/2002 |
| WO | WO 02/103008 | 12/2002 |
| WO | WO 03/025567 | 3/2003 |
| WO | WO 03/062417 | 7/2003 |
| WO | 03078050 | 9/2003 |
| WO | 03078445 | 9/2003 |
| WO | 03078446 | 9/2003 |
| WO | 03078625 | 9/2003 |
| WO | 03078626 | 9/2003 |
| WO | 03078627 | 9/2003 |
| WO | WO 03/076943 | 9/2003 |
| WO | 03082901 A2 | 10/2003 |
| WO | 03106679 | 12/2003 |
| WO | 2004001042 | 12/2003 |
| WO | 2004009814 A1 | 1/2004 |
| WO | WO 2004/007529 | 1/2004 |
| WO | 2004013070 | 2/2004 |
| WO | 2004016767 A2 | 2/2004 |
| WO | 2004024929 | 3/2004 |
| WO | 2004039962 A2 | 5/2004 |
| WO | 2004042019 A2 | 5/2004 |
| WO | WO 2004/039825 | 5/2004 |
| WO | 2004056994 | 7/2004 |
| WO | 2004074429 | 9/2004 |
| WO | 2004074501 | 9/2004 |
| WO | 2004083427 | 9/2004 |
| WO | 2004099441 A2 | 11/2004 |
| WO | 2004110964 | 12/2004 |
| WO | 2005003778 | 1/2005 |
| WO | 2005026387 A1 | 3/2005 |
| WO | WO 2005/058479 A2 | 6/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | 2006128039 A2 | 11/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 A2 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 A2 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

U.S. Appl. No. 10/060,639, filed Jan. 30, 2002, Strittmatter.
U.S. Appl. No. 10/699,088, filed Oct. 30, 2003, Ault-Riche et al.
Nemoto, N et al. "In vitro virus: bonding of mRNA bearing puromycin at the 3'-terminal end to the C-terminal end of its encoded protein on the ribosome in vitro". FEBS Lett. Sep. 8, 1997;414(2):405-8.
Roberts, RW et al. "RNA-peptide fusions for the in vitro selection of peptides and proteins". Proc Natl Acad Sci U S A. Nov. 11, 1997;94(23):12297-302.
Kurz, M et al. Psoralen photo-crosslinked mRNA-puromycin conjugates: a novel template for the rapid and facile preparation of mRNA-protein fusions. Nucleic Acids Res. Sep. 15, 2000;28(18):E83.
Keiler et al. "Role of a peptide tagging system in degradation of proteins synthesized from damaged messenger RNA". Science. Feb. 16, 1996;271(5251):990-3.
Benner, SA. "Expanding the genetic lexicon: incorporating non-standard amino acids into proteins by ribosome-based synthesis". Trends Biotechnol. May 1994;12(5):158-63.
Mendel, D. "Site-directed mutagenesis with an expanded genetic code". Annu. Rev. Biophys. Biomol. Struc. 1995. 24:463-93.
Liu DR et al. "Engineering a tRNA and aminoacyl-tRNA synthetase for the site-specific incorporation of unnatural amino acids into proteins in vivo". Proc Natl Acad Sci U S A. Sep. 16, 1997;94(19):10092-7.

(56) References Cited

OTHER PUBLICATIONS

Liu DR et al. "Progress toward the evolution of an organism with an expanded genetic code". Proc Natl Acad Sci USA. Apr. 27, 1999;96(9):4780-5.
Liu, R et al. "Optimized synthesis of RNA-protein fusions for in vitro protein selection". Methods Enzymol. 2000;318:268-93.
Wang, L et al. "A new functional suppressor tRNA/aminoacyl-tRNA synthetase pair for the in vivo incorporation of unnatural amino acids into proteins" J. Am. Chem. Soc 2000, 122, 5010-5011 Pub Apr. 5, 2000.
Ellman J.A., et al. "Biosynthetic method for introducing Unnatural Amino acids site specifically into proteins". Methods Enzymol. 202, 301-336 (1992).
José Salas et al. "Biosynthetic Polydeoxynucleotides as Direct Templates for Polypeptide Synthesis". J. of Biological Chemistry, vol. 243, No. 6, 1968, p. 1012-1015.
Walder JA, Walder RY, Heller MJ, Freier SM, Letsinger RL, Klotz IM. "Complementary carrier peptide synthesis: general strategy and implications for prebiotic origin of peptide synthesis". Proc Natl Acad Sci U S A. Jan. 1979;76(1):51-5.
Bruick et al. "Template-directed ligation of peptides to oligonucleotides" Chemistry and Biology, vol. 3, No. 1, Jan. 1996, p. 49-56.
Tamura K, Schimmel P. "Oligonucleotide-directed peptide synthesis in a ribosome- and ribozyme-free system". Proc Natl Acad Sci U S A. Feb. 13, 2001;98(4):1393-7.
Lewis RJ, Hanawalt PC. "Ligation of oligonucleotides by pyrimidine dimers—a missing 'link' in the origin of life?"22;298(5872):393-6.
Liu J, Taylor JS. "Template-directed photoligation of oligodeoxyribonucleotides via 4-thiothymidine". Nucleic Acids Res. Jul. 1, 1998;26(13):3300-4.
Fujimoto et al. "Template-directed photoreversible ligation of deoxyoligonucleotides via 5-Vinyldeoxyuridine" J. Am. Soc. 2000, 122, 5646-5647.
Kenzo Fujimoto, Shigeo Matsuda, Naoki Ogawa, Masayuki Hayashi & Isao Saito "Template-directed reversible photocircularization of DNA via 5-vinyldeoxycytidine". Tetrahedron Letters 2000, 41:33:6451-6454.
Gryaznov SM, Letsinger RL. "Template controlled coupling and recombination of oligonucleotide blocks containing thiophosphoryl groups". Nucleic Acids Res. Mar. 1993 25;21(6):1403-8.
Gryaznov SM, Schultz R, Chaturvedi SK, Letsinger RL. "Enhancement of selectivity in recognition of nucleic acids via chemical autoligation". Nucleic Acids Res. Jun. 25, 1994;22(12):2366-9.
Herrlein MK, Letsinger RL. "Selective chemical autoligation on a double-stranded DNA template". Nucleic Acids Res. Nov. 25, 1994;22(23):5076-8.
Letsinger, RL; Wu, T; Elghanian, R "Chemical and photochemical ligation of oligonucleotide blocks". Nucleosides and nucleotides, 16(5&6), 643-652 (1997).
Visscher J, Schwartz AW "Template-directed synthesis of acyclic oligonucleotide analogues". J Mol Evol. Dec. 1988-Feb. 1989;28(1-2):3-6.
Visscher J, Bakker CG, van der Woerd R, Schwartz AW "Template-directed oligomerization catalyzed by a polynucleotide analog". Science. Apr. 21, 1989;244(4902):329-31.
Visscher J, van der Woerd R, Bakker CG, Schwartz AW. "Oligomerization of deoxynucleoside-bisphosphate dimers: template and linkage specificity". Orig Life Evol Biosph. 1989;19(1):3-6.
Zhan, ZJ and Lynn, DG "Chemical Amplification through template-directed synthesis". J. Am. Chem. Soc. 1997, 119, 12420-1.
Bruick RK, Koppitz M, Joyce GF, Orgel L.E. "A simple procedure for constructing 5'-amino-terminated oligodeoxynucleotides in aqueous solution Nucleic Acids Res". Mar. 15, 1997;25(6):1309-10.
Albagli, D; Atta, RVA; Cheng, P; Huan, B and Wood, ML. "Chemical amplification (CHAMP) by a continuous, self-replicating oligonucleotide-based system" J. Am. Chem. Soc. 1999, 121, 6954-6955. Pub. on the web Jul. 14, 1999.

Xu, Y and Kool, E "Rapid and Selective selenium-mediated autoligation of DNA strands" J. Am. Chem. Soc. 2000, 122, 9040-1 Pub. on web Aug. 31, 2000.
Xu Y, Karalkar NB, Kool ET. "Nonenzymatic autoligation in direct three-color detection of RNA and DNA point mutations". Nat Biotechnol. Feb. 2001;19(2):148-52.
Li X, Zhan ZY, Knipe R, Lynn DG. "DNA-catalyzed polymerization". J Am Chem Soc. Feb. 6, 2002;124(5):746-7.
Czlapinski, JL and Sheppard, TL. "Nucleic acid template-directed assembly of metallosalen-DNA conjugates". J Am Chem Soc. Sep. 5, 2001;123(35):8618-9 published on the web Aug. 10, 2001.
Leitzel JC, Lynn DG "Template-directed ligation: from DNA towards different versatile templates". Chem Rec. 2001;1(1):53-62. Published online Jan. 30, 2001.
Schmidt JG, Nielsen PE, Orgel L.E. "Information transfer from peptide nucleic acids to RNA by template-directed syntheses". Nucleic Acids Res. Dec. 1, 1997;25(23):4797-802.
Dower, WJ et al. "In vitro selection as a powerful tool for the applied evolution of proteins and peptides".Current Opinion in Chemical Biology, 2002, 6:390-398.
Brenner, S and Lerner, RA . "Encoded combinatorial chemistry" Proc. Natl. Acad. Sci. USA. vol. 89, p. 5381-3, Jun. 1992.
Gartner, Z; Liu, DR "The generality of DNA-templated synthesis as a basis for evolving non-natural small molecules". J Am Chem Soc. Jul. 18, 2001;123(28):6961-3.
David Liu. "Expanding the reaction scope of DNA-templated synthesis Angew". Chem. Int. Ed. 2002, 41, No. 10 pp. 1796-1800. Published May 15, 2002.
Gartner, ZJ et al. "Multistep small-molecule synthesis programmed by DNA templates", J. Am. Chem. Soc. vol. 124, No. 35, 2002, 10304-10306.
Calderone, CT et al. "Directing otherwise incompatible reactions in a single solution by using DNA-templated organic synthesis". Angew Chem Int Ed, 2002, 41, No. 21. 4104-4108.
Bittker, JA; Phillips, KJ and Liu, DR "Recent advances in the in vitro evolution of nucleic acids". Curr Opin Chem Biol. Jun. 2002;6(3):367-74, Review. Pub. on the web Mar. 20, 2002.
Summerer,D and Marx, A "DNA-templated synthesis: more versatile than expected". Angew Chem Int Ed Engl. Jan. 4, 2002;41(1):89-90. Review.
Gartner, ZJ et al. "Two enabling architectures for DNA-templated organic synthesis". Angew. Chem Int. Ed. 2003, 42, No. 12, 1370-1375.
Rosenbaum, DM et al. "Efficient and sequence-specific DNA-templated polymerization of peptide nucleic acid aldehydes". J. Am. Chem. Soc. vol. 125, No. 46, 2003, 13924-13925.
Li, X et al. "Stereoselectivity in DNA-templated organic synthesis and its origins". J. Am. Chem. Soc. vol. 125, No. 34, 2003, 10188-10189.
Gordon, EM et al. "Applications of combinatorial technologies to drug discovery. 2. Combinatorial organic synthesis, library screening strategies, and future directions". Journal of Medicinal Chemistry, vol. 37, No. 10, May 13, 1994.
Otto, S et al. S"Recent developments in dynamic combinatorial chemistry". Current opinion in Chemical Biology 2002, 6: 321-327.
Pavia, MR "The Chemical generation of molecular diversity". http://www.netsci.org/Science/Combichem/feature01.html.
Braun, E, et al. "DNA-templated assembly and electrode attachment of a conducting silver wire". Nature, vol. 391, Feb. 19, 1998, 775-778.
Beger, M et al. "Universal bases for hybridization, replication and chain termination", Nucleic acids research, Oxford University Press, vol. 28, No. 15, pub. Aug. 1, 2000, p. 2911-2914.
Weizman, H et al. "2,2'-Bipyridine ligandoside: a novel building block for modifying DNA with intra-duplex metal complexes". J. Am. Chem. Soc. 2001, 123, 3375-3376.
Frutos, AG et al. "Demonstration of a word design strategy for DNA computing on surfaces". Nucleic Acids Research, 1997, vol. 25, No. 23, 4748-4757.
Loweth, CJ et al. "DNA-based assembly of gold nanocrystals". Angew. Chem. Int. Ed. 1999, 38, No. 12. 1808-1812.

(56) References Cited

OTHER PUBLICATIONS

Elghanian, R et al. "Selective colorimetric detection of polynucleotides based on the distance-dependent optical properties of gold nanoparticles". Science, vol. 277, Aug. 22, 1997.
Storhoff, JJ and Mirkin, CA. "Programmed Materials Synthesis with DNA". Chem Rev. Jul. 14, 1999;99(7):1849-1862.
Mirkin CA. "Programming the assembly of two- and three-dimensional architectures with DNA and nanoscale inorganic building blocks". Inorg Chem. May 29, 2000;39(11):2258-72.
Waybright SM, Singleton CP, Wachter K, Murphy CJ, Bunz UH. "Oligonucleotide-directed assembly of materials: defined oligomers". J Am Chem Soc. Mar. 7, 2001;123(9):1828-33. Pub. on web Feb. 7, 2001.
DeWitt, SH et al. "Diversomers": an approach to nonpeptide, nonoligomeric chemical diversity. Proc. Natl. Acad. Sci, USA, vol. 90, pp. 6909-6913, Aug. 1993.
Ohlmeyer, MHJ et al. "Complex synthetic chemical libraries indexed with molecular tags". Proc. Natl. Acad, Sci, USA, vol. 90, pp. 10922-10926, Dec. 1993, Chemistry.
Zuckermann, RN et al. "Discovery of nanomolar ligands for 7-transmembrane G-protein-coupled receptors from a diverse N-(substituted) glycine peptoid library". J. Med. Chem. 1994, 37, 2678-2685.
Luo, P. et al. "Analysis of the structure and stability of a backbone-modified oligonucleotide: implications for-avoiding product inhibition in catalytic template-directed synthesis". J. Am. Chem. Soc. 1998, 120, 3019-3031.
Luther, A et al. "Surface-promoted replication and exponential amplification of DNA analogues". Nature, vol. 396, Nov. 19, 1998, 245-248.
Klekota, B et al. "Selection of DNA-Binding Compounds via Multistage Molecular Evolution". Tetrahedron 55 (1999) 11687-11697.
Furlan, RLE et al. "Molecular amplification in a dynamic combinatorial library using non-covalent interactions". Chem. Commun., 2000, 1761-1762.
Ramström, O et al. "In situ generation and screening of a dynamic combinatorial carbohydrate library against concanavalin A". ChemBioChem, 2000, 1, 41-48.
Cousins, GRL et al. "Identification and Isolation of a Receptor for N-Methyl Alkylammonium Salts: Molecular Amplification in a Pseudo-peptide Dynamic Combinatorial Library". Angew. Chem. Int. Ed., 2001, 40, No. 2, 423-427.
Roberts, Si et al. "Simultaneous selection, amplification and isolation of a pseudo-peptide receptor by an immobilised N-methyl ammonium ion template". Chem. Commun., 2002, 938-939.
Furka, A "Combinatorial Chemistry: 20 years on . . ." Drug discovery today vol. 7, No. 1, p. 1-4, 2002.
Nielsen, J et al. "Synthetic Methods for the Implementation of Encoded Combinatorial Chemistry" J. Am. Chem. Soc., 1993, 115, 9812-9813.
Needels, CM et al. "Generation and screening of an oligonucleotide-encoded synthetic peptide library" Proc. Natl. Acad. Sci., USA, vol. 90, pp. 10700-10704. Nov. 1993, Chemistry.
Kerr, JM et al. "Encoded Combinatorial Peptide Libraries Containing Non-Natural Amino Acids" J. Am. Chem. Soc., USA. 1993, 115, 2529-2531.
Nestler, HP et al. A general Method for Molecular Tagging of Encoded Combinatorial Chemistry Libraries J. Org. Chem., 1994, 59, 4723-4724.
Baldwin, JJ et al. "Synthesis of a Small Molecule Combinatorial Library Encoded with Molecular Tags" J. Am. Chem. Soc. 1995, 117, 5588-5589.
Nikolaiev. v et al. "Peptide-Encoding for structure determination of nonsequenceable polymers within libraries synthesized and tested on solid-phase supports" Peptide Research, vol. 6, No. 3, 1993. pp. 161-170.
"The Nucleus", Jan. 2004, vol. LXXXII, No. 5, R. Grubina; "Summer Research Report: R. Grubina on DNA Templated Synthesis for Small Molecule Library", p. 10-14.

Nazarenko et al., "A closed tube format for amplification and detection of DNA based on energy transfer", Nucleic Acids Research, 1997, vol. 25, No. 12, p. 2516-2521.
Chan et al., "Intra-tRNA distance measurements for nucleocapsid protein-dependent tRNA unwinding during priming of HIV reverse transcription", PNAS vol. 96, p. 459-464, Jan. 1999.
Rodriguez et al., "Template-directed extension of a guanosine 5'-phosphate covalently attached to an oligodeoxycytidylate template", J Mol Evol (1991) 33:477-482.
Inoue et al, Oligomerization of (Guanosine 5'-phosphor)-2-methylimidazolide on Poly(C), J. Mol. Biol. (1982), 162, 201-217.
C. B. Chen et al., "Template-directed synthesis on Oligodeoxycytidylate and Polydeoxycytidylate templates" J. Mol. Biol. 1985, 181, 271.
H. Rembold et al., "Single-strand regions of Poly(G) act as templates for oligo(C) synthesis" J. Mol. Evol. 1994, 38, 205.
T. Inoue et al., "A nonenzymatic RNA polymerase model", Science 1983, 219, p. 859-862.
O. L. Acevedo et al., "Non-enzymatic transcription of an oligonucleotide 14 residues long", J. Mol. Biol. 1987, 197, p. 187-193.
C. Böhler et al.,"Template switching between PNA and RNA oligonucleotides", Nature 1995, 376, 578-581.
Acevedo et al., "Template-directed oligonucleotide ligation on hydroxylapatite", Nature vol. 321, Jun. 19, 1986, p. 790-792.
Piccirilli, "RNA seeks its maker", Nature vol. 376, Aug. 17, 1995, p. 548.
A. W. Schwartz et al., "Template-directed synthesis of novel, nucleic acid-like structures", Science 1985, 228, 585-7.
Halpin et al.: DNA display III. Solid-phase organic synthesis on unprotected DNA. PLoS Biol. Jul. 2004;2(7):E175. Epub Jun 22, 2004.
Halpin et al.: DNA display II. Genetic manipulation of combinatorial chemistry libraries for small-molecule evolution. PLoS Biol. Jul. 2004;2(7):E174. Epub Jun. 22, 2004.
Halpin et al.: DNA display I. Sequence-encoded routing of DNA populations. PLoS Biol. Jul. 2004;2(7):E173. Epub Jun. 22, 2004.
"Translation of DNA into Synthetic N-Acyloxazolidines" Li, X.; Gartner, Z. J.; Tse, B. N.; Liu, D. R. J. Am. Chem. Soc. 126, 5090-5092 (2004).
"DNA-Templated Organic Synthesis: Nature's Strategy for Controlling Chemical Reactivity Applied to Synthetic Molecules" Li, X.; Liu, D. R. Angew. Chem. Int. Ed. 43, 4848-4870 (2004).
"DNA-Templated Organic Synthesis and Selection of a Library of Macrocycles" Gartner, Z. J.; Tse, B. N.; Grubina, R.; Doyon, J. B.; Snyder, T. M.; Liu, D. R. Science 305, 1601-1605 (2004).
"Nucleic Acid-Templated Synthesis as a Model System for Ancient Translation" Calderone, C. T. and Liu, D. R. Curr. Opin. Chem. Biol. 8, 645-653 (2004).
"DNA-Templated Functional Group Transformations Enable Sequence-Programmed Synthesis Using Small-Molecule Reagents" Sakurai, K.; Snyder, T. M.; Liu, D. R. J. Am. Chem. Soc. 127, 1660-1661 (2005).
"Translating DNA into synthetic Molecules", David R. Liu, PLoS Biology, Jul. 2004, vol. 2, Iss. 7, p. 905-6.
"The Development of Amplifiable and Evolvable Unnatural Molecules", David R. Liu, Harvard Univ. Cambridge MA Dept of Chemistry and Chemical Biology, Report dated Aug. 4, 2003 No. A104614, approved for public release.
Website of Prof. David R. Liu, publicly available Mar. 11, 2000.
Website of Prof. David R. Liu, publicly available Oct. 15, 2000.
Website of Prof. David R. Liu, publicly available Mar. 1, 2001.
Website of Prof. David R. Liu, publicly available Apr. 19, 2001.
Website of Prof. David R. Liu, publicly available Sep. 23, 2001.
Website of Prof. David R. Liu, publicly available Sep. 24, 2002.
Website of Prof. David R. Liu, publicly available Nov. 20, 2002.
Website of Prof. David R. Liu, publicly available Oct. 15, 2003.
Doyon, J.B et al. "Highly sensitive in vitro selections for DNA-linked synthetic small molecules with protein binding affinity and specificity" J. Am. Chem. Soc, Sep. 16, 2003.
Kanan, M.W et al. "Reaction discovery enabled by DNA-templated synthesis and in vitro selection" Nature, vol. 431, Sep. 30, 2004.

(56) References Cited

OTHER PUBLICATIONS

Fredriksson et al., "Protein detection using proximity-dependent DNA ligation assays", Nature Biotechnology, vol. 20, p. 473-477, May 2002.
Lowe et al., "Combinatorial Libraries for Studying Molecule Recognition", URL: iupac.org/symposia/proceedings/phuket97/lowe.html, downloaded in Jun. 2005.
Czarnik et al., "Encoding methods for combinatorial chemistry", Current Opinion in Chemical Biology vol. 1, Iss 1, Jun. 1997, p. 60-66.
Battersby et al., "Optical encoding of micro-beads for gene screening: alternatives to micro-arrays", Drug Discovery Today, vol. 6, Supp 1, Jun. 1, 2001, p. 19-26.
Shchepinov et al., "Trityl tags for encoding in combinatorial synthesis", Tetrahedron 56 (2000) 2713-2724.
Geysen et al., "Combinatorial Compound Libraries for Drug Discovery: An Ongoing Challenge", Nature Reviews, Drug Discovery, vol. 2, Mar. 2003, p. 222-230.
A new affinity reagent for the site-specific, covalent attachment of DNA to active-site nucleophiles: application to the EcoRI and Rsrl restriction and modification enzymes; Andrei A. Purmal et al.; Nucleic Acids Research; vol. 20, No. 14; 1992 Oxford University Press; pp. 3713-3719.
Abravaya et al., "Detection of point mutation with a modified ligase chain reaction (GAP-LCR)", Nucleic Acids Research, vol. 23, No. 4, 675-682 (1995).
Acinas et al., "PCR-Induced Sequence Artifacts and Bias: Insights from Comparison of Two 16S rRNA Clone Libraries Constructed from the same Sample", Applied and Environmental Microbiology, vol. 71, No. 12, 8966-8969, (2005).
Why are enzymes less active in organic solvent than in water?; Alexander M. Klibanov; Trends in Biotechnology; vol. 15, Issue 3, 97-101; Mar. 1, 1997.
An orthogonal oligonucleotide protecting group strategy that enables assembly of repetitive or highly structured DNAs; Ulf M. LindstOm and Erik T. Kool; Nucleic Acids Res. Oct. 1, 2002; 30(19), e101; 2002 Oxford University Press.
As Fast and Selective as Enzymatic Ligations: Upaired Nucleobases Increase the Selectivity of DNA-Controlled Native Chemical PNA Ligation; Simon Ficht et. al.; ChemBioChem; vol. 6 Issue 11 (2005), pp. 2098-2103.
Baldwin, "Design, Synthesis and use of binary encoded synthetic chemical libraries", Moleculat Diversity, 2, 81-88 (1996).
Baran et al., "Total Synthesis of Marine natural products without using protecting groups", Nature, vol. 446, 404-408 (2007).
Barany, "Genetic disease detection and DNA amplification using cloned thermostable ligase", Proc. Natl. Acad., vol. 88, 189-193 (1991).
Biocatalysis in the Pharmaceutical and Biotechnology Industries; edited by Ramesh N. Patel; CRC Press; Taylor & Francis Group; pp. 791; 819-820 (2006).
Biotransformations in organic synthesis; Wendy A. Loughlin; Bioresource Technology 74 (2000); pp. 49-62.
Borman, "Combinatorial chemists focus on small molecules, molecular recognition, and automation", Chemical & Engineering News, Feb. 12, 1996.
Braasch et al., "Locked nucleic acids (LNA): fine-tuning the recognition pf DNA and RNA", Elsevier, Chemistry & Biology, 8, 1-7 (2001).
Branch capture reactions: displacers derived from asymmetric PCR; Daphne M. Wong; et al; 1991 Oxford University Press; Nucleic Acids Research; vol. 19; No. 9; pp. 2251-2259.
Buller, "Drug Discovery with DNA-Encoded Chemical Libraries", Bioconjugate Chem., vol. 21 (9), pp. 1571-1580, (2010).
Canne et al., "Chemical Protein Synthesis by Solid Phase Ligation of Unprotected Peptide Segments", J. Am. Chem. Soc., 8720-8727 (1999).
Chemicall reactions within DNA duplexes; Cyanogen bromide as an effective oligodeoxyribonucleotide coupling agent; N.I. Sokolova et al.; FEBS Letters, vol. 232, No. 1, pp. 153-155; May 1988.
Chen et al., "Enzymes in Nonaqueous Solvents", Methods in Biotechnology, vol. 15, 373-374 (2001).
Circular RNA oligonucleotides. Synthesis, nucleic acid binding properties, and a comparison with circular DNAs; Shaohui Wang and Eric T. Kool; Nucleic Acids Research, 1994, vol. 22, No. 12; 1994 Oxford University Press; pp. 2326-2333.
Czarnik, "Encoding methods for combinatorial chemistry", Current Opinion in Chemical Biology (1997), 1, p. 60-66.
DCI—A Logical Alternative Activator, Glen Research, vol. 10, No. 1, 1-12 (1997).
Xu Y. et al., "Non-Enzymatic Ligation of Single-Stranded and Duplex DNA", Abstract, Glen Research Catalog Tetrahedron Letters (1997) 38:5595-5598.
Development and trends in enzyme catalysis in nonconventional medai; Sajja Hari Krishna; Biotechnology Advances; vol. 20, Issues 3-4; Nov. 2002; pp. 239-267-Abstract.
Direct Evolution Process for Robust Enzyme Catalysis in Organic Solvents; Dan Robetson; Report Date: Sep. 1996.
DNA Ligase: Structure, Mechanism, and Function; The joining of DNA chains by DNA ligase is an essential component of DNA repair, replication, and recmobination I.R. Lehman; Science vol. 186; 1974; pp. 790-797.
DNA Ligases: Progress and Prospects; Stewart Shuman; jbc.org/content/284/26/17365.full downloaded, Dec. 2, 2010.
DNA Ligases; adnadn.umd.edu/biochem/kahn/molmachines/replications/DNA%20Ligase.htm downloaded, Dec. 10, 2009.
DNA Phosphoramidites & CPGs; http://www.qualitysystems.com.tw/proligo/dna%20phosphoamidities%20&%20cpg's.htm, Dec. 2, 2010.
DNA-encoded chemical libraries; Jörg Scheuermann, et al.; Science Direct; Journal of Biotechnology 126 (2006) 568-581.
DNA-ligases; Stanley Tabor; Currenct Protocols in Molecular Biology (1987) 3.14.1-3.14.4.
Dokl Akad Nauk SSSR, vol. 258, 1242-1245, Krynetskya NF Tumanov YV (1981).
Dolinnaya and Shabarova, "Chemical ligation as a method for the assembly of double-stranded nucleic acids: Modifications and local structure studies", Russian Chemical Bulletin, vol. 45, No. 8, 1996.
Dolinnaya et al., "Structural and kinetic aspects of chemical reactions in DNA duplexes. Information on DNA local structure obtained from chemical ligation data", Nucleic Acids Research, vol. 19, No. 11, 3073-3080 (1991).
Drabovich et al., "Selection of Smart Small-Molecule Ligands: The Proof of Principle", Analytical Chemistry, vol. 81, No. 1, 490-494 (2009).
Drew, "Drug Discovery: A Historical Perspective", Science vol. 287, 2000.
Dreyer et al., "Enzyme Catalysis in Nonaqueous Media: Past, Present, and Future" in Patel (ed.), "Biocatalysis in the Pharmaceutical and Biotechnology Industries", 819-820 (2006).
Enhancement of selectivity in recognition of nucleic acids via chemical autoligation; Sergei M. Gryaznov et.al.; Nucleic Acids Research, 1994, vol. 22, No. 12; 1994 Oxford University Press; pp. 2366-2369.
Enzyme Activity in Organic Solvent As A function Of Water Activity Determined By Membrane Inlet Mass Spectometry; Hans Degn et al.; Biotechnology Techniques vol. 6; No. 2; Mar./Apr. 1992; pp. 161-164—p. 161.
Enzyme Engineering for Nonaqueous Solvents: Random Mutagenesis to Enhance Activity of Subtilisin E in Polar Organic Media; Keqin Chen & Frances H. Arnold; Bio/Technology 9, 1073-1077 (1991)-Abstract.
Enzymes in Nonaqueous Solvents; Applications in Carbohydrate and Peptide Preparation; Shui-Tein Chen et.al.; Methods of Biotechnology; vol. 15; p. 373-374 (2001).
Evolution of DNA and RNA as catalysts for chemical reactions; Andres Jäschke and Burckhard Seelig; Current Opinion in Chemical Biology 2000; 4; pp. 257-262.
Ficht et al., "As Fast and Selective as Enzymatic Ligations: Unpaired Nucleobases Increase the Selectivity of DNA-Controlled Native Chemical PNA Ligation", ChemBioChem, vol. 6, Issue 11, 2098-2103 (2005).

(56) References Cited

OTHER PUBLICATIONS

Furka and Bennett, Combinatorial Libraries by Portioning and Mixing, Combinatorial Chemistry & High Throughput Screening, 1999, 2, 105-122.
Gryanov et al., "Template controlled coupling and recombination of oligonucleotide blocks containing thiophosphoryl groups", Nucleic Acids Research, vol. 21, No. 6, 1403-1408 (1993).
Gumport et al., "T4 RNA Ligase as a Nucleic Acids Synthesis and Modification Reagent", Elsevier North Holland, Inc., 314-345 (1981).
Harada et al., "Unexpected substrate specificity of T4 DNA Ligase revealed by in vitro selection", Nucleic Acids Research, vol. 21, No. 10, 2287-2291 (1993).
Harada, "In vitro selection of optimal DNS substrates for ligation by a water-soluble carbodiimide", J Mol Evol., 38, 6, 558-560 (1994).
Herpin et al., "Synthesis of a 10 000 member 1,5-Benzodiazepine-2-one Library by the Directed Sorting Method", J. Comb. Chem., 2, 513-521 (2000).
Australian Entitlement Dispute—Ren Advice (Oct. 22, 2008).
Australian Entitlement Dispute—Sec 36 Req and Notice to Produce (Nov. 25, 2008).
Australian Entitlement Dispute—Delegates Response (Dec. 2, 2008).
Australian Entitlement Dispute—Advice Applicant Defending Entitlement (Dec. 18, 2008).
Australian Entitlement Dispute—Req Notice to Produce Requestor (Dec. 23, 2008).
Australian Entitlement Dispute—Application Letter (Aug. 11, 2009).
Australian Entitlement Dispute—Req Withdraw (Aug. 12, 2009).
Australian Entitlement Dispute—Ack s32 s36 Withdraw (Aug. 14, 2009).
"Finding reactions in a haystack: Try'em all, see what works", Meeting American Chemical Society, Sep. 10, 2004, vol. 305, Science. p. 1558.
Doyon, J.B et al. "Highly sensitive in vitro selections for DNA-linked synthetic small molecules with protein binding affinity and specificity", J. Am. Chem. Soc., 125, 12372-12373 (2003).
Fujimoto, et al., "Template-directed photochemical synthesis of branched oligodeoxynucleotides via 5-carboxyvinyldeoxyuridine", Tetrahedron Letters, vol. 41:49, pp. 9437-9440, 2000.
Gryaznov, et al., "Chemical Ligation of oligonucleotides in the presence and absence of a template", J. Amer. Chem. Soc., vol. 115, pp. 3808-3809, 1993.
Jones, J. Bryan, et al. "Enzymes in organic synthesis 22. Effects of organic solvents on horse liver alcohol dehydrogenase-catalyzed reduction"; Can. J. Chem. 60 1982; pp. 335-338.
Kinoshita et al., "Enzymatic synthesis of code regions for encoded combinatiorial chemistry /ECC)", Nucleic Acids Symposium, Series No. 34, 201-202, 1995.
Kurz, M., et al. "An efficient synthetic strategy for the preparation of nucleic acid-encoded peptide and protein libraries for in vitro evolution protocols". Fourth International Electron Conference on Synthetic Organic Chemistry (ECSOC-4), www.mdpi.org/ecsoc-4.htm, Sep. 1-30, 2000.
Liu, DR., et al., "DNA-templated synthesis as a basis for the evolution of synthetic molecules.", Abstracts of Papers of the American Chemical Society 225:612-ORGN, Part 2, Mar. 2003.
Smith, Bruce, et al., "DNA-guided assembly of proteins as a pathway to an assembler", (wadsworth.org/albcon97/abstract/krummena. htm) The 1997 Albany Conference: Biomolecular Motors and Nanomachines.
Tanaka, K., et al. "Synthesis of a novel nucleoside for alternative DNA base pairing through metal complexation", J. Org. Chem. 1999, 64, 5002-5003.
Office Actions from U.S. Appl. No. 10/525,817 mailed Nov. 28, 2007.
Office Actions from U.S. Appl. No. 10/525,817 mailed Jul. 7, 2009.
Office Actions from U.S. Appl. No. 10/525,817 mailed May 9, 2007.
Office Actions from U.S. Appl. No. 10/525,817 mailed Jun. 5, 2008.
Office Actions from U.S. Appl. No. 10/525,817 mailed Apr. 1, 2010.
Office Actions from U.S. Appl. No. 10/525,817 mailed Apr. 5, 2010.
Weisst, et al. "Enzymatic Breakage and Joining of Deoxyribonucleic Acid, I. Repair of Single-Strand Breaks in DNA by an Enzyme System From *Escherichia Coli* Infected With T4 Bacteriophage*'" PNAS 1967, 57, (4): 1021-1028.
Anonymous. "Preparing Oligonucleotides for Antisensen Experiments", *Glen Research Report*, vol. 10, 3 (Dec. 1997 issue).
Anonymous. "Cytofectin GSV Transfection Protocol", *Glen Research Report*, vol. 10, 4-6 (Dec. 1997 issue).
Anonymous. "New Fluorescent Reagents—Tamra CPG, Fluorescein-dt", *Glen Research Report*, vol. 10, 7 (Dec. 1997 issue).
Anonymous. "Universal Support Replaces Individual Columns", *Glen Research Report*, vol. 10, 8 (Dec. 1997 issue).
Anonymous. "Q-Supports Reduce Cleavage Time to 2 Minutes", *Glen Research Report*, vol. 10, 9 (Dec. 1997 issue).
Anonymous. "5,6-Dihydro-Pyrimidines, 2'-Phosphoramidites", *Glen Research Report*, vol. 10, 11 (Dec. 1997 issue).
Anonymous. "Non-enzymatic Ligation of Single-Stranded and Duplex DNA", *Glen Research Report*, vol. 10, 12 (Dec. 1997 issue).
Anonymous. "More Novel Monomers -4-Thio-dU, 5'-Amino-dT, 2'-F-Pyrimidines", *Glen Research Report*, vol. 10, 10 (Dec. 1997 issue).
Barany, F. "The ligase chain reaction in a PCR world", Genome Res. vol. 1, 5-16 (1991).
Barany, F. "The Taql star reaction: strand preferences reveal hydrogen-bond donor and acceptor sites in canonical sequence recognition", Gene vol. 65 149-165 (1988).
Bayer, E. et al. "Liquid Phase Synthesis of Peptides", Nature vol. 237; 30 (Jun. 1972).
Bittker, et al. "Nucleic Acid Evolution and Minimization by Nonhomologous Random Recombination", Nature Biotechnology 20, 1024-1029 (2002).
Bonora, et al. "Large Scale, PEG-supported DNA Synthesis"; Nucleosides & Nucleotides, 10 (1-3), (1991).
Brennan, et al. "Using T4 RNA Ligase with DNA Substrates", Methods in enzymology, vol. 100, pp. 38-52.
Broude, Natalie E. "Stem-loop oligonucleotides: a robust tool for molecule biology and biotechnology", Trends in Biotechnology, vol. 20, No. 6, Jun. 2002 (22-06) pp. 249-256.
Buller, F. et al., "Design and synthesis of a novel DNA-encoded chemical library using Diels-Alder cycloadditions", Bioorg Med Chem Lett 18, 5926 (2008).
Buller, F. et al. "Discovery of TNF inhibitors from an DNA-encoded chemical library based on Diels-Alder cycloaddition", Chem Biol 16, 1075 (2009).
Bunin et al., "[26] Synthesis and Evaluation of 1, 4-Benzodiazepine Libraries," Mthods in Enzymology, vol. 267, pp. 448-465, (1996).
Bunin, et al. "The combinatorial synthesis and chemical and biological evaluation of a 1,4-benzodiazepine library",*Proc. Natl. Acad. Sci. USA*, vol. 91, pp. 4708-4712 (May 1994).
Buskirk, et al. "Engineering a Ligand-Dependent RNA Transcriptional Activator", Chem. Biol. 11, 1157-1163 (2004), This work is featured in a Research Highlight in Nature Methods 1, 6-7 (2004).
Chu et al. "Ligation of oligonucleotides to nucleic acids or proteins via disulfide bonds." Nucleic Acids Research. vol. 16. No. 9. pp. 3671-3691 (1998).
Clark et al. "Design, synthesis and selection of DNA-encoded small-molecule libraries", Nat Chem Biol 5, 647 (2009).
Clark, Matthew A. "Selecting chemicals: the emerging utility of DNA-encoded libraries", Molecular Discovery Research, GlaxoSmithKline, Waltham, MA, USA. Current Opinion in Chemical Biology (2010), 14(3), 396-403. Publisher: Elsevier B.V.
Colombo, R. et al. "Synthesis of leucin-enkephalin and methionineenkephalin . . . ", Hoppe-Seyler's Z.Physiol.Chem. vol. 363 (1981).
Cotton, et al. "Reactivity of cytosine and thymine in single-base-pair mismatches with hydroxylamine and osmium tetroxide and its application to the study of mutations", Proc Natl Acad Sci (US), 85, 4397-401 (1988).
Constantino, L et al. "Privileged structures as leads in medicinal chemistry", Curr Med Chem 13, 65, (2006).

(56) References Cited

OTHER PUBLICATIONS

Czarnik, A. W. "Encoding strategies in combinatorial chemistry", Proc. Natl. Acad. Sci. USA, vol. 94, pp. 12738-12739 (Nov. 1997).
Denapoli, et al. "PEG-supported Synthesis of Cyclic Oligodeoxyribonucleotides", Nucleosides & Nucleotides, vol. 12, No. 1 (1993).
Douglas, et al. "Polymer-supported solution synthesis of oligosaccharides", J. Am. Chem. Soc., vol. 113 (1991).
Ecker, David J, et al. "Rational screening of oligonucleotide combinatorial libraries for drug discovery", Nucleic Acids Research, vol. 21, No. 8, pp. 1853-1856 (1993).
Fack, Fred, et al. "Heteroduplex mobility assay (HMA) pre-screening: An improved strategy for the rapid identification of inserts selected from phage-displayed peptide libraries", Molecular Diversity, vol. 5, No. 1; pp. 7-12 (2000).
Fegan et al. "Rigid cyanine dye nucleic acid labels", Chem Commun May 7; (17) 2004-6 (2008).
Gorin, et al. "Reactivity-Dependent PCR: Direct, Solution-Phase in Vitro Selection for Bond Formation", J. Am. Chem. Soc. 131, pp. 9189-9191 (2009).
Grange, et al. "Detection of point mutations in type I collagen by RNase digestion of RNA/RNA hybrids", Nucleic Acids Research 18: 4227-36 (1990).
Gruen, et al. "An In Vivo Selection System for Homing Endonuclease Activity", Nucleic Acids Research 30, e29 (2002).
Guo, T. et al. "Preparation of Encoded Combinatorial Libraries for Drug Discovery", Methods in Molecular Biology, Combinatorial Library Methods and Protocols, pp. 23-39 (2002).
Hansen, M. "A Yoctoliter-scale DNA reactor for small-molecule evolution", J Am Chem Soc. 131, 1322 (2009).
Harada, et al. "In Vitro selection of optimal DNA substrates for t4 RNA ligase", Proc. Natl. Acad. Sci. USA, vol. 90, pp. 1576-1579 (Feb. 1993).
Higgins, et al. "Addition of Oligonucleotides to the 5'-Terminus of DNA by T4 RNA Ligase", Nucleic Acids Research, 6(3): 1013-1024 (1979).
Higgins, et al. "DNA-joining Enzymes: A Review", Methods in Enzymology, vol. 68, pp. 50-71 (1979).
Hinton, et al. "T4 RNA Ligase Joins 2'-Deoxyribonucleoside 3', 5'-Bisphosphates to Oligodeoxyribonucleotides", Biochemistry vol. 17, No. 24, pp. 5091-5097 (1978).
Holmes, CP "Model Studies for New o-Nitrobenzyl Photolabile Linkers: Substituent Effects on the Rates of Photochemical Cleavage", J. Org. Chem. 62, 2370-2380 (1997).
Housby, Nicholas J, et al. "Fidelity of DNA ligation: a novel experimental approach based on the polymerisation of libraries of oligonucleotides", Nucleic Acids Research, vol. 26, No. 18, pp. 4259-4266 (1998).
Hsu "Detection of DNA point mutations with DNA mismatch repair enzymes" *Carcinogenesis* 15:1657-62 (1994).
Ito et al. Tag-reporter and Resin Capture ± Release Strategy in Oligosaccharide Synthesis. Chemistry—A European Journal 8(14):3077-3084 (2002).
James, Kenneth D. et al. "The Fidelity of Template-Directed Oligonucleotide Ligation and the Inevitability of Polymerase Function", Origins of Life and Evolution of the Biosphere 29, 1999 *Kluwer Academic Publishers*; pp. 375-390.
Janda, Kim D. "Tagged versus untagged libraries: Methods for the generation and screening of combinatorial chemical libraries", *Proc. Natl. Acad. Sci. USA*, vol. 91, pp. 10779-10785 (Nov. 1994).
Jäschke, et al. "Synthesis and properties of oligodeoxyribonucleotide—polyethylene glycol conjugates", *Nucleic Acids Research*, vol. 22, No. 22, pp. 4810-4817 (1994).
Kanagawa, Takahiro Bias and Artifacts in Multitemplate Polymerase Chain Reactions (PCR), Journal of Bioscience and Bioengineering, vol. 96, No. 4, pp. 317-323 (2003).
Kanan, et al. "Reaction Discovery Enabled by DNA-Templated Synthesis and in Vitro Selection", Supplementary Information, pp. 1-20.

Kinoshita, Y. et al. "Strand ligation in a double-stranded DNA by T4 RNA ligase", Department of Functional Materials Science, Saitama University, Urawa, Japan. Chemistry Letters (9), 797-798 (1996).
Krug, et al. "Reversal of T4 RNA Ligase", Biochemistry vol. 21, No. 8, pp. 1858-1864 (1982).
Kurz, M. et al. "cDNA—protein fusions: covalent protein—gene conjugates for the in vitro selection of peptides and proteins", Chembiochem—A European Journal of Chemical Biology, Wiley VCH, Weinheim, DE, vol. 2, No. 9, Sep. 3, 2001, pp. 666-672, XP002332971, ISSN: 1439-4227.
Lebl, Michal "Parallel Personal Comments on "Classical" Papers in Combinatorial Chemistry", J. Comb. Chem. 1, pp. 3-24 (1999).
"Ligase", Answers.com: http://www.answers.com/topic/ligase, [accessed Dec. 10, 2009].
Lim, Carols S. et al. "Syntehsis of DNA Dumbbells: Chemical vs. Enzymatic Ligation of Self-Complementary Oligonucleotides", Abstract only, Nucleotides and Nucleic Acids; vol. 16, Issue 1 & 2; pp. 41-51 (Jan. 1997).
Liu, D.R. "Development of Amplifiable and Evolvable Unnatural Molecules", website of Dr. D. R. Liu, publicly available Mar. 11, 2000. http://web.archive.org/web/20000311112631/http://evolve.havard.edu.
Liu, D.R. "The Chemistry and Chemical Biology of Molecular Evolution," website of Dr. D.R. Liu, publicly available Mar. 1, 2001. http://web.archive.org/web/20010301175107/http://evolve.havard edu.
Liu, D.R. "The Chemistry and Chemical Biology of Molecular Evolution," website of Dr. D.R. Liu, publicly available Oct. 15, 2003. http://web.archive.org/web/20031216020734/http://evolve.havard edu.
Liu, D.R. "The Chemistry and Chemical Biology of Molecular Evolution," website of Dr. D.R. Liu, publicly available Nov. 20, 2002. http://web.archive.org/web/20021129131743/http://evolve.havard edu.
Liu, D.R. "The Chemistry of Molecular Evolution," website of Dr. D.R. Liu, publicly available Oct. 15, 2000. http://web.archive.org/web/20001015144553/http://evolve.havard.edu.
Liu, W, et al. "Denaturing high performance liquid chromatography (DHPLC) used in the detection of germline and somatic mutations". Nucleic Acids Research. vol. 26. pp. 1396-1400 (1998).
Liu, D.R. "The Chemistry and Chemical Biology of molecular Evolution", Liu Group Research Summary from the website of Professor David R. Liu, obtained from the website in Feb. 2005.
Lobanov Trends in Biotechnology, vol. 20, No. 2, pp. 86-87 (Feb. 2002).
Lockhart, et al. "Expression monitoring by hybridization to high-density oligonucleotide arrays", Bio/Technology, Nature publishing co., New York, US, vol. 14, No. 13, p. 1675-1680 (Dec. 1, 1996).
Luebke, Kevin J. et al. "Nonenzymatic ligation of double-helical DNA by alternate-strand triple helix formation"; Nucleic Acids Research; vol. 20, No. 12; pp. 3005-3009 (1992).
MacLean, Derek, et al. "Encoded Combinatorial Chemistry: Synthesis and screening of a library of highly functionalized pyrrolidines", Proc. Natl. Acad. Sci. USA, vol. 94, pp. 2805-2810 (Apr. 1997).
Makara, Gergely M. et al. "Improving Success rates for lead generation using affinity binding technologies", Current Opinion in Biotechnology 16:666-673 (2005).
Magliery, et al. "Expanding the Genetic Code in Vitro and in Vivo", The Genetic Code and the Origin of Life, Ed. Ribas de Pouplana, L. Landes Bioscience, in Press (2004).
Mannocci, L. "DNA-Encoded affinity maturation libraries", Proc Natl Acad Sci USA 105, 17670 (2008).
Mannocci, Lucca "DNA-Encoded Chemical Libraries", Diss. ETH No. 18153 (2009).
Margulies, M. et al., "Genome sequencing in microfabricated high-density picolitre reactors", Nature 437, 376 (2005).
Mashal, et al. "Detection of mutations by cleavage of DNA heteroduplexes with bacteriophage resolvases", Nature Genetics 9:177-83 (1995).
Matsuda, et al. "Low Fidelity DNA Synthesis by Human DNA Polymerase-?", Nature, 404: 1011-1013 (Apr. 27, 2000).
Matsuura, K., et al. "Construction of glyco-clusters by self-organization of site-specifically glycosylated oligonucleotides and their

(56) References Cited

OTHER PUBLICATIONS cooperative amplification of lectin-recognition." Journal of the American Chemical Society, vol. 123, No. 2, pp. 357-358 (Jan. 17, 2001).
McCoy, et al. "T4 Ribonucleic Acid Ligase Joins Single-Strand Oligo(deoxyribonucleotides)", Biochemistry vol. 19, No. 4, 635-642 (1980).
McGregor, et al. "Interaction-Dependent PCR: Identification of Ligand-Target Pairs from Libraries of Ligands and Libraries of Targets in a Single Solution-Phase Experiment", J. Am. Chem. Soc. 132, pp. 15522-15524 (2010).
Mendel, D. "Site-directed mutagenesis with an expanded genetic code." Annu. Rev. Biophys. Biomol. Struc. vol. 24, pp. 435-462. (1995).
Miller, Scott J. "DNA as a template for reaction discovery", Nature Biotechnology, vol. 22, No. 11, pp. 1378-1379 (Nov. 2004).
Mudrakovskaya, et al. "Solid-Phase Enzymatic Synthesis of Oligoribonucleotides", Bioorg Khim vol. 17, No. 6, pp. 469-472 (1991).
Mutter, M. et al. "Functionalized polyethylene glycols and polypeptides in organic synthesis and catalysis", Reactive Polymers, vol. 6, pp. 99-107 (1987).
Myers, et al. "Detection of single base substitutions by ribonuclease cleavage at mismatches in RNA:DNA duplexes" *Science* 230: 1242-6 (1985).
Nielsen "Combinatorial chemistry and automation", DDT, vol. 1, No. 11, pp. 458-460 (Nov. 1996).
Nishigaki, Koichi, et al. "Y-ligation: an efficient method for ligating single stranded DNAs and RNAs with T4 RNA ligase", Department of Functional Materials Science, Saitama University, Urawa, Japan. *Molecular Diversity* vol. 4(3), 187-190 (2000).
O'Donovan MC, et al. "Blind analysis of denaturing high-perfomance liquid chromatography as a tool for mutation detection", Genomics. 52:4449 (1998).
"Organic Chemistry", Wikipedia, [accessed Dec. 10, 2009]: http://en.wikipedia.org/wiki/organic_chemistry (10 pages).
"Orthogonal Protection Protecting Group", Wikipedia: http://en.Wikipedia.org/wiki/protecting_group#Orthogonal_protection [accessed Apr. 15, 2010].
Persichetti, et al. "Cross-Linked Enzyme Crystals (CLECs) of Thermolysin in the Synthesis of Peptides", Journal of the American Chemical Society, 117: 2732-2737 (1995).
Pochet, et al. "Solid-Supported Ligation Primer", Nucleic Acids Research, 16(4): 1619 (1988).
Polsky-Cynkin et al. "Use of DNA immobilized on platic and agarose supports to detect DNA by sandwich hybridization", Clin. Chem. 31(9): 1438-43 (Sep. 1985).
Porco, Jr. "Synthesis Undressed", Nature 446, 383-5 (Mar. 22, 2007).
Robinson "A Synthesis of Tropinone", Journal of the Chemical Society Transactions, vol. 111, pp. 762-768, (1917).
Romaniuk, et al. "Joining of RNA molecules with RNA ligase", Methods in Enzymology, vol. 100, pp. 52-59, (1983).
Saiki et al. "Genetic analysis of amplified DNA with immobilized sequence-specific oligonucleotide probes" *PNAS* 86(16): 6230-6234 (1989).
Sarmento, et al. "Cardosins A and B, Two New Enzymes Available for Peptide Synthesis", *Journal of Molecular Catalysis B: Enzymatic*, 5: 327-330 (1998).
Scheuermann, Jörg, et al. "DNA-encoded chemical libraries: A tool for drug discovery and for chemical biology", ChemBioChem 0000, 00, 1-8 (2010).
Schmidt, JG, et al., "Information transfer from peptide nucleic acids to RNA by template-directed syntheses", *Nucleic Acids Res.*, vol. 25 (23), pp. 4792-4796 (Dec. 1, 1997).
Schmitz, et al. "Solid-Phase Enzymatic Synthesis of Oligonucleotides", Organic Letters, 1(11): 1729-1731 (1999).
Schoenleber, R.O. et al. "Photochemical release of amines by C,N-bond cleavage", Synlett 501-504 (2003).
Schultz, et al. The Combinatorial Library: A Multifunctional Resource, Biotechnol. Prog. 12, 729-743 (1996).
Shabarova, et al. "Chemical ligation of DNA: the first non-enzymatic assembly of a biologically active gene", Nucl. Acids Res., 19:4247-51 (1991).
Sharifian, Hoda. "Errors induced during PCR amplification", May 30, 2010.
Snyder, T. "Ordered multistep synthesis in a single solution directed by DNA templates", Angew Chem Int Ed Engl 44, 7379 (2005).
Still, W. Clark "Career-In-Review (CIR)", BJ Wright, Synthesis Literacy Group, Columbia University Chemistry, Mar. 30, 2007.
Takemori, Shigeki, et al. "Stabilization of Enzyme Activity by an Organic Solvent", Abstract only, Nature 215, 417-419 (Jul. 22, 1967).
Tan et al. "Natural-product inhibitors of human DNA ligase I", Biochemical Journal 314: 993-1000 (1996).
Tan, Derek S. et al. "Ligand discovery using encoded combinatorial libraries", Current Opinion in Drug Discovery & Development, 3(4), p. 439-53 (Jul. 2000).
Tessier, et al. "Ligation of Single-Stranded Oligodeoxyribonucleotides by T4 RNA Ligase", Analytical Biochemistry 158, 171-178 (1986).
Tse, B. "Translation of DNA into a library of 13,000 synthetic small-molecule macrocycles suitable for in vitro selection", J Am Chem Soc 130, 15611 (2008).
Unknown "Science & Technology: Concentrates", *Chem. & Eng. News* 82 [40] 31 (2004).
Uhlenbeck, et al. "T4 RNA Ligase", The Enzymes, vol. XV, pp. 31-58 (1982).
Vágner, et al. "Enzyme-mediated spatial segregation on individual polymeric support beads: Application to generation and screening of encoded combinatorial libraries", *Proc. Natl. Acad. Sci. USA*, vol. 93, pp. 8194-8199, (Aug. 1996).
Vaisman, et al. "Human DNA polymerase, promiscuous mismatch extension", JBC 276: 30615-30622 (2001).
Vratskikh, et al. "Solid-phase synthesis of oligoribonucleotides using T4 RNA ligase and T4 polynucleotide kinase", *Biochimie* 77, 227-232 (1995).
Wagner, et al. "Mutation detection using immobilized mismatch binding protein (MutS)" *Nucleic Acids Research* 22, 3944-3948 (1995).
Walder, JA., et al. "Complementary carrier Peptide Synthesis: General Strategy and Implications for Prebiotic Origin of Peptide Synthesis", *Department of Chemistry, and Department of Biochemistry and Molecular Biology, Northwestern University*, Evanston, Illinois 60201, vol. 76, No. 1, p. 51-55, (1979).
Washington, et al. "Mismatch extension ability of yeast and human DNA polymerase n", JBC 276: 2263-2266 (2001).
Whitesides, et al. "Enzymes as Catalysts in Organic Synthesis", *Aldrichimica Acta.*, vol. 16, No. 2, pp. 27-31, (1983).
Winzeler, et al. "Fluorescence-based expression monitoring using microarrays", *Methods Enzymol*. 306: 3-18 (1999).
Xu, Y, et al. "High sequence fidelity in a non-enzymatic DNA autoligation reaction", Nucleic Acids Research, vol. 27, No. 3; pp. 875-881 (1999).
Zhu, et al. A Primer-dependent Polymerase Function of Pseudomonas aeruginosa ATP-dependent DNA ligase (LigD). Journal of Biological Chemistry 280(1): 418-427 (2005).
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Feb. 8, 2003.
Website of prof. David R. Liu, publicly available Feb. 10, 2004.
Website of prof. David R. Liu, publicly available Feb. 15, 2001.
Website of prof. David R. Liu, publicly available Dec. 16, 2003.
Website of prof. David R. Liu, publicly available Jun. 4, 2002.
Website of prof. David R. Liu, publicly available Jun. 6, 2003.
Website of prof. David R. Liu, publicly available Mar. 27, 2003.
Website of prof. David R. Liu, publicly available Mar. 31, 2001.
Website of prof. David R. Liu, publicly available Nov. 29, 2002.
Website of prof. David R. Liu, publicly available Nov. 30, 2001.
Website of prof. David R. Liu, publicly available Oct. 17, 2002.
Decision to Grant from European Application No. EP 02740409.4 dated Jul. 26, 2007.
European Office Action from European Application No. EP 02740409.4 dated Sep. 1, 2005.

(56) References Cited

OTHER PUBLICATIONS

Reply to European Office Action from European Application No. EP 02740409.4 dated Jun. 16, 2006.
Intent to Grant from European Application No. EP 02740409.4 printed Oct. 13, 2006.
Extended European Search Report from European Application No. 07114663.3 dated May 25, 2009.
Extended European Search Report from European Application No. 10 18 4311 dated Feb. 28, 2011.
International Preliminary Examination Report from PCT No. PCT/DK02/00419 dated Jan. 28, 2004.
International Search Report from PCT No. PCT/DK02/00419 dated Jun. 25, 2003.
Restriction Requirement from U.S. Appl. No. 10/175,539 mailed Apr. 6, 2005.
Response to Restriction Requirement from U.S. Appl. No. 10/175,539 mailed May 6, 2005.
Office Action (Non-Final Rejection) from U.S. Appl. No. 10/175,539 mailed May 13, 2005.
Response to Office Action (Non-Final Rejection) from U.S. Appl. No. 10/175,539 mailed Apr. 13, 2006.
Office Action (Non-Final Rejection) from U.S. Appl. No. 10/175,539 mailed May 14, 2007.
Response to Office Action (Non-Final Rejection) from U.S. Appl. No. 10/175,539 mailed Sep. 13, 2007.
Office Action (Final Rejection) from U.S. Appl. No. 10/175,539 mailed May 19, 2006.
Notice of Appeal from U.S. Appl. No. 10/175,539 dated Nov. 20, 2006.
Request for Continued Examination from U.S. Appl. No. 10/175,539 dated Feb. 20, 2007.
Office Action (Ex Parte Quayle Action) from U.S. Appl. No. 10/175,539 mailed Nov. 27, 2007.
Response to Ex Parte Quayle Action from U.S. Appl. No. 10/175,539, filed Feb. 27, 2008.
Notice of Allowance from U.S. Appl. No. 10/175,539 mailed May 30, 2008.
Issue Notification U.S. Appl. No. 10/175,539 issued Jun. 1, 2010.
Office Action (Non-Final Rejection) from U.S. Appl. No. 12/330,709 mailed Oct. 27, 2009.
Response to Office Action (Non-Final Rejection) from U.S. Appl. No. 12/330,709, filed Apr. 21, 2010.
Notice of Allowance from U.S. Appl. No. 12/330,709 mailed Mar. 3, 2011.
Request for Continued Examination and supplemental IDS from U.S. Appl. No. 12/330,709, filed Jun. 2, 2011.
Office Action from European Application No. 03709676.5 dated Feb. 23, 2005.
Reply to 1st Office Action from European Application No. 03709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 10, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 mailed Apr. 13, 2010.
1st Office Action from European Application No. 08169346.7 mailed Apr. 19, 2011.
Response filed in European Application No. 08169346.7 mailed Mar. 23, 2011.
International Search Report for PCT Application No. PCT/DK03/00172 mailed Nov. 3, 2003.
Office Action (Non-Final) for U.S. Appl. No. 10/507,121 mailed Feb. 8, 2007.
Response to Office Action for U.S. Appl. No. 10/507,121 mailed Jun. 7, 2007.
Office Action (Final Rejection) for U.S. Appl. No. 10/507,121 mailed Sep. 7, 2007.
Request for Continued Examination and supplemental amendment for U.S. Appl. No. 10/507,121, filed Feb. 13, 2008.
Notice of Allowance for U.S. Appl. No. 10/507,121 mailed Mar. 20, 2008.
Issue Notification for U.S. Appl. No. 10/507,121 mailed Jul. 30, 2008.
Office Action (Non-Final) from U.S. Appl. No. 12/179,323 mailed Jan. 27, 2010.
Response to Office Action from U.S. Appl. No. 12/179,323, filed Jun. 24, 2010.
Office Action (Final Rejection) for U.S. Appl. No. 12/179,323 mailed Sep. 15, 2010.
Notice of Appeal from U.S. Appl. No. 12/179,323, filed Mar. 15, 2011.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report from PCT Application No. PCT/DK03/00516 mailed Feb. 18, 2004.
1st Restriction Requirement from U.S. Appl. No. 10/523,006 mailed Apr. 4, 2008.
Response to 1st Restriction Requirement from U.S. Appl. No. 10/523,006, filed Oct. 1, 2008.
2nd Restriction Requirement from U.S. Appl. No. 10/523,006 mailed Dec. 9, 2009.
Response to 2nd Restriction Requirement from U.S. Appl. No. 10/523,006, filed May 5, 2010.
3rd Restriction Requirement from U.S. Appl. No. 10/523,006 mailed Aug. 3, 2010.
Response to 3rd Restriction Requirement from U.S. Appl. No. 10/523,006, filed Feb. 1, 2011.
Office Action (Non-Final) from U.S. Appl. No. 10/523,006 mailed Mar. 16, 2011.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00921 Jun. 22, 2004.
Restriction Requirement for U.S. Appl. No. 10/539,288 mailed Aug. 2, 2010.

(56) References Cited

OTHER PUBLICATIONS

Response to Restriction Requirement for U.S. Appl. No. 10/539,288, filed Jan. 31, 2011.
Office Action (Non-Final) for U.S. Appl. No. 10/539,288 mailed Apr. 25, 2011.
1st Office Action for European Application No. 03729906.6 mailed May 17, 2006.
Reply to 1st Office Action for European Application No. 03729906.6 mailed Mar. 9, 2007.
2nd Office Action for European Application No. 03729906.6 mailed Sep. 22, 2009.
Reply to 2nd Office Action for European Application No. 03729906.6 mailed May 6, 2010.
International Search Report for PCT Application No. PCT/DK03/00417 mailed Feb. 10, 2004.
Restriction Requirement for U.S. Appl. No. 10/518,056 mailed Jan. 4, 2008.
Response to Restriction Requirement for U.S. Appl. No. 10/518,056, filed Jun. 2, 2008.
Office Action (Non-Final) for U.S. Appl. No. 10/518,056 mailed Oct. 8, 2008.
Reply to Office Action for U.S. Appl. No. 10/518,056, filed Feb. 17, 2009.
Office Action (Final Rejection) for U.S. Appl. No. 10/518,056 mailed May 27, 2009.
Notice of Appeal for U.S. Appl. No. 10/518,056 mailed Oct. 27, 2009.
Amendment After Appeal for U.S. Appl. No. 10/518,056, filed Nov. 17, 2009.
Advisory Action for U.S. Appl. No. 10/518,056 mailed Jan. 7, 2010.
Request for Continued Examination and IDS for U.S. Appl. No. 10/518,056, filed Mar. 22, 2010.
1st Office Action for European Application No. 04713515.7 mailed Oct. 19, 2006.
Reply to 1st Office Action for European Application No. 04713515.7 mailed Aug. 20, 2007.
2nd Office Action for European Application No. 04713515.7 mailed Mar. 31, 2008.
Reply to 2nd Office Action for European Application No. 04713515.7 mailed Dec. 5, 2008.
3rd Office Action for European Application No. 04713515.7 mailed Sep. 6, 2010.
Reply to 3rd Office Action for European Application No. 04713515.7 mailed Jun. 21, 2011.
International Search Report for PCT Application No. PCT/DK2004/000116 mailed Aug. 23, 2004.
Office Action (Non-Final) for U.S. Appl. No. 10/545,795 mailed Mar. 31, 2008.
Response filed for U.S. Appl. No. 10/545,795, filed Sep. 30, 2008.
Office Action for U.S. Appl. No. 10/545,795 mailed Jan. 27, 2009.
Notice of Appeal filed for U.S. Appl. No. 10/545,795, filed Jul. 27, 2009.
Amendment after Appeal for U.S. Appl. No. 10/545,795, filed Sep. 28, 2009.
Office Action (Advisory Action) for U.S. Appl. No. 10/545,795 mailed Sep. 29, 2009.
Request for Continued Examination and IDS for U.S. Appl. No. 10/545,795, filed Oct. 27, 2009.
Office Action (Non-Final) for U.S. Appl. No. 10/545,795 mailed Nov. 16, 2009.
Office Action (Non-Final) for U.S. Appl. No. 10/545,795 mailed Mar. 30, 2010.
Office Action (Interview Summary) for U.S. Appl. No. 10/545,795 mailed Jul. 30, 2010.
Response filed for U.S. Appl. No. 10/545,795, filed Aug. 30, 2010.
Office Action (Final rejection) for U.S. Appl. No. 10/545,795 mailed Feb. 1, 2011.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/DK2004/000117 mailed Aug. 19, 2004.
Restriction Requirement for U.S. Appl. No. 10/546,538 mailed Jul. 31, 2008.
Response to Restriction Requirement for U.S. Appl. No. 10/546,538, filed Dec. 24, 2008.
Office Action (Non-Final) for U.S. Appl. No. 10/546,538 mailed Jun. 10, 2009.
Response to Office Action for U.S. Appl. No. 10/546,538, filed Dec. 9, 2009.
Office Action (Final Rejection) for U.S. Appl. No. 10/546,538 mailed Jun. 8, 2010.
Response to Office Action (Notice of Appeal) for U.S. Appl. No. 10/546,538, filed Dec. 8, 2010.
Office Action (Communication re: Appeal) for U.S. Appl. No. 10/546,538 mailed Jul. 20, 2011.
1st Office Action for European Application No. 04722237.7 dated Mar. 2, 2006.
Reply to 1st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 mailed Sep. 15, 2010.
International Search Report for International Application No. PCT/DK2004/000195 mailed Dec. 27, 2004.
Restriction Requirement for U.S. Appl. No. 10/549,619 mailed Apr. 21, 2008.
Response to Restriction Requirement for U.S. Appl. No. 10/549,619, filed Sep. 22, 2008.
Office Action (Non-Final) for U.S. Appl. No. 10/549,619 mailed Apr. 28, 2009.
Response to Office Action for U.S. Appl. No. 10/549,619, filed Oct. 26, 2009.
Office Action (Interview Summary) for U.S. Appl. No. 10/549,619 mailed Mar. 3, 2010.
Amendment filed for U.S. Appl. No. 10/549,619, filed Oct. 21, 2010.
Notice of Allowance for U.S. Appl. No. 10/549,619 mailed Jul. 7, 2010.
Amendment After Allowance for U.S. Appl. No. 10/549,619, filed Oct. 6, 2010.
Issue Notification for U.S. Appl. No. 10/549,619 mailed Mar. 9, 2011.
Australian Application No. 2003273792.
Examination Report for Australian Application No. 2003273792 dated May 6, 2011.
Reply to 1st Office Action for European Application No. 03757752.5 dated Jan. 12, 2006.
Amendment after ESP for European Application No. 03757752.5 dated Feb. 14, 2006.
1st Office Action for European Application No. 03757752.5 dated Mar. 16, 2006.
2nd Office Action for European Application No. 03757752.5 dated Feb. 15, 2007.
Reply to 2nd Office Action for European Application No. 03757752.5 dated Aug. 15, 2007.

(56) References Cited

OTHER PUBLICATIONS

Summons for European Application No. 03757752.5 dated Aug. 11, 2008.
Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
International Search Report for International Application No. PCT/DK03/00739 mailed Aug. 30, 2004.
Restriction Requirement for U.S. Appl. No. 10/525,817 mailed May 9, 2007.
Response to Restriction Requirement for U.S. Appl. No. 10/525,817, filed Sep. 10, 2007.
Restriction Requirement for U.S. Appl. No. 10/525,817 mailed Nov. 28, 2007.
Response to Restriction Requirement for U.S. Appl. No. 10/525,817, filed Feb. 28, 2008.
Restriction Requirement for U.S. Appl. No. 10/525,817 mailed Jul. 7, 2009.
Response to Restriction Requirement for U.S. Appl. No. 10/525,817, filed Oct. 5, 2009.
Office Action (Non-Final) for U.S. Appl. No. 10/525,817 mailed Apr. 1, 2010.
Supplemental Office Action for U.S. Appl. No. 10/525,817 mailed Apr. 5, 2010.
Response filed for U.S. Appl. No. 10/525,817, filed Jul. 27, 2010.
Office Action (Non-Final) for U.S. Appl. No. 10/525,817 mailed Jan. 5, 2011.
Office Action (Interview Summary) for U.S. Appl. No. 10/525,817 mailed Jul. 1, 2011.
Response filed for U.S. Appl. No. 10/525,817, filed Jul. 5, 2011.
Restriction Requirement for U.S. Appl. No. 11/402,957 mailed Jun. 25, 2008.
Response to Restriction Requirement for U.S. Appl. No. 11/402,957, filed Aug. 25, 2008.
Office Action (Non-Final) for U.S. Appl. No. 11/402,957 mailed Nov. 28, 2008.
Response filed for U.S. Appl. No. 11/402,957, filed May 15, 2009.
Office Action (Non-Final) for U.S. Appl. No. 11/402,957 mailed Jul. 6, 2009.
Response filed for U.S. Appl. No. 11/402,957, filed Dec. 7, 2009.
Office Action (Final Rejection) for U.S. Appl. No. 11/402,957 mailed Feb. 16, 2010.
Response filed for U.S. Appl. No. 11/402,957, filed Jul. 28, 2010.
Notice of Appeal filed for U.S. Appl. No. 11/402,957, filed Aug. 16, 2010.
Notice of Allowance for U.S. Appl. No. 11/402,957 mailed Sep. 2, 2010.
Request for Continued Examination filed for U.S. Appl. No. 11/402,957, filed Dec. 2, 2010.
Second Notice of Allowance for U.S. Appl. No. 11/402,957 mailed Apr. 29, 2011.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Decision to Grant for European Application No. 04762850.8 dated Oct. 8, 2009.
Amendment after Grant for European Application No. 04762850.8 dated Jul. 17, 2009.
International Search Report for PCT/DK2004/000630 mailed Feb. 14, 2005.
Restriction Requirement for U.S. Appl. No. 10/572,644 dated Feb. 4, 2009.
Response to Restriction Requirement for U.S. Appl. No. 10/572,644 dated Jul. 29, 2009.
Restriction Requirement for U.S. Appl. No. 10/572,644 dated Jul. 21, 2010.
Response to Restriction Requirement for U.S. Appl. No. 10/572,644, filed Jan. 19, 2011.
Office Action (Non-Final) for U.S. Appl. No. 10/572,644 dated Oct. 29, 2009.
Response to Office Action for U.S. Appl. No. 10/572,644, filed Apr. 28, 2010.
Office Action (Non-Final) for U.S. Appl. No. 10/572,644 dated Mar. 31, 2011.
1st Office Action for European Application No. 05715120.1 dated Apr. 12, 2007.
Reply to 1st Office Action for European Application No. 05715120.1 dated Feb. 1, 2008.
International Search Report for International Application No. PCT/DK2006/000685 mailed Jun. 14, 2007.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
International Search Report for International Application No. PCT/DK2009/050129 mailed Aug. 21, 2009.
Annex I: Vipergen Technology Paper—The YoctoReactor drug discovery technology platform. 2 pages.
Annex II: Vipergen Technology Paper—The YoctoReactor drug discovery technology platform. 2 pages. Aug. 2008.
Communication re partial European Search Report in European application No. 10184069.2, dated Feb. 10, 2012.
Partial European Search Report in European application No. 10184069.2, dated Feb. 10, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6, dated Oct. 7, 2011.
Response to Partial European Search Report in European application No. 10192717.6, dated Dec. 8, 2011.
European Search Report in European application No. 10192717.6, dated Jan. 25, 2012.
European Search Opinion in European application No. 10192717.6, dated Jan. 25, 2012.
International Search Report in PCT/DK2011/000031, dated Aug. 23, 2011.
Annex I: Vipergen Technology Paper—The YoctoReactor drug discovery technology platform. 2 pages.—No Date.
Australian Patents Act 1990-Sectino 32 Regulation 3.6, (Request for a Determination of Dispute between Applicants) and 3.7 Application to Commissioner for Declaration of an Eligible Person.—No Date.
Opposition against EP 1558744 filed by Strawman Limited on Mar. 12, 2012.
Opposition against EP 1558744 filed by HGF on Mar. 14, 2012.

(56) References Cited

OTHER PUBLICATIONS

Millward, S.W. et al. "A General Route for Post-Translational Cyclization of mRNA Display Libraries", *Journal of the American Chemical Society*: vol. 127, 14142-14143, (2005).
Millward, S.W. et al. "Design of Cyclic Peptides That Bind Protein Surfaces with Antibody-Like Affinity", *ACS Chemical Biology*: vol. 2, No. 9, 625-634, (2007).
Giebel, L.B. et al. "Screening of Cyclic Peptide Phage Libraries Identifies Ligands That Bind Streptavidin with High Affinities", *Biochemistry*: vol. 34, No. 47; 15430-15435, (1995).
Ladner, R.C. "Constrained peptides as binding entities", *Elsevier Science Ltd., Trends in Biotechnology*: vol. 13, 426-430, (1995).
Koivunen, E. et al. "Phage Libraries Displaying Cyclic Peptides with Different Ring Sizes: Ligand Specificities of the RGD-Directed Integrins", *Bio/Technology*: vol. 13, 265-270, (1995).
Office Action in European patent application No. 10184311.8, dated Mar. 19, 2012, with Annex.
Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.
Office Action of Jan. 29, 2013 for Japanese patent application No. 2010-226107.
1st Restriction requirement of Oct. 5, 2011 for U.S. Appl. No. 12/095,778.
2nd Restriction requirement of Jun. 2012 for U.S. Appl. No. 12/095,778.
Examiner's amendment communication dated May 12, 2011 for U.S. Appl. No. 10/525,817.
Fiinal rejection dated Jan. 9, 2012 for U.S. Appl. No. 10/572,644.
Final rejection dated Feb. 6, 2012 for U.S. Appl. No. 10/523,006.
Final rejection of Dec. 22, 2012 for U.S. Appl. No. 10/539,288.
Issue notification dated Jun. 6, 2012 for U.S. Appl. No. 10/525,817.
Non final rejection of Sep. 21, 2012 for U.S. Appl. No. 10/539,288.
Non final rejection of Jul. 31, 2012 for U.S. Appl. No. 13/179,283.
Notice of Allowance dated Oct. 14, 2011 for U.S. Appl. No. 10/525,817.
Notice of Allowance dated Jan. 19, 2012 for U.S. Appl. No. 10/525,817.
Notice of Allowance dated Mar. 30, 2012 for U.S. Appl. No. 10/525,817.
Notice to file missing parts of May 11, 2012 for U.S. Appl. No. 13/455,223.
Office Action dated Sep. 17, 2012 for U.S. Appl. No. 12/330,709.
RCE filed Aug. 6, 2012 for U.S. Appl. No. 10/523,006.
RCE filed Jun. 9, 2012 for U.S. Appl. No. 10/572,644.
RCE filed Oct. 17, 2011 for U.S. Appl. No. 12/179,323.
RCE filed Aug. 20, 2012 for U.S. Appl. No. 10/539,288.
RCE filed Mar. 21, 2012 for U.S. Appl. No. 10/525,817.
Response to Notice to file missing parts of May 11, 2012 for U.S. Appl. No. 13/455,223 submitted Oct. 11, 2012.
Response to 1st Restriction Requirement of Oct. 5, 2011 for U.S. Appl. No. 12/095,778 submitted Mar. 5, 2012.
Response to 2nd Restriction Requirement of Jun. 27, 2012 for U.S. Appl. No. 12/095,778 submitted Dec. 27, 2012.
Response to non final rejection of Mar. 16, 2011 for U.S. Appl. No. 10/523,006 submitted Sep. 16, 2011.
Response to non final rejection of Apr. 25, 2011 for U.S. Appl. No. 10/539,288 submitted Oct. 25, 2011.
Response to Non final rejection of Jul. 31, 2012 for U.S. Appl. No. 13/179,283 submitted Jan. 30, 2013.
Response to Non final rejection of Mar. 31, 2011 for U.S. Appl. No. 10/572,644 submitted Sep. 30, 2011.
Response to restriction requirement of Apr. 24, 2012 for U.S. Appl. No. 13/179,283 submitted Jul. 23, 2012.
Restriction requirement of Apr. 24, 2012 for U.S. Appl. No. 13/179,283.
Final rejection dated Feb. 6, 2012 re U.S. Appl. No. 10/523,006.
Restriction Requirement dated Aug. 2010 re U.S. Appl. No. 10/539,288.
Response after Non-final rejection submitted Oct. 25, 2011 re U.S. Appl. No. 10/539,288.
Final rejection dated Dec. 22, 2012 re U.S. Appl. No. 10/539,288.
Notice of Appeal filed Jun. 19, 2012 re U.S. Appl. No. 10/539,288.
RCE filed Aug. 20, 2012 re U.S. Appl. No. 10/539,288.
Non final rejection dated Sep. 21, 2012 re U.S. Appl. No. 10/539,288.
Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Second amendment after Notice of Appeal submitted Sep. 28, 2009 re U.S. Appl. No. 10/545,795.
Advisory Action dated Oct. 21, 2009 re U.S. Appl. No. 10/545,795.
Interview summary dated Jul. 15, 2010 re U.S. Appl. No. 10/545,795.
Notice of Appeal filed Jul. 27, 2011 re U.S. Appl. No. 10/545,795.
Restriction requirement mailed Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.
Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Examiner's amendment communication dated May 12, 2011 re U.S. Appl. No. 10/525,817.
Notice of Allowance dated Oct. 14, 2011 re U.S. Appl. No. 10/525,817.
Notice of Allowance dated Jan. 19, 2012 re U.S. Appl. No. 10/525,817.
RCE dated Mar. 21, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement dated May 14, 2013 re U.S. Appl. No. 13/455,223.
Response submitted Aug. 14, 2013 to Restriction Requirement re U.S. Appl. No. 13/455,223.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Response submitted Oct. 7, 2011 to Restriction Requirement re U.S. Appl. No. 10/589,551.
Non-final rejection dated Oct. 26, 2011 re U.S. Appl. No. 10/589,551.
1st Restriction requirement of Oct. 5, 2011 re U.S. Appl. No. 12/095,778.
Response dated Mar. 5, 2012 to 1st Restriction Requirement re U.S. Appl. No. 12/095,778.

(56) References Cited

OTHER PUBLICATIONS

2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Adang et al., "The Contribution of Combinatorial Chemistry to Lead Generation: An Interim Analysis", Current Medicinal Chemistry 2001, 8, 985-998.
Affleck: "Solutions for library encoding to create collections of discrete compounds", Chemical Biology, 2001, 5:257-263.
Bain et al., "Biosynthetic site-specific incorporation of a non-natural amino acid into a polypeptipe", J. Am. Chem. Soc., 1989, 111, 8013-8014
Barnes, "Recent developments in the encoding and deconvolution of combinatorial libraries", Chemical Biology 2000, 4:346-350.
Chen et al., "Total Synthesis of Naturally Occurring Prostaglandin F2a on a Non-Cross-Linked Polystyrene Support", Tetrahedron Letters 39 (1998) pp. 3943-3946.
Coe et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res., 37, 1991, 487-493.
Gallop et al., "Applications of Combinatorial Technologies to Drug Discovery. 1. Background and Peptide Combinatorial Libraries", Journal of Medicinal Chemistr-y, 1994, vol. 37, No. 9, pp. 1233-1251.
Guillen Schlippe et al., "In Vitro Selection of Highly Modified Cyclic Peptides That Act as Tight Binding Inhibitors", J. Am. Chem. Soc. 2012, 134, 10469-10477.
Han et al., "Liquid-phase combinatorial synthesis", Proc. Natl. Acad. Sci. USA, vol. 92, pp. 6419-6423, Jul. 1995.
Kleiner et al., "Small-molecule discovery from DNA-encoded chemical libraries", Chem. Soc. Rev., 2011, 40, pp. 5707-5717.
Li et al., "Kinetics of RNA Degradation by specific base catalysis of transesterification involving the 2'-hydroxyl group", J. Am. Chem. Soc., 1999, 121, pp. 5364-5372.
Lipinski et al., "Experimental and computational approaches to estimate solubility and permeability in drug discovery and development settings", Adv. Drug Deliv. Rev., vol. 46 (1-3), 2001, pp. 3-26.
Lipinski, "Lead- and drug-like compounds: the rule-of-five revolution", Drug Discovery Today: Technologies, vol. 1, No. 4, 2004, pp. 337-341.
Ma et al., "In Vitro Selection of Unnatural Cyclic Peptide Libraries via mRNA Display", Book Ribosome Display and Related Technologies, ch. 21, pp. 367-390, 2012.
MacLean et al., "Glossary of terms used in combinatorial chemistry", Pure Appl. Chem., vol. 71, No. 12, pp. 2349-2365, 1999.
Meier et al, "Combinatorial Methods, Automated Synthesis and High-Throughput Screening in Polymer Research: The Evolution Continues", Macromol. Rapid Commun. 2004, 25, 21-33.
Needels et al., "Generation and screening of an oligonucleotide-encoded syntheticpeptide library", Proc. Natl. Acad. Sci. USA, vol. 90, pp. 10700-10704, Nov. 1993.
Ni et al., "Versatile Approach to Encoding Combinatorial Organic Syntheses Using Chemically Robust Secondary Amine Tags", J. Med. Chem. 1996, 39, 1601-1608.

Nicolaou et al., "Radiofrequency Encoded CombinatorialChemistry", Angew. Chem. Int. Ed. Engl., 1995, 34, No. 20, pp. 2289-2291.
Noren et al., "A general method for site-specific incorporation of unnatural aminoacids into protein", Science, American Association for the advancement of science, Washington, DC, vol. 244, 1989, pp. 182-188.
Starck et al., "The puromycin route to assess stereo- and regiochemical constraints on peptide bond formation in eukaryotic ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial synthesis the design of compound libraries and their application to drug discovery", Tetrahedron, 1995, vol. 51, No. 30., pp. 8135-8173.
Website: "Combinatorial chemistry", ukessays.co.uk/essays/chemistry/combinatorial-chemistry.php, Oct. 29, 2012, pp. 1-11.
Website wikipedia.org/wiki/DNA-encoded chemical library, Oct. 2, 2012, pp. 1-12.
Wermuth et al., "Glossary of terms used in medical chemistry", Pure & Appl. Chem, 1998, vol. 70, No. 5, pp. 1129-1143.
Ymane et al., "Discrimination between D- and L-Tyrosyl transfer ribonucleic acids in peptide chain elongation", Biochemistry, vol. 20, No. 25, Dec. 8, 1981, pp. 7059-7064.
Balkenhohl et al., "Combinatorial synthesis of small organic molecules", Angew Chem Int. Ed Engl. 1996, 35, pp. 2288-2337.
Chorghade, "Drug discovery and development", 2006, ISBN-13: 978-0-471-39848-6, Published by John Wiley & Sons, Inc., Hoboken, New Jersey.
1st Office Action of EP Application No. 10183942.1 dated Feb. 11, 2013.
2nd Office Action of EP Application No. 10184311.8 dated Feb. 6, 2013.
3rd Office Action of EP Application No. 08169346.7 dated Jan. 29, 2013.
5th Office Action of EP Application No. 03766117.0 dated May 31, 2012.
Communication pursuant to Rule 161(1) and 162 of EP Application No. 11720372.9 dated Dec. 12, 2012.
European search report for EP Application No. 10184069.2 dated Jun. 6, 2012.
Office Action of EP Application 09765460.2 dated May 7, 2012.
Response to 1st Office Action for EP Application No. 10184311.8 submitted Jan. 18, 2013.
Response to 2nd Office Action EP Application No. 08169346.7 submitted Dec. 21, 2012.
Response to 4th Office Action of EP Application No. 03766117.0 submitted Mar. 14, 2012.
Response to ESR dated Jan. 25, 2012 for EP Application No. 10192717.6 submitted Dec. 12, 2005 .
Response to ESR dated Feb. 6, 2012 for EP Application No. 10183942.1 submitted Jan. 9, 2013.
Response to oppositions against EP Application No. 1558744 submitted Dec. 5, 2012.
Notice of Acceptance dated Jun. 22, 2011 for Australian application No. 2003273792.
Notification of Allowance for Chinese patent application No. 200380104764.5, Sep. 3, 2012.
Office action of Aug. 20, 2012 for Canadian application No. 2544153.
Response to Office Action in EP 07114663.3 dated May 17, 2013.
3rd Office Action in European patent application No. 07114663.3 dated Jun. 3, 2013.
Request for Further Processing in EP 10184311.8 submitted Jan. 18, 2013.
Office action dated Jun. 2, 2013 in EP 10184311.8.
Response to 2nd Office Action of Feb. 24, 2012 in EP 08169346.7 submitted Dec. 21, 2012.
3rd Office Action dated Jan. 29, 2013 in EP 08169346.7.
Response to 4th Office Action dated Jun. 9, 2011 in EP 03766117.0 submitted Mar. 14, 2012.

(56) References Cited

OTHER PUBLICATIONS

5th Office Action from European Appllication No. 03766117.0 dated May 31, 2012.
Office Action from European Application No. 03766117.0 dated Mar. 26, 2013.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
Response submitted Jan. 9, 2013 to European Search Report re European Patent Application No. 10183942.1.
1st Office Action for European Patent Application No. 10183942.1 dated Feb. 11, 2013.
European Search Report issued Jun. 6, 2012 re EP 10184069.2.
Response dated Apr. 12, 2013 to European Search Report re European Patent Application No. 10184069.2.
1st Office Action for European Patent Application No. 10184069.2 dated Jul. 3, 2013.
Office Action in European patent application No. 10192716.8 dated Jul. 3, 2013.
Response to ESR dated Jan. 25, 2012 submitted Dec. 5, 2012.
Office Action dated Jul. 16, 2013 re European patent application No. 10192717.6.
European Office Action from EP 09765460.2 dated May 7, 2012.
Response to office action re 09765460.2 submitted Feb. 22, 2013 and Request for Further Processing.
Notice of Acceptance for Australian Application No. 2003273792 dated Jun. 22, 2011.
Office action of Aug. 20, 2012 re Canadian patent application No. 2,544,153.
Notice of Allowance of Sep. 3, 2012 re Chinese patent application No. 200380104764.5.
Office Action in Israeli patent application No. 207672 dated May 28, 2013.
Office Action in Israeli patent application No. 207673 dated May 28, 2013.
Office Action of Jan. 29, 2013 re Japanese patent application No. 2010-226107.
Decision of dismissal of amendment dated Aug. 20, 2013 re Japanese patent application No. 2010-226107.
Non-final Rejection dated Oct. 13, 2005 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Supplemental response submitted Jun. 2, 2010 re U.S. Appl. No. 12/330,709.
Ex Parte Quyale Action dated Jul. 27, 2010 re U.S. Appl. No. 12/330,709.
Response of Jan. 10, 2011 to Ex Parte Quayle Action re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
RCE submitted Oct. 17, 2011 re U.S. Appl. No. 12/179,323.
Non-Final Rejection dated Jul. 3, 2013 re U.S. Appl. No. 12/179,323.
First Restriction Requirement dated Apr. 4, 2008 re U.S. Appl. No. 10/523,006.
Response to first Restriction Requirement submitted Oct. 1, 2008 re U.S. Appl. No. 10/523,006.
Second Restriction Requirement dated Dec. 9, 2009 re U.S. Appl. No. 10/523,006.
Response to second Restriction Requirement submitted May 5, 2010 re U.S. Appl. No. 10/523,006.
Third Restriction Requirement dated Aug. 3, 2010 re U.S. Appl. No. 10/523,006.
Response to third Restriction Requirement submitted Feb. 1, 2011 re U.S. Appl. No. 10/523,006.
Non-final Rejection dated Mar. 16, 2011 re U.S. Appl. No. 10/523,006.
Response submitted Sep. 16, 2011 to non-final rejection re U.S. Appl. No. 10/523,006.
Bain, et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., Novel Solution Phase Strategy for the Synthesis of Chemical Libraries Containing Small Organic Molecules, J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-654, 2009.
Curran, "Strategy-Level Separations in Organic Synthesis: From Planning to Practise", Angew. Chem. Int. Ed., vol. 37, 1174-1196, 1998.
Frutos et al. "Enzymatic Ligation Reactions of DNA "Words" on Surfaces for DNA Computing", J. Am. Chem. Soc., vol. 120, No. 40, 10277-10282, 1998.
Gait, Chemical "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligotibonucleotides", in Oligonucleotide Synthesis: A Practical Approach, ed. M.J. Gait, IRL Press (Oxford, England and Washington, DC) 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4), 2002.
Glen Research Report, "Advances in RNA Synthesis and Structural Analysis", vol. 11, No. 2, 1998 (December).
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries, " PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Kempe et al., Chemical and Enzymatic Biotin-labeling of Oligodeoxyribonucleotides, Nucl. Acids Res., vol. 13, No. 1, 45-57, 1985.
Kinoshita et al., "Enzymatic Synthesis of Sequencing Primers Based on a Library of Tetramers", Chem. Express, No. 7, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and Its Application to Generation of Peptide-Aptamer-Based Inhibitors of Cathepsin E", J. Mol. Biol., vol. 387, 1186-1198, 2009.
Moore et al. "Site-specific Modification of Pre-mRAN: the 2'-hydroxyl Groups at the Splice Sites", Science, vol. 256, No. 5059, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).

(56) References Cited

OTHER PUBLICATIONS

Nielsen et al., "Towards Chemical Implementation of Encoded Combinatorial Libraries", Methods: A Companion to Meth: Enzymol., vol. 6, 361-371, 1994.
Roux et al., "Optimization and troubleshooting in PCR", PCR Methods Appl., vol. 4, No. 5, S185-S194, Apr. 1995.
Schmitz et al., "Solid-phase Enzymatic Synthesis of Oligonucleotides", Org. Lett., vol. 1, 1729-1731, 1999.
Seelig et al., "Site-directed Modification of Enzymatically Synthesized RNA: Transcription Initiation and Diels-Alder Reaction, " Tetrahed. Lett., vol. 38, 7729-7732, 1997.
Seo et al., "Click Chemistry to Construct Fluorescent Oligonucelotides for DNA sequencing", J. Org. Chem., vol. 68, 609-612, 2003.
Sherlin et al., "Chemical and Enzymatic Synthesis of tRNAs for High-throughput Crystallization", RNA, vol. 7, No. 11, 1671-1678, 2001.
Tabuchi et al., "AN Efficient Ligation Method in the Making of an in vitro Virus for in vitro Protein Evolution," Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed in the Surface of Encoded Bacteriophage", Chem. Biol., vol. 847-858, 2003 (September).
Wojczewski et al., "Fluorescen Oligonucleotides—Versatile Tools as Probes and Primers for DNA and RNA Analysis", Synlett, No. 10, 1667-1678, 1999.
Wong & Whitesides, "Enzymes in Synthetic Organic Chemistry", Tetrahedron Organic Chemistry Series vol. 12, Pergamon, Elsevier Science Lrd. (Oxford, England) 1994, pp. Xiii-xv, 1-40, and 329-334.
Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.
Strachan et al., "Human Molecular Genetics", 2nd edition, textbook published by Wiley-Liss, 1999.
Barrio et al., "Synthesis of modified nucleoside 3',5'-bisphophates and their incorporation into oligoribonucleotides with T4 RNA Ligase", American Chemical Society, vol. 17, No. 11, 1978.
Chan et al., "Altered DNA ligase I activity in Bloom's syndrome cells", Nature, vol. 325, pp. 357-359, 1987.
Cranston et al., "Studies on ribonucleic acid ligase", J.Biol.Chem., vol. 249, No. 23, pp. 7447-7456, 1974.
England et al., "Enzymatic oligoribonucleotide synthesis with T4 RNA ligase", American Chemical Society, vol. 17, No. 11, 1978.
Gassen et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth et al., "Interaction of *escherichia coli* host factor protein with oligoriboadenylates", Biochemistry, 19, pp. 6138-6446, 1980.
Hoffman et al., "Polynucleotide phosphorylase covalently bound to cellulose and ith use in the preparation of homopolynucleotides", Biochemical and biophysical research communications, vol. 41, No. 3, pp. 710-714, 1970.
Kiebom, "Enzymes that do not work ini organic solvents: Too polar substrates give too tight enzyme-product complexes", Recl. Tray. Chim. Pays-Bas, 107, pp. 347-348, 1988.
Middleton et al., "Synthesis and purification of oligoribonucleotides using T4 RNA ligase and reverse-phase chromatography", Analytical Biochemistry, 144, pp. 110-117, 1985.
Narang, "DNA synthesis", Tetrahedron, vol. 39, No. 1, pp. 3-22, 1983.
Neilson et al., "Synthesis of biologically active portions of an intercistronic region by use of a new 3'-phosphate incorporation method to protect 3'-OH and their binding to ribosomes", Eur. J. Biochem., 99, pp. 429-439, 1979.
Ochoa et al., "Enzymatic synthesis of polynucleotides", J.Biol. Chem., vol. 236, 12, pp. 3303-3311, 1961.
Willis et al., "DNA ligase I deficiency in Bloom's syndrome", Nature, vol. 325, pp. 355-357, 1987.
Decision to Grant dated Oct. 10, 2013 re European patent appliction No. 09154197.9.
Decision to Grant EP 10183942.1 dated Nov. 14, 2013.
Communication pursuant to Rule 161(1) and 162 for European Application No. 11720372.9 dated Dec. 12, 2012.
P101US01 Final rejection dated Oct. 28, 2013 re U.S. Appl. No. 12/330,709.
P104US00 Response submitted Oct. 11, 2013 re U.S. Appl. No. 10/523,006.
P123US02 Non-final rejection dated Nov. 15, 2013 re U.S. Appl. No. 13/455,223.
P129US00 Non-final rejection dated Oct. 8, 2013 re U.S. Appl. No. 12/095,778.
Kurz et al. Psoralen photo-crosslinked mRNA puromycin conjugates: a novel template for the rapid and facile preparation of mRNA-protein fusions, Nucleic Acids Res. Sep. 15, 2000; 28(18): E83.
d'Angelo et al., "HIV-1 integrase: the next target for AIDS therapy?", Pathol. Biol. 2001, 49, pp. 237-246.
Non final rejection dated Nov. 15, 2013 re U.S. Appl. No. 10/539,288.
Schreiber, "The small-molecule approach to biology—Chemical genetics and diversity-oriented organic synthesis make possible the systematic exploration of biology", C&EN, Mar. 3, 2003, pp. 51-61.
Balasubramanian, "The science of chemical discovery: probing the unknown with new technologies", DDT, vol. 5, No. 12, Dec. 2000, pp. 533-534.
Balasubramanian, "Solid phase chemical technologies for combinatorial chemistry", J. Cell. Biochem. Suppl., 37, 2001, pp. 28-33.
Opposition minutes dated Dec. 13, 2013 of oral proceedings re European Patent No. 1558744.
Written Decision re European patent No. 1558744 of Dec. 13, 2013.
1st office action dated Nov. 20, 2013 patent application No. 201210222023.8 in China.

\* cited by examiner

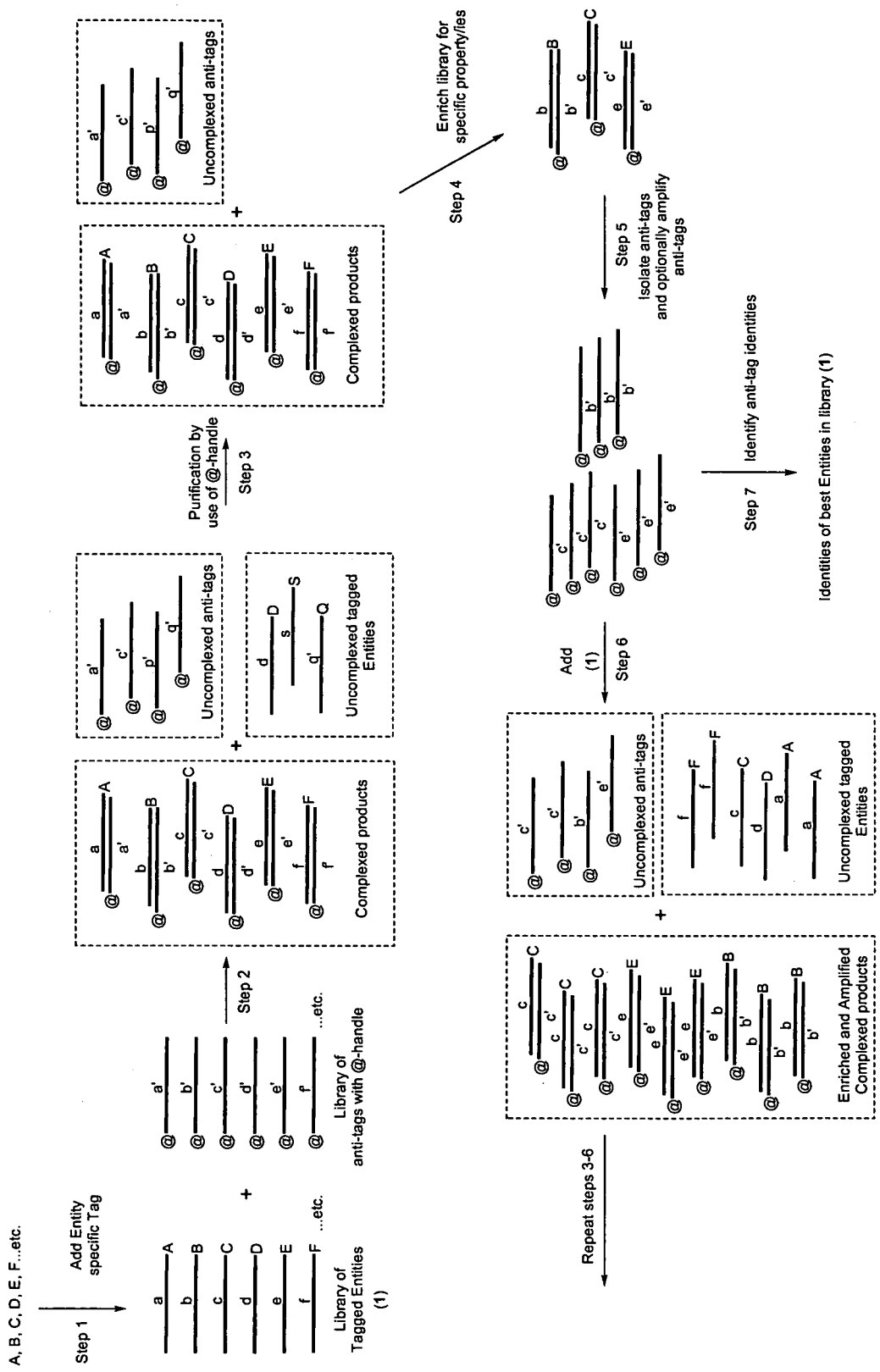
Figure 1. General Principle of Library Enrichment, Amplification and Identification

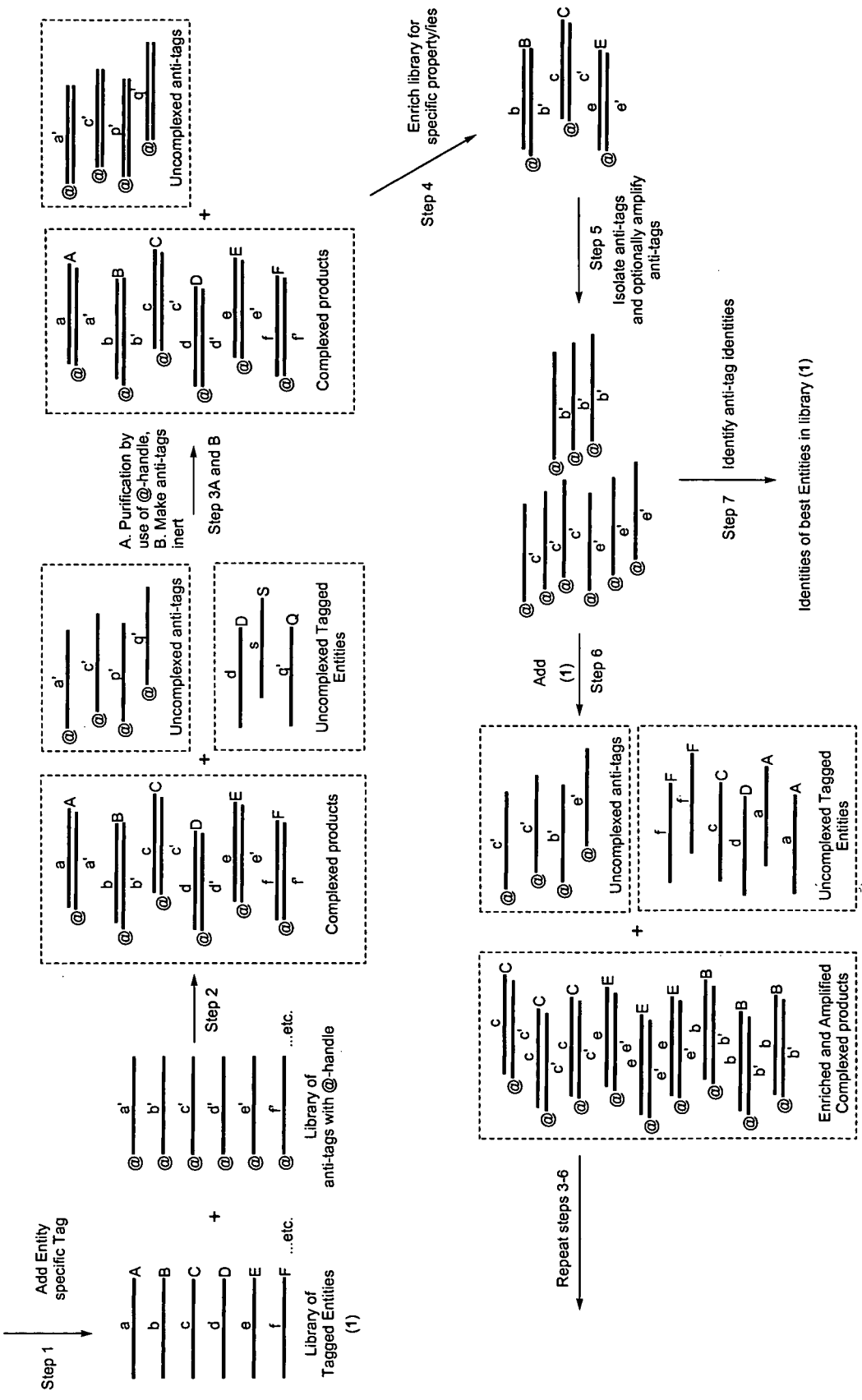
Figure 2. General Principle of Library Enrichment, Amplification and Identification

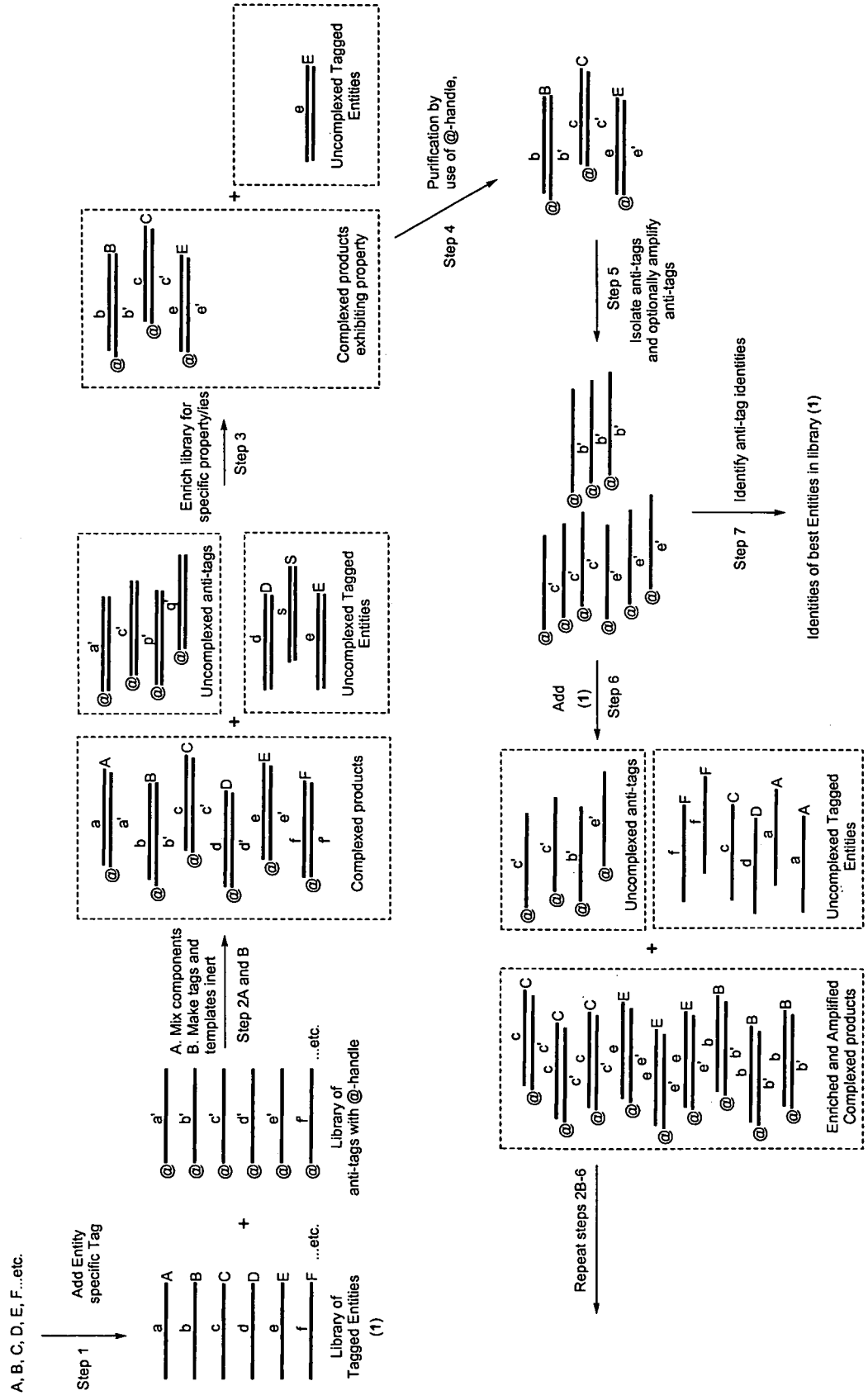
Figure 3. General Principle of Library Enrichment, Amplification and Identification

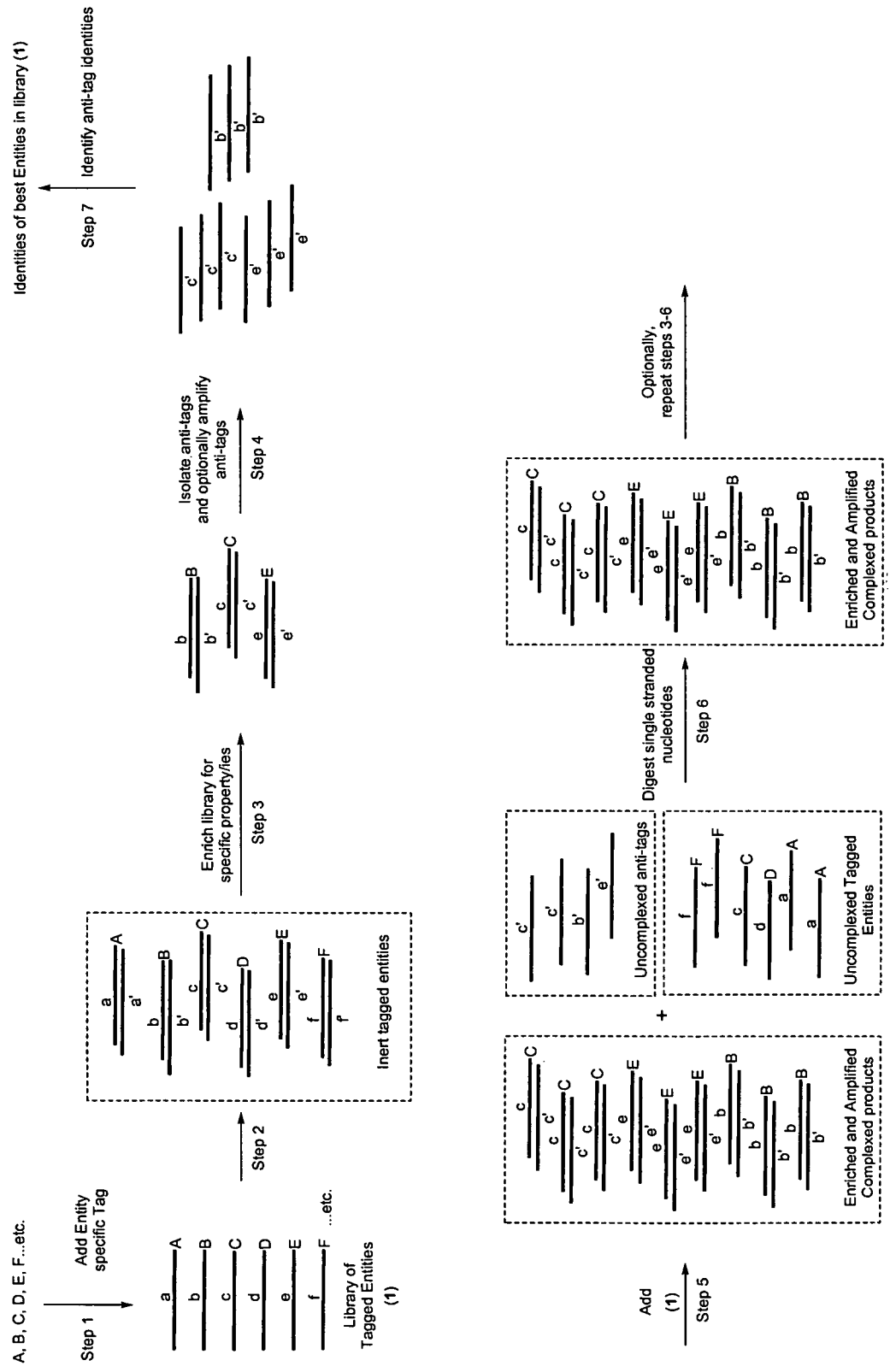
Figure 4. General Principle of Library Enrichment, Amplification and Identification

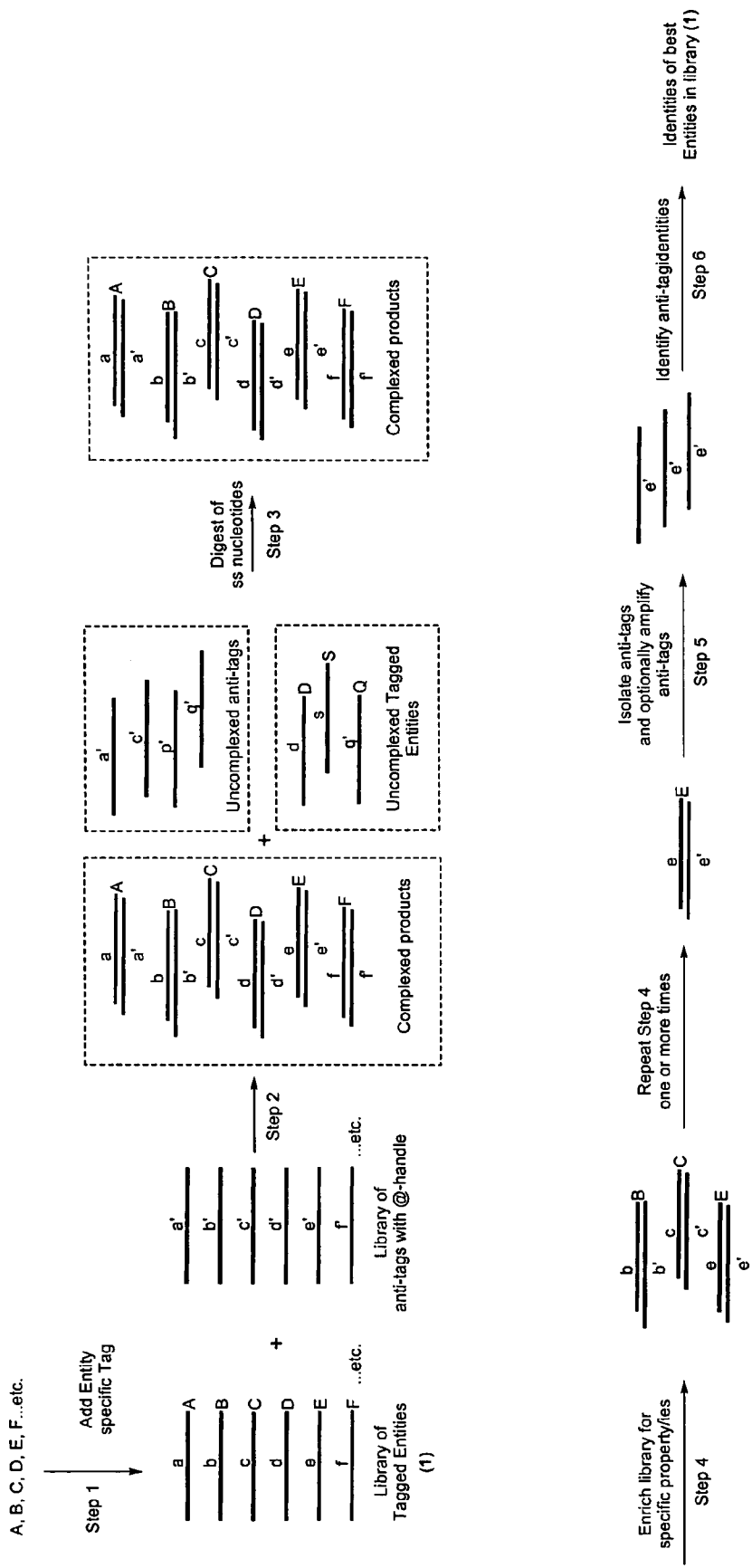
Figure 5. General Principle of Library Enrichment, anti-tag Amplification and Identification

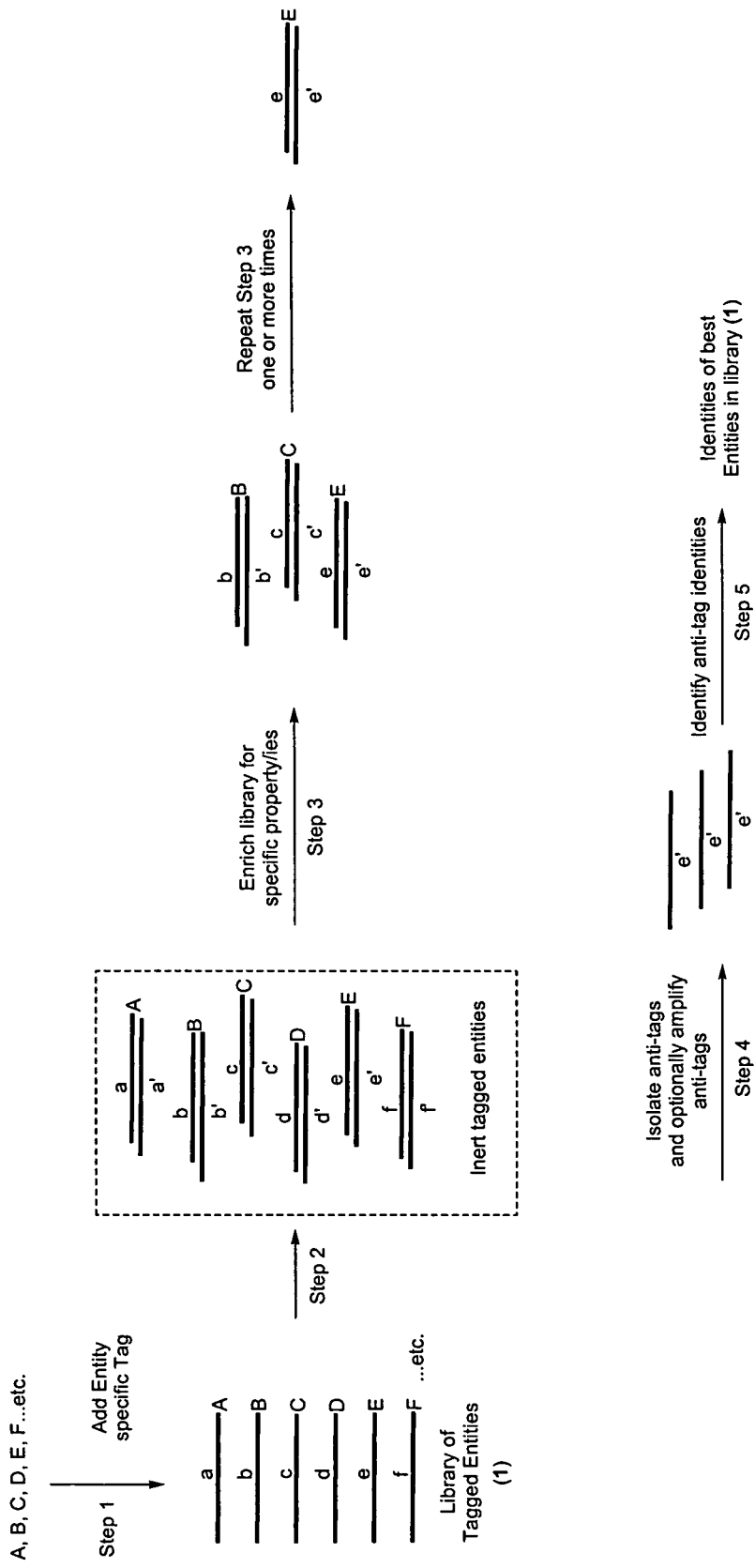
Figure 6. General Principle of Library Enrichment, Amplification and Identification

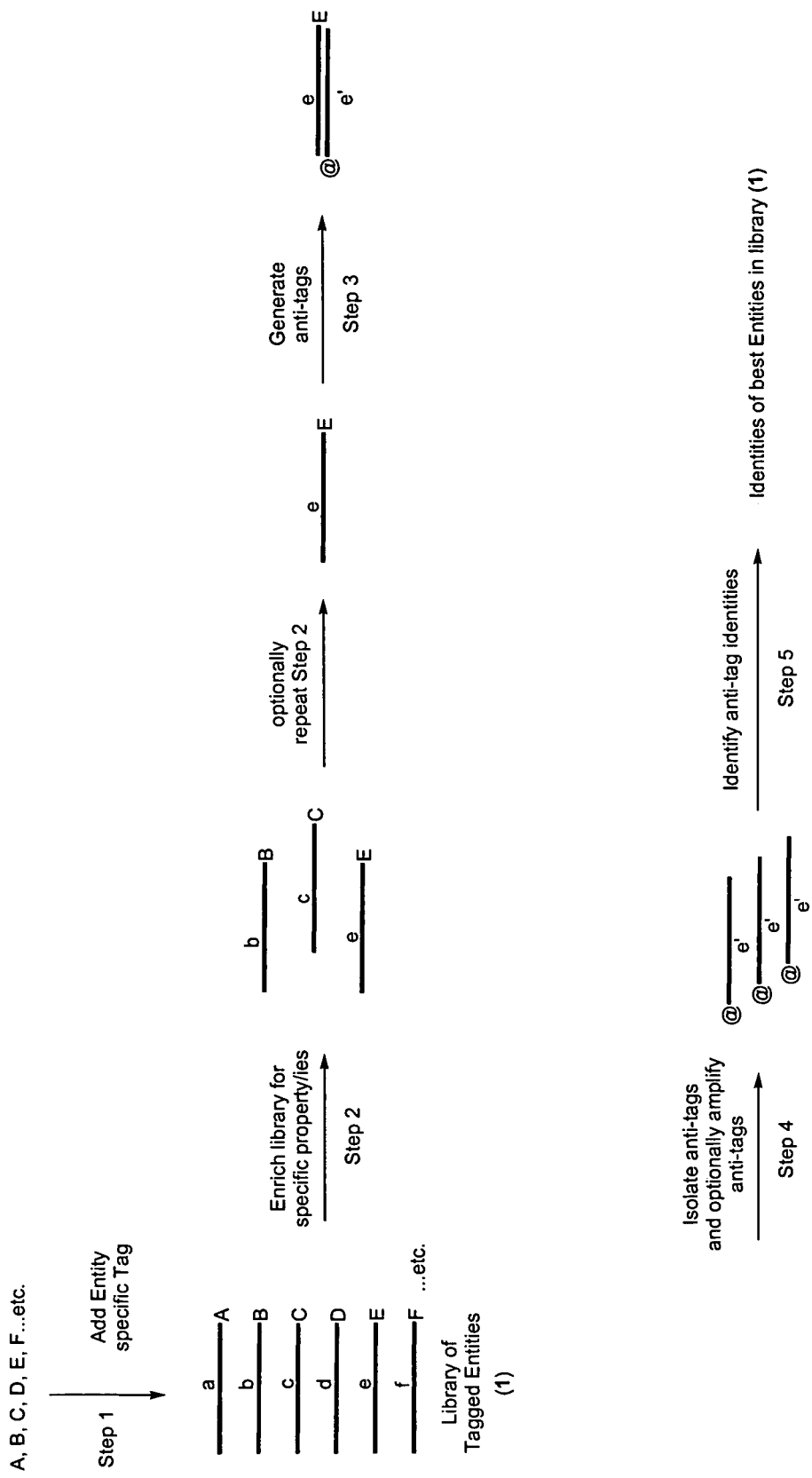
Figure 7. General Principle of Library Enrichment, Amplification and Identification

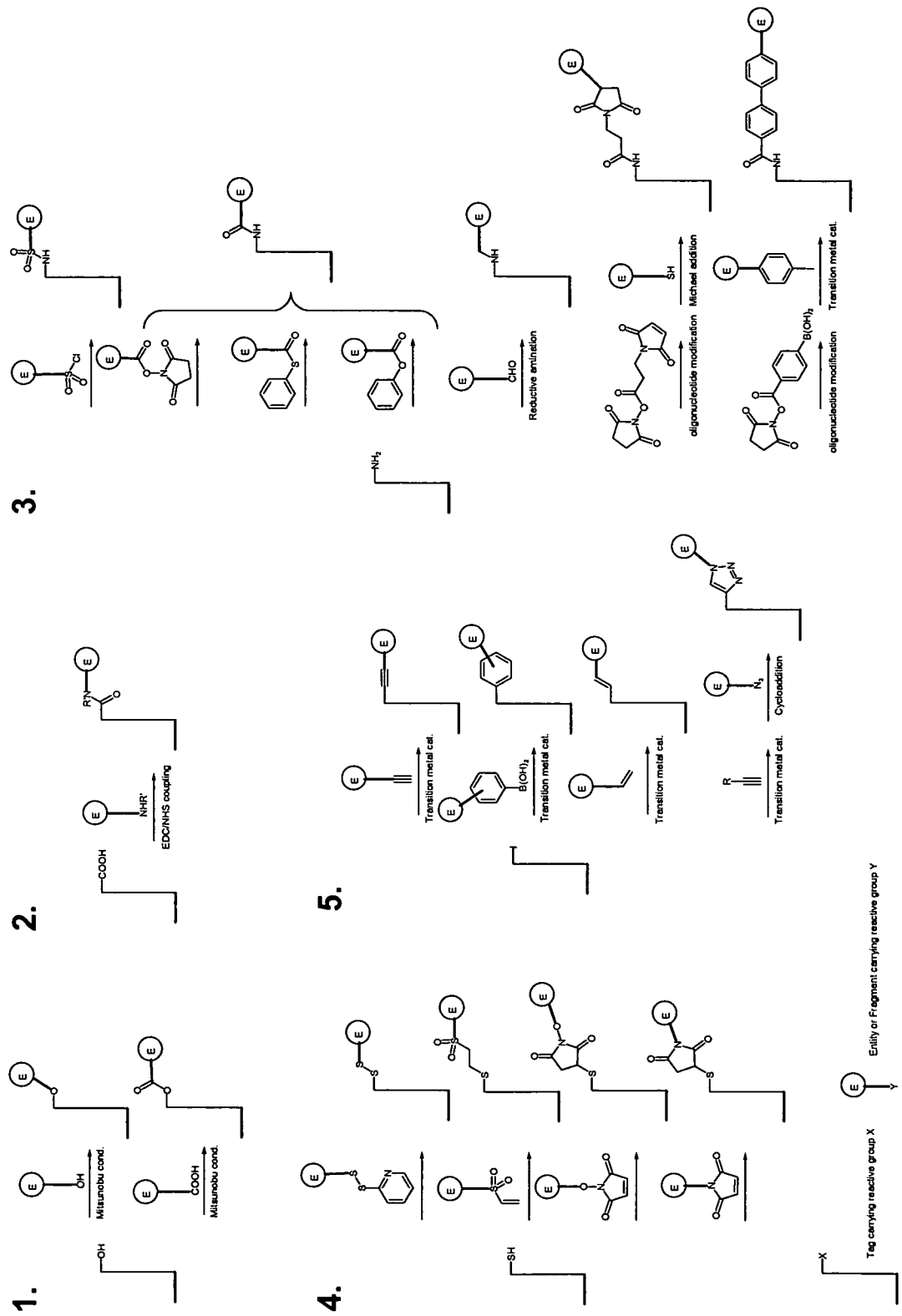
Figure 8. Tagging of Entity or Fragment

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial
<220> FEATURE:
<223> OTHER INFORMATION: synthetic tagging oligo-nt TO#1
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 1
ntatgcggac tgactggtac                                              20

<210> SEQ ID NO 2
<211> LENGTH: 20
<212> TYPE: DNA
<213> ORGANISM: Artificial
<220> FEATURE:
<223> OTHER INFORMATION: synthetic tagging oligo-nt TO#2
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 2
ntatgatgct taggcggtac                                              20

<210> SEQ ID NO 3
<211> LENGTH: 20
<212> TYPE: DNA
<213> ORGANISM: Artificial
```

```
<220> FEATURE:
<223> OTHER INFORMATION: synthetic tagging oligo-nt TO#3
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 3
ntatgtaccg tacgtggtac                                                   20

<210> SEQ ID NO 4
<211> LENGTH: 20
<212> TYPE: DNA
<213> ORGANISM: Artificial
<220> FEATURE:
<223> OTHER INFORMATION: synthetic  tagging oligo-nt TO#4
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 4
ntatgaatgc tagctggtac                                                   20

<210> SEQ ID NO 5
<211> LENGTH: 20
<212> TYPE: DNA
<213> ORGANISM: Artificial
<220> FEATURE:
<223> OTHER INFORMATION: synthetic  tagging oligo-nt TO#5
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 5
ntatggattg cgcgtggtac                                                   20

<210> SEQ ID NO 6
<211> LENGTH: 20
<212> TYPE: DNA
<213> ORGANISM: Artificial
<220> FEATURE:
<223> OTHER INFORMATION: synthetic tagging oligo-nt TO#6
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)

<400> SEQUENCE: 6
ntatgccact attagggtac                                                   20

<210> SEQ ID NO 7
<211> LENGTH: 40
<212> TYPE: DNA
<213> ORGANISM: Artificial
<220> FEATURE:
<223> OTHER INFORMATION: synthetic complementary oligo-nt CO#1
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 7
nataggatcc gtaccagtca gtccgcatag gaattctagt                              40
```

<210> SEQ ID NO 8
<211> LENGTH: 40
<212> TYPE: DNA
<213> ORGANISM: Artificial
<220> FEATURE:
<223> OTHER INFORMATION: synthetic complementary oligo-nt CO#2
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 8
nataggatcc gtaccgccta agcatcatag gaattctagt                     40

<210> SEQ ID NO 9
<211> LENGTH: 40
<212> TYPE: DNA
<213> ORGANISM: Artificial
<220> FEATURE:
<223> OTHER INFORMATION: synthetic complementary oligo-nt CO#3
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 9
nataggatcc gtaccacgta cggtacatag gaattctagt                     40

<210> SEQ ID NO 10
<211> LENGTH: 40
<212> TYPE: DNA
<213> ORGANISM: Artificial
<220> FEATURE:
<223> OTHER INFORMATION: synthetic complementary oligo-nt CO#4
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 10
nataggatcc gtaccagcta gcattcatag gaattctagt                     40

<210> SEQ ID NO 11
<211> LENGTH: 40
<212> TYPE: DNA
<213> ORGANISM: Artificial
<220> FEATURE:
<223> OTHER INFORMATION: synthetic complementary oligo-nt CO#5
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 11
nataggatcc gtaccacgcg caatccatag gaattctagt                     40

<210> SEQ ID NO 12
<211> LENGTH: 40
<212> TYPE: DNA
<213> ORGANISM: Artificial
<220> FEATURE:
<223> OTHER INFORMATION: synthetic complementary oligo-nt CO#6

```
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 12
nataggatcc gtaccctaat agtggcatag gaattctagt                            40

<210> SEQ ID NO 13
<211> LENGTH: 15
<212> TYPE: DNA
<213> ORGANISM: Artificial
<220> FEATURE:
<223> OTHER INFORMATION: synthetic oligo for PCR AO#1
<220> FEATURE:
<221> NAME/KEY: misc_feature
<222> LOCATION: (1)..(1)
<223> OTHER INFORMATION: n= 5' biotin (Glen research cat 10-1953-95)
      modified t, linked through photocleavable linker (Glen research
      10-4913-90).

<400> SEQUENCE: 13
nataggatcc gtacc                                                      15

<210> SEQ ID NO 14
<211> LENGTH: 15
<212> TYPE: DNA
<213> ORGANISM: Artificial
<220> FEATURE:
<223> OTHER INFORMATION: synthetic oligo for PCR AO#2

<400> SEQUENCE: 14
actagaattc ctatg                                                      15

<210> SEQ ID NO 15
<211> LENGTH: 7
<212> TYPE: PRT
<213> ORGANISM: Artificial
<220> FEATURE:
<223> OTHER INFORMATION: synthetic P#1

<400> SEQUENCE: 15

Gly Arg Gly Asp Ser Pro Cys
1               5

<210> SEQ ID NO 16
<211> LENGTH: 7
<212> TYPE: PRT
<213> ORGANISM: Artificial
<220> FEATURE:
<223> OTHER INFORMATION: synthetic P#2

<400> SEQUENCE: 16

Gly Arg Ala Asp Ser Pro Cys
1               5

<210> SEQ ID NO 17
<211> LENGTH: 7
<212> TYPE: PRT
<213> ORGANISM: Artificial
<220> FEATURE:
<223> OTHER INFORMATION: synthetic P#3

<400> SEQUENCE: 17

Gly Arg Gly Glu Ser Pro Cys
1               5
```

```
<210> SEQ ID NO 18
<211> LENGTH: 7
<212> TYPE: PRT
<213> ORGANISM: Artificial
<220> FEATURE:
<223> OTHER INFORMATION: synthetic P#4

<400> SEQUENCE: 18

Gly Asp Gly Arg Ser Pro Cys
1               5

<210> SEQ ID NO 19
<211> LENGTH: 4
<212> TYPE: PRT
<213> ORGANISM: Artificial
<220> FEATURE:
<223> OTHER INFORMATION: synthetic P#5

<400> SEQUENCE: 19

Cys Lys Lys Lys
1

<210> SEQ ID NO 20
<211> LENGTH: 6
<212> TYPE: PRT
<213> ORGANISM: Artificial
<220> FEATURE:
<223> OTHER INFORMATION: synthetic P#6

<400> SEQUENCE: 20

Cys Phe Phe Lys Lys Lys
1               5

<210> SEQ ID NO 21
<211> LENGTH: 21
<212> TYPE: DNA
<213> ORGANISM: Artificial
<220> FEATURE:
<223> OTHER INFORMATION: synthetic library of 65,536 tagging oligo-nt
      based on TO#2
<220> FEATURE:
<221> NAME/KEY: misc_feature
<222> LOCATION: (1)..(1)
<223> OTHER INFORMATION: n= c modified with 5'C 6 amino modifier Glen
      research Cat. 10-1916-90)
<220> FEATURE:
<221> NAME/KEY: misc_feature
<222> LOCATION: (8)..(15)
<223> OTHER INFORMATION: n= a, g, t, c

<400> SEQUENCE: 21
nctatgannn nnnnncggta c                                              21

<210> SEQ ID NO 22
<211> LENGTH: 40
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is T with phosphothiolate linkage.
<220> FEATURE:
<221> NAME/KEY: misc_feature
<222> LOCATION: (2)..(2)
<223> OTHER INFORMATION: n is A with phosphothiolate linkage.
<220> FEATURE:
<221> NAME/KEY: misc_feature
```

```
<222> LOCATION: (3)..(3)
<223> OTHER INFORMATION: n is T with phosphothiolate linkage.

<400> SEQUENCE: 22
nnnaggatcc gtaccagtca gtccgcatag gaattctagt                    40

<210> SEQ ID NO 23
<211> LENGTH: 40
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is T with phosphothioate linkage.
<220> FEATURE:
<221> NAME/KEY: misc_feature
<222> LOCATION: (2)..(2)
<223> OTHER INFORMATION: n is  A with phosphothiolate linkage.
<220> FEATURE:
<221> NAME/KEY: misc_feature
<222> LOCATION: (3)..(3)
<223> OTHER INFORMATION: n is  T with phosphothiolate linkage.
<220> FEATURE:
<221> NAME/KEY: misc_feature
<222> LOCATION: (17)..(24)
<223> OTHER INFORMATION: n is a, c, g, or t

<400> SEQUENCE: 23
nnnaggatcc gtaccgnnnn nnnntcatag gaattctagt                    40

<210> SEQ ID NO 24
<211> LENGTH: 15
<212> TYPE: DNA
<213> ORGANISM: Artificial
<220> FEATURE:
<223> OTHER INFORMATION: synthetic
<220> FEATURE:
<221> NAME/KEY: misc_feature
<222> LOCATION: (1)..(1)
<223> OTHER INFORMATION: n is T with phosphothiolate linkage.
<220> FEATURE:
<221> NAME/KEY: misc_feature
<222> LOCATION: (2)..(2)
<223> OTHER INFORMATION: n is A with phosphothiolate linkage.
<220> FEATURE:
<221> NAME/KEY: misc_feature
<222> LOCATION: (3)..(3)
<223> OTHER INFORMATION: n is T with phosphothiolate linkage.

<400> SEQUENCE: 24
nnnaggatcc gtacc                                               15
```

US 8,722,583 B2

METHOD FOR SELECTING A CHEMICAL ENTITY FROM A TAGGED LIBRARY

This application is a continuation-in-part of Ser. No. 10/525,817, filed Sep. 15, 2005, which is the national stage of PCT/DK03/00739 filed Oct. 30, 2003, which claims the benefit of U.S. provisional application Ser. No. 60/422,167, filed Oct. 30, 2002; U.S. provisional application Ser. No. 60/434,425, filed Dec. 19, 2002, and U.S. provisional application Ser. No. 60/486,199, filed Jul. 11, 2003, all which are hereby incorporated by reference in their entirety. All patent and non-patent references cited in these patent applications, or in the present application, are hereby incorporated by reference in their entirety.

TECHNICAL FIELD OF THE INVENTION

The present invention relates to a method for determining the identity of a chemical entity, such as a chemical compound or a subset of chemical compounds. The chemical entity is selected from a library composed of a plurality of different chemical entities, each having appended a unique identifier tag. The chemical entity of interest has a desired property, e.g. a property which provides for a partition of said chemical compound from the initial library. Subsequent to the partition, the chemical entity is identified by decoding the tag.

BACKGROUND

There is an increasing need to find new molecules which can effectively modulate a wide range of biological process, especially biological processes relating to medicine and agriculture. Traditionally such molecules have been sought after using a so-called rational approach, that is the initial generation of molecules having a new structure, assaying the properties of the molecules, formulating structure-activity relationships, and then synthesising slightly amended new candidates.

Another approach involves the generation of a combinatorial library and subjecting this library to a condition in order to identify one or more compounds which are able to perform a preselected property relative to this condition. However, it remains a major problem to identity the compound having the preselected property, especially, when this compound is altered in response to the condition. As far as natural polypeptides are concerned the identity problem has been solved by connecting the encoding RNA or DNA to the polypeptide. Exemplary of this approach is phage display (Cwirla et al., Proc. Natl. Acad. Sci. USA, 87:6378-6382 (1990); Scott et al., Science, 249:386-390 (1990); and Devlin et al., Science, 249: 404-406 (1990)) and mRNA-polypeptide fusion products (U.S. Pat. No. 5,843,701 and WO 00/47775).

EP 643 778 B1 discloses a method in which a polypeptide can be identified in a library of bifunctional molecules. The library comprises a plurality of bifunctional molecules produced by step-wise addition of an amino acid and a corresponding oligonucleotide to each side of a linker molecule. The library is generally produced by traditional split and combine techniques.

In an aspect of the present invention it is the object to devise an identification method using a versatile library not confined to polypeptides. In another aspect the use of a library produced by attachment of a tag to a molecular entity in a few steps is suggested, avoiding a multi-step synthesis used in the prior art.

SUMMARY OF THE INVENTION

The present invention is related to a method for determining the identity of a chemical entity having a preselected property, comprising the steps of:
i) generating a tagged library of chemical entities by appending unique identifier tags to chemical entities,
ii) subjecting the library to a condition, wherein a chemical entity or a subset of chemical entities having a predetermined property is partitioned from the remainder of the library,
iii) recovering an anti-tag from the partitioned library, said anti-tag being capable of interacting with the unique identifier tag in a specific manner, and
iv) identifying the chemical entity/ies having a preselected function by decoding the anti-tag.

The tag is appended the chemical entity by a suitable process. Notably, each chemical entity is appended a tag by a reaction involving a chemical reaction between a reactive group of the chemical entity and a reactive group of the tag. The attachment of the chemical entity may be directly or through a bridging molecule part. The molecule part may be any suitable chemical structure able to the connect the chemical entity to the tag.

The unique identifier tag attached to the chemical entity suitably comprises recognition units, that is units which may be recognised by recognition groups associated with the tag. A variety of different kinds of recognition exist in nature. Examples are antibodies which recognise an epitope, proteins which recognise another protein, mRNA which recognise a protein, and oligonucleotides which recognise complementing oligonucleotide sequences. Generally, it is preferred that the unique identifier tag is a sequence of nucleotides.

The anti-tag has the ability to interact with the unique identifier tag in a specific manner. The chemical structure of the anti-tag is to a large extent dependant on the choice of unique tag. As an example, if the unique tag is chosen as an antibody, the anti-tag is selected as the epitope able to associate with the antibody. In general, it is preferred to use an anti-tag comprising a sequence of nucleotides complementary to a unique identifier tag.

The method may be performed without amplification in certain embodiments. However, when larger libraries are intended, it is in general preferred to use an anti-tag which is amplifiable. Anti-tags comprising a sequence of nucleotides may be amplified using standard techniques like PCR. In the event the anti-tag is a protein, the protein may be amplified by attaching the mRNA which has encoded the synthesis thereof, generating the cDNA from the mRNA and subjecting said mRNA to a translation system. Such system is described in WO 98/31700 the content of which is incorporated herein by reference. An alternative method for amplifying a protein tag is to use phage-displayed proteins.

In the event the tag as well as the anti-tag is a sequence of nucleic acids, a tag:anti-tag hybrid may be formed prior to the subjecting the library to partitioning conditions or subsequent to the partitioning step. In some embodiments of the invention it is preferred to form the tag:anti-tag hybrid prior to the partition step in order to make the appended nucleotide sequence inert relative to the system as it is well known that certain sequences of nucleotides can bind to a target or catalyse a chemical reaction.

The oligonucleotide anti-tag may be formed in a variety of ways. In one embodiment of the invention, the anti-tag is formed as an enzymatic extension reaction. The extension comprises the initial annealing of a primer to the unique identifier tag and subsequent extension of the primer using a polymerase and dNTPs. Other types of extension reactions may also be contemplated. As an example ligases may be used to create the primer starting from di- or trinucleotide substrates and the extension may be performed using a suitable polymerase.

It may be desirable to recover the anti-tag at various steps during the process. To this end it is preferred in some aspects of the invention to provide the primer provided with a handle capable of binding to a suitable affinity partner. An arsenal of different handles and affinity partners are available to the skilled person in the art. The most widely used handle is biotin, which in general are also preferred according to the present invention.

Biotin binds to the affinity partner streptavidin or avidin. A standard technique in the laboratory is to recover a biochemical entity having attached a biotin using a solid phase covered with streptavidin. Suitably, the solid phase is a bead which may be separated from the liquid after the binding action by rotation or a magnetic field in case the solid bead comprises magnetic particles.

In other aspects of the present invention, the anti-tag is provided as a separate oligonucleotide. The separate oligonucleotide may be produced using standard amidite synthesis strategies or may be provided using other useful methods. It is in general preferred to provide the oligonucleotide by synthesis, at least in part, because the biotin amidite is easily incorporated in a nascent oligonucleotide strand. Following the addition of an oligonucleotide anti-tag to a liquid comprising chemical entities tagged with complementing oligonucleotide tags a double stranded library is formed as a hybridisation product between the unique identifier tag and the anti-tag oligonucleotide.

As mentioned above, the anti-tag oligonucleotide may be provided with a handle, such as biotin, capable of binding to an affinity partner, such as streptavidin or avidin.

Following the addition of the anti-tag oligonucleotides to the tagged chemical entities, some of the oligonucleotides present in the media may not find a partner. In one aspect of the invention it is preferred that oligonucleotides not hybridised to a cognate unique identifier and/or anti-tag are transformed into a double helix. In other aspects of the invention single stranded oligonucleotides are degraded prior to step ii) to avoid unintended interference.

The handle may be used to purify the library prior to or subsequent to the partitioning step. In some embodiments of the invention, the purification step is performed prior to the partitioning step to reduce the noise of the system.

In another aspect the handle is used to purify the partitioned library subsequent to step ii) in order to recover a double stranded product which may be amplified.

The library is subjected to a condition in order to select chemical entities having a property which is responsive to this condition. The condition may involve the exposure of the library to a target and partitioning the chemical entities having an affinity towards this target. Another condition could be subjecting the library to a substrate and partitioning chemical entities having a catalytical activity relative to this substrate.

The anti-tag can be formed subsequent to the partitioning step. In an aspect of the invention, the single stranded nucleotide serving as a tag is made double stranded while the chemical entity is attached to the target of an affinity partitioning. Optionally, in a repeated temperature cycle, a plurality of anti-tags may be formed as extension products using the tag as template. In another aspect of the invention, the chemical entity bearing the single stranded oligonucleotide is detached from the target and a complementing anti-tag is subsequently prepared.

In the event the anti-tag comprises a handle, this handle can be used to purify the partitioned library. The recovery of the anti-tag is then performed by melting off said anti-tag from a partitioned double stranded library. Optionally, the amount of anti-tags may be multiplied by conventional amplification techniques, such as PCR.

The method according to the invention can be performed using a single partitioning step. Usually, it is preferred, however, to use more than one partitioning step in order to select the candidate having the desired properties from a large library. Thus, the recovered anti-tags may be mixed with the initial library or a subset thereof and the steps of partitioning (step ii)) and recovery (step iii)) may is repeated a desired number of times. Optionally, single stranded moieties in the mixture may be degraded or removed or made inert as described above.

Generally, the partitioned library obtained in step ii) is subjected to one or more further contacting steps using increasing stringency conditions. The stringency conditions may be increased by increasing the temperature, salt concentration, acidity, alkalinity, etc.

In one embodiment of the invention, the partitioned library is not subjected to intermediate process steps prior to a repeated contacting step. Especially, the partitioned library is not subjected to intermediate amplification of the anti-tag. This embodiment may be of advantage when relatively small libraries are used.

The method of the invention terminates with a decoding step, that is a step in which the identity of the chemical entity or entities are deciphered by an analysis of the anti-tag. When the anti-tag is an oligonucleotide, the decoding step iv) may be performed by sequencing an anti-tag nucleotide. Various methods for sequencing are apparent for the skilled person, including the use of cloning and exposure to a microarray.

DETAILED DESCRIPTION OF THE INVENTION

The tags contain recognizing groups such as e.g. nucleotide sequence(s), epitope(s) a.o. The tags carries information of the entity to which it is attached, such as e.g. entity structure, mass, spatial position (plate information) etc. The tags may be composed of monoclonal antibodies, peptides, proteins, oligonucleotides, DNA, RNA, LNA, PNA, natural peptides, unnatural peptides, polymeric or oligomeric hydrazino aryl and alkyl carboxylic acids, polymeric or oligomeric aminoxy aryl and alkyl carboxylic acids, peptoids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da).

The initial library of chemical compounds tagged with an identifier sequence, may be prepared in several ways. As non-limiting examples, the following methods are contemplated:

A. Entities can be single compounds in their final "state", which are tagged individually and separately. E.g. single compounds may individually be attached to a unique tag. Each unique tag holds information on that specific compound, such as e.g. structure, molecular mass etc. By use of the present method, anti-tags may be isolated. These anti-tags are capable of interacting with a unique tag in a specific manner attached to a compound exhibiting selected properties. The decoding of an anti-tag capable of specific interacting with a unique tag will reveal information, stored in that tag, about that compound.

B. An entitiy can be a mixture of compounds, which may be considered to be in their final "state". These entities are normally tagged individually and separately, i.e. each single compound in a mixture of compounds may be attached to the same tag. Another tag may be used for another mixture of compounds. Each unique tag holds information on that specific mixture, such as e.g. spatial position on a plate. By use of the method according to the invention, anti-tags may be isolated. Anti-tags are capable of specific interaction with a unique tag attached to a compound exhibiting selected properties. The isolation of anti-tags capable of showing specific interaction with that unique tag will reveal information, stored by that tag, about the presence of a compound, exhibiting selected properties, in that mixture. In order to identify specific compounds within such a mixture, standard deconvolution techniques maybe used.

C. Entities which are not in their final "state" may be tagged individually and separately during their preparation. Each tag is attached to a fragment of the final compound/entity. Each fragment contains one or more reactive groups. Each tagged fragment is placed in e.g. one separate well on a plate and then added further untagged fragments containing reactive groups. All fragments combine to generate the final product, which is tagged. Each tag holds information on the identity of one fragment and e.g. spatial position of that fragment on a plate. E.g. plate 1 contains fragment X (e.g. carrying an amine) attached to a tag.

Plate X. Starting situation (prior to formation of entities in their final "state").

|  | Alkylating agents | | | |
| --- | --- | --- | --- | --- |
| Acylating agents | A | B | C | ... |
| 1 | Tagx11-X | Tagx12-X | Tagx13-X | ... |
| 2 | Tagx21-X | Tagx22-X | Tagx23-X | ... |
| 3 | Tagx31-X | Tagx32-X | Tagx33-X | ... |
| ... | ... | ... | ... | ... |

X denotes a fragment.

Plate X. Plate of products (i.e. entities in their final "state", i.e. after addition of all fragments/components).

|  | Alkylating agents | | | |
| --- | --- | --- | --- | --- |
| Acylating agents | A | B | C | ... |
| 1 | Tagx11-XA1 | Tagx12-XB1 | Tagx13-XC1 | ... |
| 2 | Tagx21-XA2 | Tagx22-XB2 | Tagx23-XC2 | ... |
| 3 | Tagx31-XA3 | Tagx32-XB3 | Tagx33-XC3 | ... |
| ... | ... | ... | ... | ... |

As an example XA2 denotes entity XA2 in its final state, i.e. fully assembled from fragments X, A and 2.

Each tag holds e.g. structural information on X and e.g. spatial information on each tagged fragment and thereby also on the structure of the final product from each well. On another plate, fragment Y is tagged, etc.

Each well may also contain a mixture of compounds and used as described in B above.

D. This method allows unique tagging of each individual entity formed in a mixture of other uniquely tagged entities. Each fragment is attached to a tag and each fragment carries one or more reactive groups. All fragments react with each other to generate the final product containing as many tags as fragments. The tags may be combined into one tag through an intramolecular reaction or association followed by cleavage. E.g. A:

A.

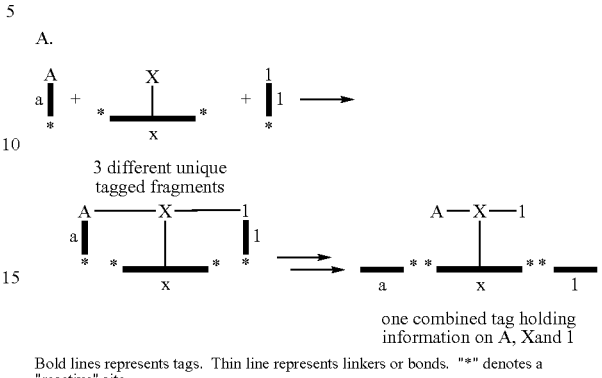

Bold lines represents tags. Thin line represents linkers or bonds. "*" denotes a "reactive" site.

One example of the above embodiment involves tags of oligonucleotides, which combine through chemical ligation or enzyme catalyzed ligation.

Alternatively, the tags react prior to the reaction of fragments. In that process the fragments will be cleaved from their tag or cleaved afterwards. E.g. B:

B.

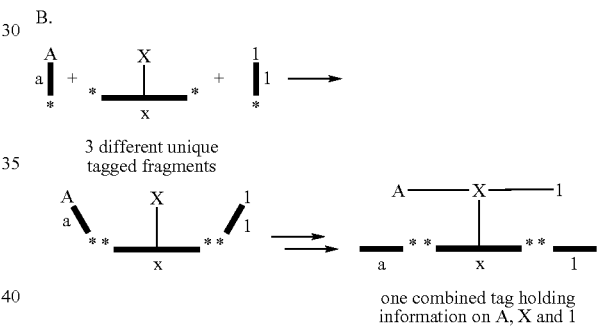

Bold lines represents tags. Thin lines represents linkers or bonds. "*" denotes a "reactive" site.

An embodiment of the above schematic representation being, when the tags are nucleotides, which combine through chemical ligation or enzyme catalyzed ligation.

In one further aspect, each compound is prepared by simultaneous or sequentially tagging and fragment reaction as illustrated in scheme C:

C.

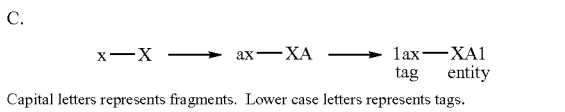

Capital letters represents fragments. Lower case letters represents tags.

A fragment "X" is linked to a tag "x". Another fragment is linked to "X" e.g. "A" and so is a unique tag for that fragment e.g. "a".

The entities maybe single compounds or a mixture of compounds. Entities may consists of oligonucleotides, DNA, RNA, LNA, PNA, natural peptides, unnatural peptides, polymeric or oligomeric hydrazine aryl or alkyl carboxylic acids, polymeric or oligomeric aminoxy aryl or alkyl carboxylic acids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da).

In one preferred embodiment, entities consist of small non-polymeric molecules (molecular weight<1000 Da). Small molecules are generally the compounds of interest in the quest for drug oral candidates. Especially, small molecules not occurring in Nature are of interest in the drug discovery process and in one aspect of the present invention the method are designed to select a oral drug candidate. A variety of drug candidate libraries are available on the market. The drug candidates of the library usually comprise a reactive group or a group which can be altered into a reactive group. In one preferred aspect of the present invention each of the members of the drug candidate library is appended a nucleic acid tag via said reactive group of the library member and a reactive group on the nucleic acid. Preferably, the nucleic acid is an oligonucleotide.

In another aspect of the invention, entities consist of large non-polymeric molecules (molecular weight>1000 Da). In still another embodiment, entities consist of polymeric molecules.

The tags and anti-tags may be composed of RNA linked to monoclonal antibodies, proteins, LNA, PNA, natural polypeptides, unnatural polypeptides, polymeric or oligomeric hydrazino aryl or alkyl carboxylic acids, polymeric or oligomeric aminoxy aryl or alkyl carboxylic acids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da).

Alternatively, anti-tags may be composed of DNA linked to monoclonal antibodies, proteins, LNA, PNA, natural polypeptides, unnatural polypeptides, polymeric or oligomeric hydrazino aryl or alkyl carboxylic acids, polymeric or oligomeric aminoxy aryl or alkyl carboxylic acids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da). Alternatively, anti-tags are just composed of oligonucleotides, DNA or RNA. In a preferred embodiment, anti-tags are composed of DNA. In another preferred embodiment anti-tags are composed of RNA.

Anti-tags which are linked to DNA or RNA are also encoded by the DNA/RNA linked to them, e.g. phage displayed or polysome displayed antibodies, peptides or proteins, and via DNA-templated synthesis of anti-tags, where the DNA encode the synthesis of the anti-tag, which is linked to its DNA during its synthesis.

Each chemical compound or group of compounds may be associated with a tag through formation of a covalent or non-covalent bond. For covalent bond formation, tagging may involve, but is not limited to, the formation of a cycloaddition product, an alkylation product, an arylation product, an acylation product, an amide bond, a carboxylic ester bond, a sulfonamide bond, a disulfide bond, an S-alkyl bond, an NR-alkyl bond, an O-alkyl bond, an aryl-vinyl bond, an alkyne-vinyl bond, an oxime bond, an imine bond, a bicyclic product, a trizole, a hexene, a 7-Oxa-bicyclo[2.2.1]hept-2-ene derivative, a 7-Aza-bicyclo[2.2.1]hept-2-ene derivative or a 7-Methyl-7-aza-bicyclo[2.2.1]hept-2-ene. Non-covalent bonds may involve, but are not limited to, attachment via e.g. hydrogen bonding, van der Waals interactions, pi-stacking or through hybridization. Hybridization may be between complementary strands of DNA, RNA, PNA or LNA or mixtures thereof. In such case both the tag and the chemical compound carries such a strand complementary to each other. The tagged entity, compound or mixture of compounds may be transformed into a new tagged entity, e.g. by transformation of the entity or by transformation of the tag. The transformation may be caused by either chemical or physical transformations such e.g. addition of reagents (e.g. oxidizing or reducing agents, pH adjustment a.o.) or subjection to UV-irradiation or heat.

The complex between tags and anti-tags may be formed on individually tagged entities immediately after tagging. Alternatively, after mixing individually tagged entities, either before or after the optionally use of library purification, or either before or after library enrichment for specific properties. When tags and anti-tags are composed of nucleotides the complex consists of a double stranded nucleotide, e.g. duplex DNA or hybrids DNA/RNA.

The purification handle (denoted "@") may be connected to the anti-tag. The purification handle contains a recognizing group(s) such as e.g. nucleotide sequence(s), epitopes, reactive groups, high affine ligands a.o. The purification handles may be composed of monoclonal antibodies, peptides, proteins, DNA, RNA, LNA, PNA, natural peptides, unnatural peptides, polymeric or oligomeric hydrazine aryl or alkyl carboxylic acids, polymeric or oligomeric aminoxy aryl or alkyl carboxylic acids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da). Purification handles may e.g. be a nucleotide sequence, biotin, streptavidin, avidin, "his-tags", mercapto groups or disulfide/activated disulfide groups. The purification handle may be part of the anti-tag, e.g. in the case the anti-tag is nucleotide based or e.g. antibodies where part of the antibody may serve as epitop for another antibody (e.g. immobilized antibody which serve as purification filter).

Purification filters contains components which associate, interact or react with purification handles whereby a complex is formed. This complex allows separation of non-complexed tagged entities and complexed tagged entities. The purification filter contains a recognizing group(s) such as e.g. nucleotide sequence(s), epitopes, reactive groups, high affine ligands a.o. The purification filter may be composed of monoclonal antibodies, peptides, proteins, DNA, RNA, LNA, PNA, natural peptides, unnatural peptides, polymeric or oligomeric hydrazine aryl or alkyl carboxylic acids, polymeric or oligomeric aminoxy aryl or alkyl carboxylic acids, other natural polymers or oligomers, unnatural polymers (molecular weight>1000 Da) or oligomers (molecular weight<1000 Da), small non-polymeric molecules (molecular weight<1000 Da) or large non-polymeric molecules (molecular weight>1000 Da). Purification filters may e.g. be a nucleotide sequence, biotin, strepdavidin, avidin, "his-tags", mercapto groups or disulfide/activated disulfide groups.

The library is probed and enriched for properties. Properties may be affinity, catalytic activity or membrane penetrating capability a.o.

Amplification may use PCR or RTPCR techniques. Anti-tags are amplifiable in some aspects of the invention. Anti-tags may be separated from tags by use of physical or chemical means, such as e.g. UV-irradiation, heat, pH-adjustment, use of salt solutions a.o.

Isolated tagged entities may be identified either trough their tag or anti-tag. Identification may be accomplished by cloning of anti-tags and sequencing their DNA/RNA or through mass analysis of either tagged entities or anti-tags or complexes of anti-tags/tagged entities.

The library of tagged entities may involve $10$-$10^{20}$ or $10$-$10^{14}$ or $10$-$10^2$ or $10$-$10^3$ or $10^2$-$10^3$ or $10^2$-$10^4$ or $10^3$-$10^6$ or $10^3$-$10^8$ or $10^3$-$10^{10}$ or $10^3$-$10^{14}$ or $10^5$-$10^6$ or $10^5$-$10^8$ or $10^5$-$10^{10}$ or $10^5$-$10^{14}$ or $10^8$-$10^{14}$ or $10^{14}$-$10^{20}$ entities.

Library complexes of tagged entities and anti-tags may be enriched for properties prior to purification by use of purification handle and purification filter or after purification.

The term unique, when used together with sequences of nucleotides, implies that at least one of the nucleobases and/or backbone entities of the sequence does not appear together with different chemical entities. Preferably, a specific sequence is unique due to fact that no other chemical entities are associated with the same sequence of nucleobases.

Once the library has been formed, one must screen the library for chemical compounds having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. The target can be a protein, peptide, carbohydrate, polysaccharide, glycoprotein, hormone, receptor, antigen, antibody, virus, substrate, metabolite, transition state analog, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-10 converting enzyme, cytokine receptors, PDGF receptor, type II inosine monophosphate dehydrogenase, β-lactamases, and fungal cytochrome P-450. Targets can include, but are not limited to, bradykinin, neutrophil elastase, the HIV proteins, including tat, rev, gag, int, RT, nucleocapsid etc., VEGF, bFGF, TGFβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

The stringency conditions under which the library are screened are normally limited to such condition that maintain the hybridisation between the identifier tag and the anti-tag. High stringency conditions may be applied, however, followed by a renewed synthesis or attachment of the anti-tag. Screening conditions are known to one of ordinary skill in the art.

Chemical compounds having predetermined desirable characteristics can be partitioned away from the rest of the library while still attached to a nucleic acid identifier tag by various methods known to one of ordinary skill in the art. In one embodiment of the invention the desirable products are partitioned away from the entire library without chemical degradation of the attached nucleic acid such that the identifier nucleic acids are amplifiable. The identifier tag may then be amplified, either still attached to the desirable chemical compound or after separation from the desirable chemical compound.

In the most preferred embodiment, the desirable chemical compound acts on the target without any interaction between the tag attached to the desirable chemical compound and the target. In one embodiment, the desirable chemical compounds bind to the target and the bound tag-desirable chemical compound-target complex can be partitioned from unbound products by a number of methods. The methods include nitrocellulose filter binding, column chromatography, filtration, affinity chromatography, centrifugation, and other well known methods.

Briefly, the library is subjected to the partitioning step, which may include contact between the library and a column onto which the target is bound. All tags which have not formed hybridisation products with a chemical entity-tag aggregate or those tags associated with undesirable chemical entities will pass through the column. Additional undesirable chemical entities (e.g., entities which cross-react with other targets) may be removed by counter-selection methods. Desirable complexes are bound to the column and can be eluted by changing the conditions of the column (e.g., salt, etc.) or the tag associated with the desirable chemical compound can be cleaved off and eluted directly.

Additionally, chemical compounds which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined desirable characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of chemical entities on the basis of a desired function; this can be extended to the selection of small molecules with a desired function and specificity. Specificity can be required during the selection process by first extracting identifier sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

Following the selection procedure, anti-tags are recovered. The recovery may be performed by subjecting the selected complexes to stringency conditions which will detach the anti-tag sequences from the identifier tag. In the event the tag and the anti-tag are nucleic acids, the stringency conditions may be increased by increasing the temperature gradually until the two strands of the double helix are melted apart. Further copies of anti-tag sequences may be provided by extension of the identifier sequences using a suitable primer and a polymerase. In the alternative, the recovered anti-tag sequence and/or the identifier sequence tag may be subjected to PCR to form a double stranded product. The strands comprising the sequence that complements at least a part of a unique identifier sequence are subsequently isolated.

The selected chemical entity may be attached to the target during the extension or amplification or may be detached from the target. In one aspect of the invention, it is preferred that the target is immobilised and the chemical compound remain attached to the target during the extension or amplification, to allow for easy recovery of the extension or amplification product by simple elution. In another aspect the selected chemical entities are separated from the unique identifier sequences, prior to, simultaneous with or subsequent to the recovery of the enrichment sequences.

In order to recover the desired anti-tag sequences, it may be appropriate to provide the native as well as the amplified, if present, anti-tag sequences with one part of a molecular affinity pair. The one part of a molecular affinity pair is also referred to herein as a handle. The anti-tags may then be recovered by using the other part of the molecular affinity pair attached to a solid phase, which is possible to isolate. The essential property of the molecular affinity pair is that the two parts are capable of interacting in order to assemble the molecular affinity pair. In the biotechnological field a variety of interacting molecular parts are known which can be used as the molecular affinity pair. Examples include, but are not restricted to protein-protein interactions, protein-polysaccharide interactions, RNA-protein interactions, DNA-DNA interactions, DNA-RNA interactions, RNA-RNA interactions, biotin-streptavidin interactions, enzyme-ligand interactions, antibody-ligand interaction, protein-ligand interaction, etc.

A suitable molecular affinity pair is biotin-streptavidin. The anti-tag sequences can be provided with biotin, e.g. by using a primer attached to a biotin moiety in the amplification or extension step and contacting the biotin tagged anti-tag sequence with beads coated with streptavidin.

After the recovery of the anti-tag sequences, these are contacted with the initial library or a fraction thereof and an enriched library is allowed to be formed by the hybridisation of the anti-tag sequences to the cognate sequence of the unique identifier tag.

The method according to the invention may be repeated one or more times. In a second round of the method, the part of the single stranded library not recognized by an anti-tag sequence may be cleared from the reaction media or the remaining part of the single stranded library may remain in admixture with the enrich library. In general, it is not necessary to separate the remaining part of the single stranded library from the media before the enriched double stranded library is subjected to a second contact with the target because conditions for the preselected function usually are more stringent than the first round, wherefore the members of the single stranded library presumably will not bind to the target. However, to reduce the noise of the system, it may be useful at some events to withdraw from the media the members of the single stranded initial library not mated with an anti-tag sequence. If the anti-tag sequences are provided with one part of a molecular affinity pair, like biotin, the chemical compounds of interest can be extracted from the media by treatment with immobilized streptavidin, e.g beads coated with streptavidin.

As mentioned above, the conditions for performing the second or further selection step is generally more stringent than in the first or preceding step. The increasing stringency conditions in sequential selection rounds provide for the formation of a sub-library of chemical compounds which is narrowed with respect to the number but enriched with respect to the desired property.

In the present description with claims, the terms nucleic acid, oligonucleotide, oligo, and nucleotides are used frequently. The terms nucleotide, nucleotide monomer, or mononucleotides are used to denote a compound normally composed of two parts, namely a nucleobase moiety, and a backbone. The back bone may in some cases be subdivided into a sugar moiety and an internucleoside linker. Mononucleotides may be linked to each other to form a oligonucleotide. Usually, the mononucleotides are linked through an internucleoside linkage. The term nucleic acid covers mononucleotides as well as oligonucleotides. Usually, however, the term denotes an oligonucleotide having from 2 to 30 mononucleotides linked together through internucleoside linkers.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases.

Examples of suitable specific pairs of nucleobases are shown below:

Natural Base Pairs

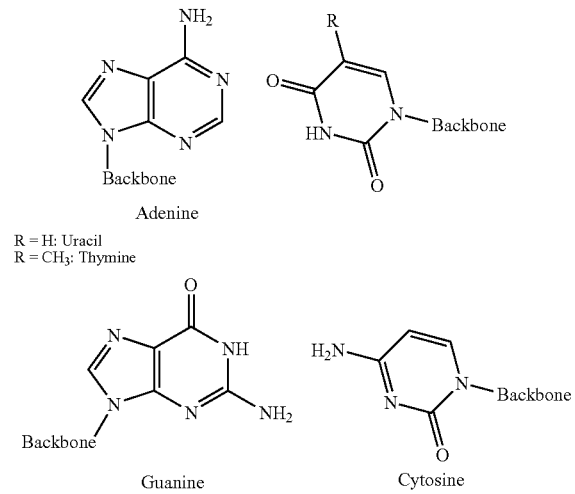

Adenine

R = H: Uracil
R = $CH_3$: Thymine

Guanine    Cytosine

Synthetic Base Pairs

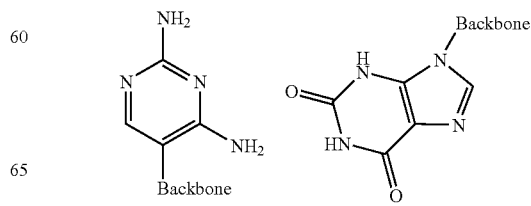

-continued
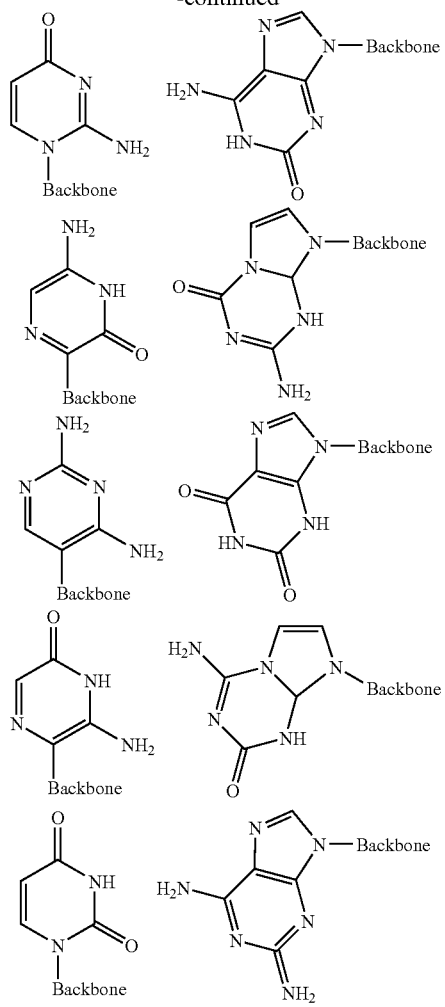
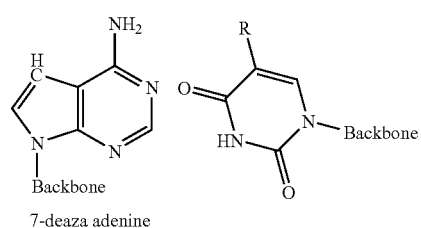
7-deaza adenine
R = H: Uracil
R = CH₃: Thymine
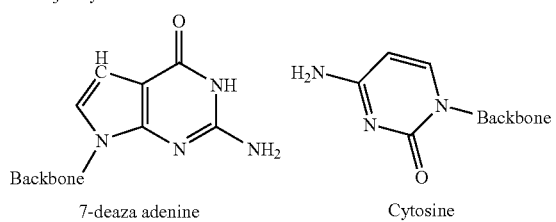
7-deaza adenine     Cytosine
Synthetic purine bases
Suitable examples of backbone units are shown below (B denotes a nucleobase):
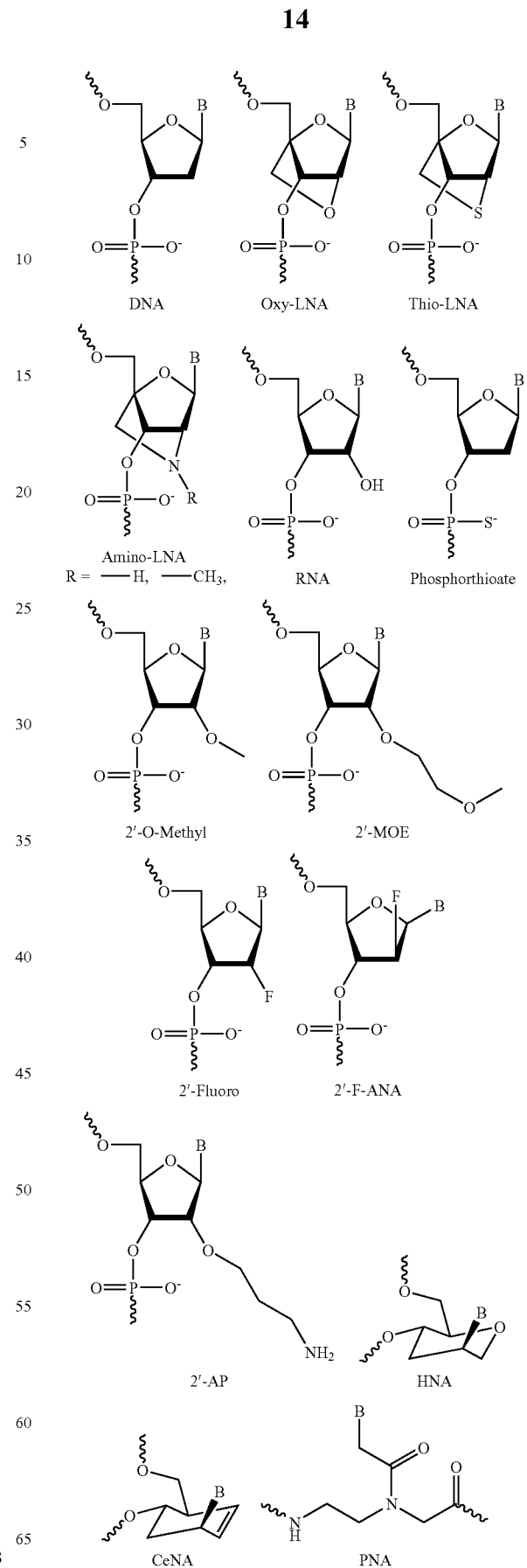

-continued

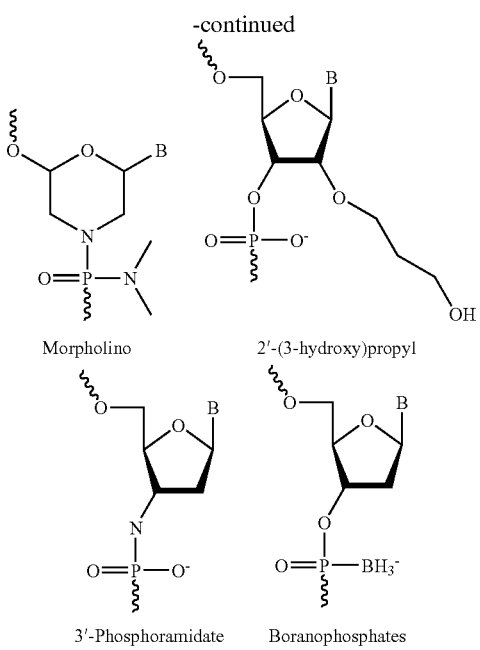

Morpholino  2'-(3-hydroxy)propyl

3'-Phosphoramidate  Boranophosphates

The sugar moiety of the backbone is suitably a pentose but may be the appropriate part of an PNA or a six-member ring. Suitable examples of possible pentoses include ribose, 2'-deoxyribose, 2'-O-methyl-ribose, 2'-fluoro-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose of 2'-deoxyribose. The internucleoside linkage may be the natural occurring phospodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine.

BRIEF DESCRIPTION OF THE FIGURES

FIG. 1 discloses an embodiment of library enrichment, amplification and identification.

FIG. 2 shows an embodiment in which anti-tag sequences not hybridised to a identifier sequence are made double stranded and thus inert.

FIG. 3 shows an embodiment in which an enrichment step is before the purification step.

FIG. 4 shows a general principle of library enrichment, amplification, and identification.

FIG. 5 shows a general principle of library enrichment, amplification, and identification omitting the intermediate amplification step between subsequent enrichment procedures.

FIG. 6 shows a general principle of library enrichment, amplification, and identification in which the initial single stranded library is made double stranded prior to enrichment.

FIG. 7 shows a general principle for library enrichment, in which the anti-tag is not formed until after the one and more enrichment processes.

FIG. 8 shows different methods for attaching a unique identifier sequence to a chemical entity.

DETAILED DESCRIPTION OF THE INVENTION

An embodiment of the general principle of the present invention is shown on FIG. 1. Initially, each chemical entity (denoted by letters A, B, C, . . . ) in a library is attached to a unique identifier tag (denoted a, b, c, . . . ) according to any of the methods disclosed in FIG. 8. The identifier tag comprises information about that particular compound or group of compounds with respect to e.g. structure, mass, composition, spatial position, etc. In a second step, tagged chemical compounds are combined with a set of anti-tag sequences (denoted a', b', c', . . . ). Each anti-tag sequence carries a handle, like biotin, for purification purposes. The anti-tag sequences comprises a segment which is complementary to a sequence of the identifier sequence. The combination of anti-tag sequences and identifier sequences are allowed to form hybridisation products. Optionally, there may be tagged chemical entities present which have not been recognized by an anti-tag. In a third step, the sequences carrying a handle are removed, i.e. the tagged chemical compounds are left in the media while the matter comprising a handle is transferred to a second media. In the event, the handle is biotin it may be transferred to a second media using immobilized streptavidin.

The purified matter may comprise anti-tag sequences not hybridised to a cognate sequence. As these anti-tag sequences are not coupled to a chemical compound to be selected for, the enrichment sequences may remain in the media. However, in some applications it may be preferably to make the excess anti-tag sequences double stranded, as illustrated in FIG. 2, because the double helix normally is inert relative to the selection procedure. The excess anti-tag sequences may be transformed into the double helix state by the use of a primer together with a suitable polymerase and nucleotide triphosphates.

The purified fraction is in step 4 is subjected to a selection process. The selection comprises probing for a set of properties, e.g. but not limited to affinity for a specific protein. In such a case, entities which do not bind to the specific protein will be eliminated. Anti-tags complexed to entities binding to the specific protein may be recovered/be isolated through e.g. the use of its purification handle.

In step 5 isolated anti-tags are optionally amplified through the use of PCR or RTPCR.

In step 6, the initial library of tagged entities produced in step 1, may undergo further rounds of complexation and screening, i.e. the anti-tags from step 5 may be added the library of tagged entities of step 1 and then be submitted to step 3, step 4 and step 5. Step 6 may be repeated.

In step 7, the isolated anti-tags of step 5 may be cloned and their identity be revealed. E.g. in the case of DNA, sequencing may be applied whereby the identity of specific entities with selected properties in the library of tagged entities will be revealed.

The embodiment shown in FIG. 3 resembles that of FIG. 1 except that the non-complexed components are rendered inert, e.g. if the tags and/or anti-tags are composed of single stranded DNA or RNA, they may be transformed into double stranded DNA, RNA or a hybrid thereof. This may be accomplished by use of a primer, nucleotide triphosphates and a polymerase or transcriptase. Furthermore, the sequence of purification (by use of the purification handle on anti-tags) and probing for properties is changed compared to the method of FIG. 1.

In FIG. 4, step 1, a number of entities (denoted by letters A, B, C . . . ), being it mixtures or single compounds are attached to a unique tag more specifically a DNA or RNA sequence or a derivative thereof, holding information on that compound or mixture, such as e.g. structure, mass, composition, spatial information etc.

In step 2, all tags of tagged entities are made double stranded by use of a primer (optionally carrying a @-handle such as e.g. biotin), nucleotide triphosphates and a polymerase or transcriptase. Remaining single stranded DNA or RNA may optionally be digested by use of nucleases.

The mixture, is probed for a set of properties in step 3, e.g. but not limited to affinity for a specific protein. In such a case, entities which do not bind to the specific protein will be eliminated. Anti-tags complexed to entities binding to the specific protein may be recovered/be isolated through e.g. the use of its @-handle.

Isolated anti-tags may optionally be amplified in step 4 through the use of PCR or RTPCR.

In step 5, the library of tagged entities of step 1, may undergo complexation to the isolated and optionally amplified anti-tags of step 3 and 4.

Single stranded components are being digested in step 6 by use of e.g. nucleases. The remaining double stranded subset of the library is optionally subjected to a renewed enrichment of the library according to step 3-6. Steps 3-6 may be repeated as sufficient number of times to obtain an appropriate chemical entity having the desired property.

In step 7, the isolated anti-tags of step 4 can be cloned and their identity be revealed, e.g. in the case of DNA, sequencing may be applied, whereby the identity of specific entities in the library of tagged entities is revealed.

FIG. 5 relates to a method involving a digestion of single stranded oligonucleotides. In a first step a number of entities (denoted by letters A, B, C . . . ), being it mixtures or single compounds, are attached to a unique tag, holding information on that compound or mixture, such as e.g. structure, mass, composition, spatial information etc.

In step 2, mixtures of tagged entities are combined with a set of complementary anti-tags. Anti-tags may be, but is not limited to nucleotide derivatives. Anti-tags may optionally carry a @-handle. The tag and the anti-tags are allowed to form a complex. The complexation may be, but is not limited to hybridization. Some anti-tags will not form a complex with a tagged entity and some tagged entities will not form a complex with an anti-tag.

Non-complexed components is digested in step 3 using e.g. nucleases when the tags and/or anti-tags are composed of DNA or RNA or hybrids thereof.

The mixture of step 3, is probed for a set of properties in step 4, e.g. but not limited to affinity for a specific protein. In such a case, entities which do not bind to the specific protein will be eliminated. Anti-tags complexed to entities binding to the specific protein may be recovered/be isolated through e.g. the use of its @handle. Step 4 may be repeated one or more times.

Isolated anti-tags may optionally be amplified through the use of PCR or RTPCR as illustrated in step 5. Anti-tags may then also be used as described in FIGS. 1-4.

The isolated anti-tags may be cloned and their identity be revealed in step 6, e.g. in the case of DNA, sequencing may be applied, whereby the identity of specific entities in the library of tagged entities will be revealed.

According to FIG. 6, step 1, a number of entities (denoted by letters A, B, C . . . ), being it mixtures or single compounds, are attached to a unique tag more specifically a DNA or RNA sequence or a derivative thereof, holding information on that compound or mixture, such as e.g. structure, mass, composition, spatial information etc.

All tags of tagged entities are made double stranded in step 2 by use of a primer (optionally carrying an @-handle such as e.g. biotin), nucleotide triphosphates and a polymerase or transcriptase. Remaining single stranded DNA or RNA may optionally be digested by use of e.g. nucleases.

In step 3, the mixture is probed for a set of properties, e.g. but not limited to affinity for a specific protein. In such a case, entities which do not bind to the specific protein will be eliminated. Anti-tags complexed to tags having appended entities binding to the specific protein may be recovered/be isolated through e.g. the use of its @-handle. Step 3 may be repeated one or more times.

According to step 4, isolated anti-tags may optionally be amplified through the use of PCR or RTPCR. Anti-tags may then also be used as described in FIGS. 1-4.

The isolated anti-tags may be cloned in step 5 and their identity be revealed, e.g. in the case of DNA, sequencing may be applied. Whereby, the identity of specific entities in the library of tagged entities will be revealed.

FIG. 7, step 1, produces a number of entities (denoted by letters A, B, C . . . ), being it mixtures or single compounds which are attached to a unique tag more specifically a DNA or RNA sequence or a derivative thereof, holding information on that compound or mixture, such as e.g. structure, mass, composition, spatial information etc.

In step 2, the mixture is probed for a set of properties, e.g. but not limited to affinity for a specific protein. In such a case, entities which do not bind to the specific protein will be eliminated. Step 2 may be repeated.

All tags of tagged entities are made double stranded in step 3 by use of a primer (optionally carrying a @-handle such as e.g. biotin), nucleotide triphosphates and a polymerase or transcriptase. Remaining single stranded DNA or RNA may optionally be digested by use of e.g. nucleases.

Anti-tags complexed to tags of entities binding to the specific protein may be recovered/be isolated in step 4 through e.g. the use of its @-handle. Anti-tags may optionally be amplified through the use of PCR or RTPCR. Anti-tags may then also be used as described in FIGS. 1-4.

The isolated anti-tags may be cloned in step 5 and their identity be revealed, e.g. in the case of DNA, sequencing may be applied, whereby, the identity of specific entities in the library of tagged entities is revealed.

FIG. 8 illustrates different chemical means of attaching a unique tag to a functional entity.

EXAMPLES

Example 1

Loading of Entity onto Tag 

Procedure:

25 µL of a 150 mM building block solution in DMF was mixed with 25 µL of a 150 mM solution of EDC in DMF. The mixture was left for 30 min at 25° C. 50 µL of an aminooligo (10 nmol) in 100 mM HEPES buffer pH 7.5 was added and the reaction mixture was left for 20 min at 25° C. The excess building block was removed by extraction with EtOAc (500 µL). The excess EtOAC was removed at reduced pressure in a speedvac. The building block loaded aminooligo was ethanol precipitated twice using NH4OAc and analysed by electron spray mass spectrometry (ES-MS).

Example 2

The following example illustrates the use of the tagging principle for the identification of entities comprising desirable properties isolated from a library of entities. The principle is shown schematically in FIG. 1.

DNA-tagging of peptides for the identification of complexes that bind the integrin receptor αV/β3.

Materials:
Purified human integrin αV/β3 (Chemicon Inc.)
Streptavidin Sepharose 6B (AmershamPharmacia)
Nunc Immunomodule U8 Maxisorp (Biotecline cat# Nun-475078)
Sheared herring DNA (Sigma)
Taq-polymerase (Promega) and 10× Taq-pol buffer
Binding buffer [100 mM NaCl, 5 mM MgCl$_2$, 50 mM Tris-HCl, pH 7.5]
UV-transilluminator
SPDP [N-succinimidyl 3(2-pyridyldithio)propionate] (Molecular Probes, Cat: S-1531)
Micro Bio-Spin 6 (Bio-Rad cat: 732-6221)
6 tagging oligo nucleotides with the following sequences:

```
TO#1:  5'-XCTATGCGGACTGACTGGTAC-3'    (SEQ ID NO: 1)

TO#2:  5'-XCTATGATGCTTAGGCGGTAC-3'    (SEQ ID NO: 2)

TO#3:  5'-XCTATGTACCGTACGTGGTAC-3'    (SEQ ID NO: 3)

TO#4:  5'-XCTATGAATGCTAGCTGGTAC-3'    (SEQ ID NO: 4)

TO#5:  5'-XCTATGGATTGCGCGTGGTAC-3'    (SEQ ID NO: 5)

TO#6:  6'-XCTATGCCACTATTAGGGTAC-3'    (SEQ ID NO: 6)
``` where X=5' C6 amino modifier (Glen research cat# 10-1916-90) suitable for attachment of functional entities such as peptides, small molecules or polymers.

Complementary (Template) oligonucleotides with the following sequences:

```
CO#1:
                                      (SEQ ID NO: 7)
5'-BPTATAGGATCCGTACCAGTCAGTCCGCATAGGAATTCTAGT-3'

CO#2:
                                      (SEQ ID NO: 8)
5'-BPTATAGGATCCGTACCGCCTAAGCATCATAGGAATTCTAGT-3'

CO#3:
                                      (SEQ ID NO: 9)
5'-BPTATAGGATCCGTACCACGTACGGTACATAGGAATTCTAGT-3'

CO#4:
                                      (SEQ ID NO: 10)
5'-BPTATAGGATCCGTACCAGCTAGCATTCATAGGAATTCTAGT-3'

CO#5:
                                      (SEQ ID NO: 11)
5'-BPTATAGGATCCGTACCACGCGCAATCCATAGGAATTCTAGT-3'

CO#6:
                                      (SEQ ID NO: 12)
5'-BPTATAGGATCCGTACCCTAATAGTGGCATAGGAATTCTAGT-3'
```

Where, B=5'-biotin (Glen research Cat#10-1953-95) and P=photocleavable linker (Glen research cat#10-4913-90).

The underlined 10 nucleotide sequences are unique for each tagging oligonucleotide and have a unique complementary oligonucleotide counterpart.

Sequences highlighted in bold are suitable for cloning purposes.

Oligonucleotides for PCR amplification

```
AO#1:  5'-BPTATAGGATCCGTACC-3'        (SEQ ID NO: 13)

AO#2:  5'-ACTAGAATTCCTATG-3'          (SEQ ID NO: 14)
```

6 peptides with the following composition

```
P#1:  GRGDSPC        (SEQ ID NO: 15)

P#2:  GRADSPC        (SEQ ID NO: 16)

P#3:  GRGESPC        (SEQ ID NO: 17)

P#4:  GDGRSPC        (SEQ ID NO: 18)

P#5:  CKKK           (SEQ ID NO: 19)

P#6:  CFFKKK         (SEQ ID NO: 20)
```

A=Alanine, G=Glycin, R=Arginine, D=Aspartate, P=Proline, F=Phenylalanine, K=Lysine and E=Glutamate. All peptides are end-capped by N-terminal carboxylation and C-terminal amidation. Peptides were supplied by Schafer-N A/S, DK-Denmark.

Protocol

Step 1: Tagging of Peptides #1-6 with a Specific Oligonucleotide (TO#1-6).

Each TO oligonucleotide contains a single 5'end amino nucleophile (X) which can be covalently linked to the cysteine thiol-group of a peptide using the heterobifunctional cross-linker SPDP in the following reaction.

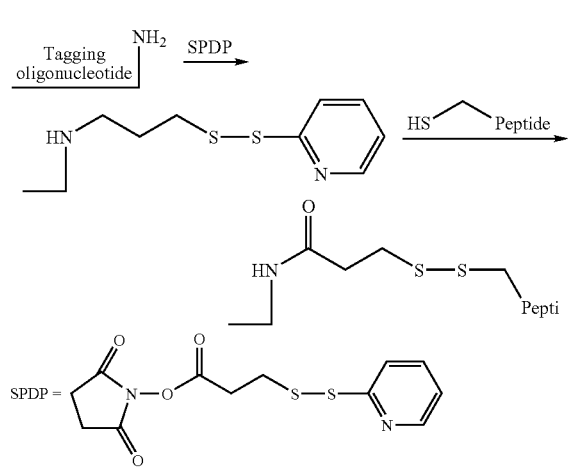

Procedure: 5 nmol amino-oligo is dried and resuspended in 160 μl of 100 mM Hepes-OH, (pH 7.5). 40 μl 20 mM SPDP (in DMSO) is added and incubate for 2 h at 30° C. The sample is extracted with 3×500 μl ethylacetate and dried for 10 min in a speedvac. The sample is purified using microbio-spin 6 column equilibrated with 100 mM Hepes-OH. Add 10 μl of 1 M peptide and incubate at 25° C. for 2 h. Precipitate twice with 2 M NH$_4$OAc/Ethanol. Redissolve in 50 μl H$_2$O and verify tagging by Electrospray-MS analysis (Bruker Inc.).

Step 2: Anneal Complementary Oligonucleotides (CO#1-6) to TO-Peptide Complexes from Step 1.

Procedure:
10 pmol of TO#1-6 loaded with their corresponding peptide is added to a mixture comprising 20 pmol each of CO#1-6 in binding buffer [100 mM NaCl, 5 mM MgCl$_2$, 50 mM Hepes-OH, pH 7.5] and a total volume of 100 µl. The sample is heated to 80° C. for 2 minutes and slowly cooled to room temperature over 30 minutes.

Step 3: Purify Doublestranded DNA-Peptide Complexes (Optional!).

Following annealing, only tagged molecules that have annealed to their complementary oligonucleotide sequences will comprise both a functional entity and a biotin handle (see FIG. 1). Consequently, to reduce "noise" in the selection step, single-stranded tagged-molecules can be removed from the library in a pre-selection step using the biotin handle.

Procedure:

50 µl Streptavidine-sepharose 6B Slurry is washed in 3×1 ml binding buffer before resuspending the beads in 100 µl binding buffer. The CO/TO-peptide annealing mixture is added to the straptavidine beads and incubated at 25° C. for 30 min with agitation. Subsequently, the streptavidine beads are pelleted, the supernatant is discarded and the beads are washed three times with 1 ml of binding buffer. The beads are resuspended in 100 µl binding buffer binding buffer and finally, the CO/TO-peptide complexes are released using photocleavage. The photocleavage reaction is conducted by incubating the sample on a Vilber-Lourmat UV-transilluminator TFX-20.M for 30 seconds at 70% effect. The eluted CO/TO-peptide complexes are removed to a new tube.

Step 4: Enrich Library for Ligands that Bind the Integrin αV/β3 Receptor.

The library of molecules is tested for binding to the integrin αV/β3 receptor immobilised on a plastic surface.

Procedure:

A single well of a Nunc 8 plate is incubated overnight with 100 µl of 1 µg/ml of integrin receptor in standard phosphate-buffered saline (PBS). The well is washed five times with 100 µl PBS followed by blocking using 100 µl 0.5 mg/ml sheared herring DNA in PBS-buffer for 2 h at room temperature. Finally the well is washed five times using 100 µl Integrin binding buffer [Tris-HCl (pH 7.5), 137 mM NaCl, 1 mM KCl, 1 mM MgCl$_2$, 1 mM CaCl$_2$ and 1 mM MnCl$_2$].

The CO/TO-peptide complexes are added to the immobilised integrin and incubated at 37° C. for 30 min. The supernatant is removed and the immobilised integrin is washed 5 times using 100 µl integrin binding buffer. The CO/TO-ligand complexes are eluted heating the sample to 80° C. for 5 min. The sample is cooled to room-temperature. 1 µl of the sample is used for PCR amplification using 10 pmol each of AO#1 and 2 as external primers in a reaction comprising 10 mM Tris-HCl pH 9.0, 50 mM KCl, 1 mM MgCl$_2$, 0.1% Triton X-100, 250 mM each of dATP, dCTP, dGTP and dTTP. The sample is run with initial denaturation at 94° C., for 2 min and 30 cycles using denaturation at 94° C. for 30 seconds, annealing at 44° C. for 30 seconds and elongation at 72° C. for 15 seconds. Finally, the sample is precipitated Step 5: Isolate Single Stranded Templates.

For subsequent selection and amplification rounds the non-template strand of the amplified PCR products should be should be removed. This step is conducted using specific purification of the biotinylated template oligo.

Procedure:

50 µl of streptavidine-sepharose 6B is washed three times with 1 ml of binding buffer. The washed beads are incubated with 25 µl (<10 pmol) of PCR product from step 4 in 100 µl binding buffer for 30 min at 25° C. Spin the sample briefly to collect beads. Remove supernatant and wash five times using 800 µl H$_2$O. The beads are resuspended in 500 µl 10 mM NaOH for 2 min at room temperature. The supernatant is removed and the beads are resuspended in 100 mM biotin in 100 µl H$_2$O. For elution the sample is incubated at 95° C. for 10 min with agitation. Subsequently, the excess biotin is removed by Micro-spin gel-filtration.

Step 6: Anneal the New Population of Template Oligos to the Library of Tagged Peptides from Step 1.

The new population of single stranded template oligonucleotides which are enriched for sequences that represent ligands for the integrin αV/β3 receptor are annealed to the library of tagged-peptides from step 1 as described in step 2 and subjected to yet another round of selection and amplification. The selection and amplification procedure (step 2-6) is repeated for 5 rounds.

Step 7: Identification of Ligands.

The identity of enriched double stranded DNA fragments specific for a ligand entity or entities is established by DNA cloning in a M13mp18 plasmid vector and examining individual clones by sequence analysis. For statistical purposes more than 30 clones is sequenced to identify dominant sequence(es) within the pool of cloned sequence tags. Since the dominant DNA sequence cloned corresponds to a ligand the sequence bias directly identifies the ligand candidate(s) suitable for further examination.

Example 3

The following example illustrates the use of the tagging principle for the identification of a DNA sequence representing a small molecule isolated from a library of sequences. The principle is shown schematically in the figures.

DNA-Tagging of Biotin and Glutathione for the Identification of Complexes that Bind Streptavidine.

Materials:
Streptavidin Sepharose 6B (AmershamPharmacia)
Taq-polymerase (Promega) and 10× Taq-pol buffer
Binding buffer [100 mM NaCl, 5 mM MgCl$_2$, 50 mM Tris-HCl, pH 7.5];
SPDP [N-succinimidyl 3(2-pyridyldithio)propionate] (Molecular Probes, Cat: S-1531)
N-hydroxysuccinimidylester-biotin (Fluka#14405)
Glutathione (Sigma)
Micro Bio-Spin 6 (Bio-Rad cat: 732-6221)
T7 Exonuclease (gene 6) and 5× buffer
Tagging oligo nucleotides with the following sequences:

```
TO#1: 5'-XCTATGCGGACTGACTGGTAC-3'      (SEQ ID NO: 1)

TO#2: 5'-XCTATGANNNNNNNNNCGGTAC-3',    (SEQ ID NO: 21)
(65,536 sequence combinations)
``` where X=5' C6 amino modifier (Glen research cat# 10-1039-90) suitable for attachment of functional entities such as peptides, small molecules or polymers. N is G, A, T or C Complementary (Template) oligo nucleotides with the following sequences:

```
CO#1:
                                       (SEQ ID NO: 22)
5'-T_sA_sT_sAGGATCCGTACCAGTCAGTCCGCATAGGAATTCTAGT-3'

CO#2:
                                       (SEQ ID NO: 23)
5'-T_sA_sT_sAGGATCCGTACCGNNNNNNNNNTCATAGGAATTCTAGT-3'
```

Where, S denotes the position of a phosphorothioate in the DNA backbone.

The underlined 10 nucleotide sequences are unique for each tagging oligonucleotide or pool of tagging oligonucleotides and have a unique complementary oligonucleotide counterpart. Sequences highlighted in bold are suitable for cloning purposes.

Oligonucleotides for PCR amplification

```
AO#1: 5'-T_sA_sT_sAGGATCCGTACC-3'    (SEQ ID NO: 24)

AO#2: 5'-ACTAGAATTCCTATG-3'          (SEQ ID NO: 14)
```

Where, S denotes the position of a phosphothioate in the DNA backbone.

Protocol

Step 1: Tagging Biotin with TO#1 and Tagging Glutathione with TO#2.

All TO oligonucleotides contain a single 5'end amino nucleophile(X) which can be used for covalent linking of small molecules. Biotin is linked to the TO#1 amino-group using NHS-biotin (Merck) in the following reaction.

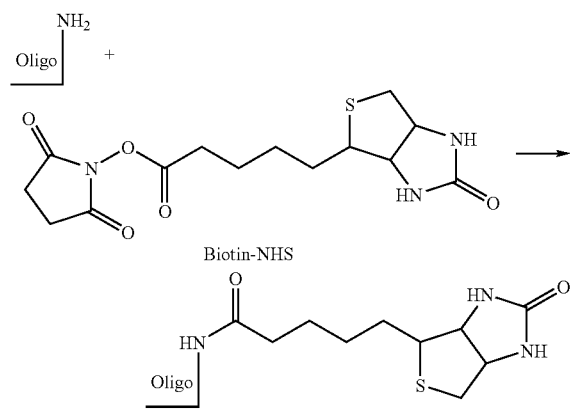

Glutathione is linked to the pool of oligonucleotides using the heterobifunctional cross-linker SPDP in the following reaction.

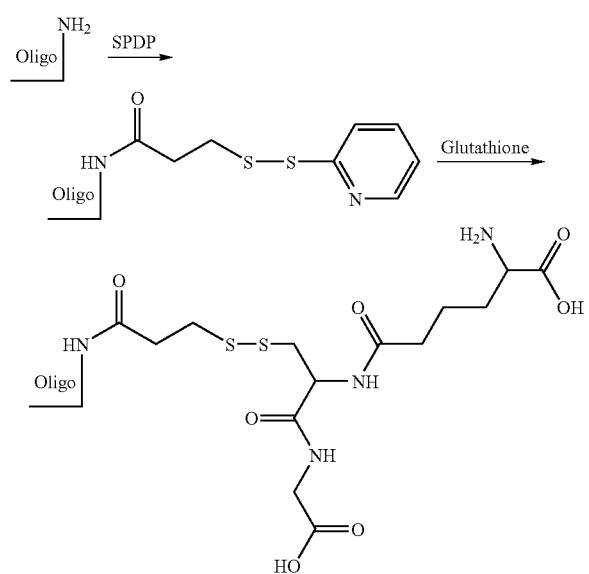

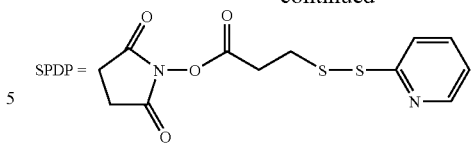

Procedure:

Tagging of Biotin with TO#1:

5 nmol of TO#1 oligonucleotide is dried down and resuspended in 80 µl 100 mM Hepes-OH buffer (pH 7.5). 20 µl of 50 mM NHS-Biotin (in DMSO) is added to the oligonucleotide and the sample incubated at 30° C. for 2 hours. The sample is extracted twice using 200 µl ethyl-acetate before purification on a Micro-spin 6 column. Tagging of biotin is verified using Electrospray-MS (Bruker Inc.).

Tagging of Glutathione (GSH) with TO#2:

5 nmol of TO#2 is dried down and resusspended in 160 µl of 100 mM Hepes-OH, (pH 7.5). 40 µl 20 mM SPDP (in DMSO) is added and the sample is incubated for 2 h at 30° C. The sample is extracted with 3×500 µl ethylacetate and dried for 10 min in the speedvac. The sample is purified using microbio-spin 6 column equilibrated with 100 mM Hepes-OH. 10 µl of 0.1 M GSH is added and the sample is incubated at 25° C. for 2 h. Precipitate twice with 2 M $NH_4OAc$/Ethanol. Redissolve in 50 µl $H_2O$ and verify tagging by Electrospray-MS analysis (Bruker Inc.).

The single biotin sequence tag and the 65.536 different glutathione sequence tags comprise a total of 65.537 different sequence-tags. The library is mixed to comprise equi-molar amounts of each sequence tag. Consequently, the library consists of 65.536-fold excess of tagged glutathione over tagged biotin.

Step 2: Anneal Complementary Oligonucleotides (CO#1 & 2) to TO Complexes from Step 1.

Procedure:

A total of 10 pmol of tagged library molecules is added to a mixture comprising 20 pmol of template molecules (CO#1 & 2) comprising 65.536 fold excess of CO#2 over CO#1 in a binding buffer [100 mM NaCl, 5 mM $MgCl_2$, 50 mM Hepes-OH, pH 7.5] and a total volume of 100 µl. The sample is heated to 80° C. for 2 minutes and slowly cooled to room temperature over 30 minutes.

Step 3: Purify Doublestranded DNA Complexes (Optional!).

Following annealing, only tagged molecules that have annealed to their complementary oligonucleotide sequences will comprise both a functional entity and a phosphorothioate backbone handle (see FIG. 1). Consequently, to reduce "noise" in the selection step, single-stranded tagged-molecules can be removed from the library in a pre-selection step using the phosphorothioate handle.

Procedure:

50 µl of activated thiopropyl-sepharose slurry is washed in 3×1 ml binding buffer before resuspending the beads in 100 µl binding buffer. The CO/TO annealing mixture is added to the thiopropyl-sepharose beads and incubated at 30° C. for 30 min with agitation. Subsequently, the beads is pelleted, the supernatant discarded and the beads is washed three times with 1 ml of binding buffer. The beads is resuspended in 100 µl binding buffer binding buffer and finally, the CO/TO complexes are released using by incubation with 100 µl of 50 mM DTT in binding buffer. The eluted CO/TO complexes are removed to a new tube.

Step 4: Enrich Library for Ligands that Binds to Streptavidine.

The library of molecules is tested for binding to the streptavidine sepharose 6B.

Procedure:

50 µl of streptavidine-sepharose 6B slurry is washed three times with 1 ml of binding buffer. 10 µl of library molecules eluted at step 3 is incubated with the streptavidine in 100 µl of binding buffer for 10 minutes at 25° C. with agitation. Subsequently, the sample is washed five times using 1 ml of binding buffer. The ligand DNA is eluted by incubating of the sample in 100 µl H$_2$O at 95° C. for 5 minutes. The sample is cooled to room-temperature. 1 µl of the sample is used for PCR amplification using 10 pmol each of AO#1 and 2 as external primers in a reaction comprising 10 mM Tris-HCl pH 9.0, 50 mM KCl, 1 mM MgCl$_2$, 0.1% Triton X-100, 250 mM each of dATP, dCTP, dGTP and dTTP. The sample is run with initial denaturation at 94° C., for 2 min and 30 cycles using denaturation at 94° C. for 30 seconds, annealing at 44° C. for 30 seconds and elongation at 72° C. for 15 seconds. Finally, the sample is precipitated Step 5: Isolate Single Stranded Templates.

For subsequent selection and amplification rounds the non-template strand of the amplified PCR products should be should be removed. This step is conducted using specific purification of the template oligo strand comprising a phosphorothioate backbone.

Procedure:

The doublestranded PCR product is subjected to exonuclease digestion using phage T7 (gene 6) exonuclease. This enzyme is a doublestrand specific 5' exonuclease that is inhibited by the presence of phosphorothioate in the DNA backbone. 20 µl of doublestranded PCR product from step 4 is incubated in exonuclease T7 buffer before addition of 50 units of T7 exonuclease enzyme. The sample is incubated at 30° C. for 10 minutes. The sample is extracted once with 100 µl phenol before precipitation using NH$_4$-acetate/ethanol. Resuspend sample in H$_2$O.

Step 6: Anneal the New Population of Template Oligos to the Library of Tagged Molecules from Step 1.

The new population of single-stranded template oligonucleotides which are enriched for sequences that represent ligands for the streptavidine is annealed to the library of tagged molecules from step 1 as described in step 2 and subjected to yet another round of selection and amplification.

The selection and amplification procedure (step 2-6) is repeated for 5 rounds.

Step 7: Identification of Ligands.

The identity of enriched double stranded DNA fragments specific for a ligand entity or entities is established by DNA cloning in a M13mp18 plasmid vector and examining individual clones by sequence analysis.

For statistical purposes more than 30 clones is sequenced to identify dominant sequence(es) within the pool of cloned sequence tags. Since the dominant DNA sequence cloned corresponds to a ligand the sequence bias directly identifies the ligand candidate suitable for further examination.

The invention claimed is:

1. In a method of determining the identity of a chemical entity in a combinatorial library comprising a plurality of structurally distinct chemical entities,
   wherein the chemical entities are non-polymeric compounds,
   wherein each chemical entity is tagged with an entity tag identifying the structure of the chemical entity,
   wherein each chemical entity comprises a plurality of fragments,
   wherein the entity tag consists essentially of a plurality of fragment tags, each fragment tag identifying one of the fragments constituting a fragment of the chemical entity tagged by said entity tag,
   wherein the identity of at least one chemical entity is determined from the entity tag with which it is tagged,
   the improvement comprising
   ligating at least one pair of fragment tags by enzyme-catalysed ligation.

2. The method of claim 1, wherein the tagged entity is obtained by initially providing a tagged first fragment, said tagged first fragment comprising a first fragment and a first fragment tag which identifies said first fragment, and, sequentially or simultaneously, combining said first fragment with one or more further fragments and combining said first fragment tag with one or more further fragment tags, wherein each further fragment tag identifies a further fragment.

3. The method of claim 2 which comprises
   (1) directly attaching a first fragment tag to a first fragment,
   (2) ligating a second fragment tag to the first fragment tag, and
   (3) ligating a second fragment to the first fragment, wherein steps (2) and (3) may be simultaneous or may be interchanged, and wherein as a result of steps (2) and (3), the second fragment tag is indirectly attached, through said first fragment tag and first fragment, to said second fragment.

4. The method of claim 3, which further comprises ligating a third fragment to the second fragment, and a third fragment tag to the second fragment tag, simultaneously or sequentially.

5. The method of claim 2, wherein the fragment tags are combined solely by enzyme-catalyzed ligation.

6. The method of claim 1, wherein the library entities have a molecular weight of more than 1000 Da.

7. The method of claim 1, wherein the library entities have a molecular weight of less than 1000 Da.

8. The method of claim 1, wherein said entity tags are oligonucleotides.

9. The method of claim 8, wherein said oligonucleotide entity tags form a complex with oligonucleotide entity anti-tags.

10. The method of claim 9, wherein said oligonucleotides are selected from ribonucleic acids and deoxyribonucleic acids.

11. The method of claim 9, wherein said complex is a double stranded oligonucleotide selected from duplex DNA oligonucleotides and hybrid DNA/RNA oligonucleotides.

12. The method of claim 8, wherein the oligonucleotides have from 2 to 30 consecutive nucleotides linked by internucleoside linkers.

13. The method of claim 9, wherein the oligonucleotide entity tags and said oligonucleotide entity anti-tags have from 2 to 30 consecutive nucleotides linked by internucleoside linkers.

14. The method of claim 8, wherein the individual nucleotide residues of the oligonucleotide are composed of a nucleobase moiety and a backbone, wherein the backbone is composed of a sugar moiety and an internucleoside linker.

15. The method of claim 14, wherein the nucleobase moiety of the nucleotides of the oligonucleotide tags is selected from naturally occurring nucleobases.

16. The method of claim 14, wherein the nucleobase moiety of the nucleotides of the oligonucleotide tags is selected from adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diamino-purine, 5-methylcytosine, 5-($C^3$-$C^6$)-alkynylcytosine, 5-fluorouracil, 5-bromouracil, pseudoisocytosine, 2-hydroxy-5-methyl-4-triazolopyridine, isocytosine, isoguanine and inosine.

17. The method of claim 14, wherein the nucleobase moiety of the nucleotides of the oligonucleotide tags is selected from adenine, guanine, thymine, cytosine, 5-methylcytosine, and uracil.

18. The method of claim 14, wherein the backbone units of the oligonucleotide tags are selected from the group consisting of

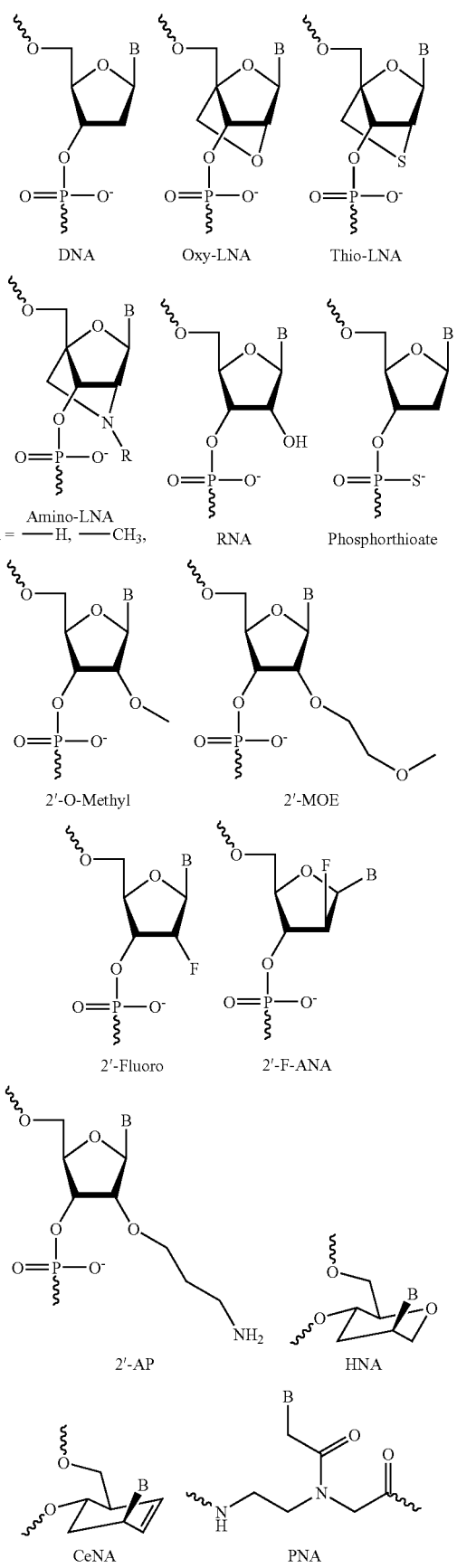

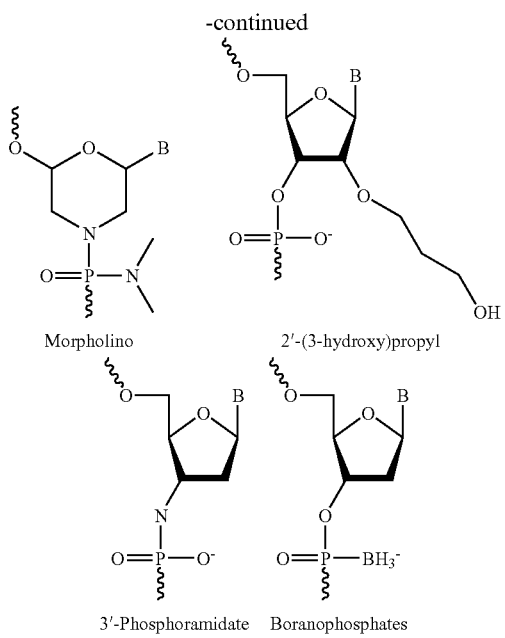

wherein B denotes a nucleobase.

19. The method of claim 14, wherein the sugar moiety of the backbone is a pentose.

20. The method of claim 14, wherein the pentose is selected from the group consisting of ribose, 2'-deoxyribose, 2'-O-methyl-ribose, 2'-fluoro-ribose and 2'-4'-O-methylene-ribose (LNA).

21. The method of claim 14, wherein the internucleoside linker connects the 3' end of a preceeding nucleotide monomer to the 5' end of a succeeding nucleotide monomer, wherein the sugar moiety of the backbone is a pentose and wherein the internucleoside linker is selected from a phosphodiester linker, a phosphorothioate linker, a methylphosphonate linker, a phosphoramidate linker, a phosphotriester linker and a phosphodithioate linker.

22. The method of claim 14, wherein the nucleic acid monomers of the oligonucleotide include naturally occurring nucleosides of the DNA or RNA family connected through phosphodiester linkages.

23. The method of claim 22, wherein the members of the DNA family include deoxyadenosine, deoxyguanosine, deoxythymidine, and deoxycytidine.

24. The method of claim 14, wherein the members of the RNA family include adenosine, guanosine, uridine, cytidine, and inosine.

25. The method of claim 1, wherein the chemical entity is associated with an entity tag through a covalent bond.

26. The method of claim 25, wherein the covalent bond is a cycloaddition product.

27. The method of claim 25, wherein the covalent bond is an alkylation product.

28. The method of claim 25, wherein the covalent bond is an arylation product.

29. The method of claim 25, wherein the covalent bond is an acylation product.

30. The method of claim 25, wherein the covalent bond is an amide bond.

31. The method of claim 25, wherein the covalent bond is a carboxylic ester bond.

32. The method of claim 25, wherein the covalent bond is a sulfonamide bond.

33. The method of claim 25, wherein the covalent bond is a disulfide bond.

34. The method of claim 25, wherein the covalent bond is an S-alkyl bond.

35. The method of claim 25, wherein the covalent bond is an NR-alkyl bond.

36. The method of claim 25, wherein the covalent bond is an O-alkyl bond.

37. The method of claim 25, wherein the covalent bond is an aryl-vinyl bond.

38. The method of claim 25, wherein the covalent bond is an alkyne-vinyl bond.

39. The method of claim 25, wherein the covalent bond is an oxime bond.

40. The method of claim 25, wherein the covalent bond is an imine bond.

41. The method of claim 25, wherein the covalent bond is a bicyclic product.

42. The method of claim 25, wherein the covalent bond is a trizole.

43. The method of claim 25, wherein the covalent bond is a hexene.

44. The method of claim 25, wherein the covalent bond is a 7-Oxa-bicyclo[2.2.1]hept-2-ene derivative.

45. The method of claim 25, wherein the covalent bond is a 7-Aza-bicyclo[2.2.1]hept-2-ene derivative.

46. The method of claim 25, wherein the covalent bond is 7-Methyl-7-aza-bicyclo[2.2.1]hept-2-ene.

47. The method of claim 1, wherein there are $10^3$-$10^6$ entities in said library.

48. The method of claim 1, wherein there are $10^3$-$10^8$ entities in said library.

49. The method of claim 1, wherein there are $10^3$-$10^{10}$ entities in said library.

50. The method of claim 1, wherein there are $10^5$-$10^8$ entities in said library.

51. The method of claim 1, wherein there are $10^5$-$10^{10}$ entities in said library.

52. The method of claim 1, in which each fragment tag is directly attached to the fragment it identifies, prior to ligation of the fragments to form the chemical entity and prior to the ligation of the fragment tags to form the entity tag.

53. The method of claim 52, in which the fragments are ligated to form the chemical entity prior to the ligation of the attached fragment tags to form the entity tag.

54. The method of claim 52, in which the fragment tags are ligated to form the entity tag prior to the ligation of the fragments to form the chemical entity.

55. The method of claim 1,
wherein the entity tags of the combinatorial library are oligonucleotides,
wherein, prior to generating the combinatorial library comprising a plurality of structurally distinct chemical entities, an initial, oligonucleotide tagged combinatorial library of chemical entity fragments is generated by appending a different identifier oligonucleotide tag fragment to each of a plurality of different chemical entity fragments,
wherein each different identifier oligonucleotide tag fragment identifies a different chemical entity fragment,
wherein the initial, oligonucleotide tagged combinatorial library of chemical entity fragments is subjected to a condition for partitioning,
wherein a subset of chemical entity fragments having a predetermined property is partitioned from the remainder of the initial, oligonucleotide tagged combinatorial library of chemical entity fragments, thereby generating a partitioned oligonucleotide tagged library of chemical entity fragments, wherein the partitioned oligonucleotide tagged library of chemical entity fragments is subjected to further tag fragment enzyme-catalysed ligation steps and further chemical entity fragment reaction steps, thereby generating the oligonucleotide tagged combinatorial library of structurally distinct chemical entities, wherein the oligonucleotide tagged combinatorial library of chemical entities is subjected to a condition for partitioning, wherein a subset of chemical entities having a predetermined property is partitioned from the remainder of the oligonucleotide tagged combinatorial library of structurally distinct chemical entities, thereby generating a partitioned oligonucleotide tagged library of structurally distinct chemical entities, wherein identifier oligonucleotides appended to one or more partitioned, chemical entities having the predetermined property are recovered, wherein said recovered identifier oligonucleotides identifies in a specific manner the one or more partitioned chemical entities, and wherein the chemical entities having the predetermined property are identified by decoding the recovered identifier oligonucleotides identifying the one or more partitioned chemical entities.

56. The method of claim 55, wherein the further tag fragment enzyme-catalysed ligation steps and the further chemical entity fragment reaction steps are performed sequentially.

57. The method of claim 55, wherein the further tag fragment enzyme-catalysed ligation steps and the further chemical entity fragment reaction steps are performed simultaneously.

58. The method of claim 55, wherein the partitioned oligonucleotide tagged library of structurally distinct chemical entities is subjected to one or more further partitioning steps using increasing stringency conditions.

59. The method of claim 55, wherein each chemical entity is prepared by sequential chemical entity fragment reaction steps and wherein each chemical entity identifier oligonucleotide tag is prepared by sequential oligonucleotide fragment tag enzyme catalysed ligation steps.

60. The method of claim 55, wherein the chemical entities are selected from non-polymeric molecules having a molecular weight of less than 1000 Da.

61. In a method of determining the identity of a chemical entity in a combinatorial library comprising a plurality of structurally distinct chemical entities, wherein each chemical entity is tagged with an entity tag identifying the structure of the chemical entity, wherein each chemical entity comprises a plurality of fragments, wherein the entity tag consists essentially of a plurality of fragment tags, each fragment tag identifying one of the fragments constituting a fragment of the chemical entity tagged by said entity tag, wherein the identity of at least one chemical entity is determined from the entity tag with which it is tagged, wherein the entity tags of the combinatorial library are oligonucleotides, wherein, prior to generating the combinatorial library comprising a plurality of structurally distinct chemical entities, an initial, oligonucleotide tagged combinatorial library of chemical entity fragments is generated by appending a different identifier oligonucleotide tag fragment to each of a plurality of different chemical entity fragments, wherein each different identifier oligonucleotide tag fragment identifies a different chemical entity fragment, wherein the initial, oligonucleotide tagged combinatorial library of chemical entity fragments is subjected to a condition for partitioning, wherein a subset of chemical entity fragments having a predetermined property is partitioned from the remainder of the initial, oligonucleotide tagged combinatorial library of chemical entity fragments, thereby generating a partitioned oligonucleotide tagged library of chemical entity fragments, wherein the partitioned oligonucleotide tagged library of chemical entity fragments is subjected to further tag, fragment enzyme-catalysed ligation steps and further chemical entity fragment reaction steps, thereby generating the oligonucleotide tagged combinatorial library of structurally distinct chemical entities, wherein the oligonucleotide tagged combinatorial library of chemical entities is subjected to a condition for partitioning, wherein a subset of chemical entities having a predetermined property is partitioned from the remainder of the oligonucleotide tagged combinatorial library of structurally distinct chemical entities, thereby generating a partitioned oligonucleotide tagged library of structurally distinct chemical entities, wherein identifier oligonucleotides appended to one or more partitioned, chemical entities having the predetermined property are recovered, wherein said recovered identifier oligonucleotides identifies in a specific manner the one or more partitioned chemical entities, and wherein the chemical entities having the predetermined property are identified by decoding the recovered identifier oligonucleotides identifying the one or more partitioned chemical entities, the improvement comprising ligating at least one pair of fragment tags by enzyme-catalysed ligation.

* * * * *